United States Patent
Sorum

(10) Patent No.: US 9,446,108 B2
(45) Date of Patent: Sep. 20, 2016

(54) FISH VACCINE

(71) Applicant: NORGES MILJØ-OG BIOVITENSKAPELIGE UNIVERSITET (NMBU), Oslo (NO)

(72) Inventor: Henning Sorum, Oslo (NO)

(73) Assignee: NORGES MILIØ-OG BIOVITENSKAPELIGE UNIVERSITET (NMBU, Oslo (NO)

( * ) Notice: Subject to any disclaimer, the term of this patent is extended or adjusted under 35 U.S.C. 154(b) by 0 days.

(21) Appl. No.: 14/401,257

(22) PCT Filed: May 14, 2013

(86) PCT No.: PCT/EF2013/059972
§ 371 (c)(1),
(2) Date: Nov. 14, 2014

(87) PCT Pub. No.: WO2013/171236
PCT Pub. Date: Nov. 21, 2013

(65) Prior Publication Data
US 2015/0132341 A1    May 14, 2015

Related U.S. Application Data

(60) Provisional application No. 61/646,388, filed on May 14, 2012.

(30) Foreign Application Priority Data

May 14, 2012  (NO) .................................. 20120561

(51) Int. Cl.
| | | |
|---|---|---|
| A01N 63/00 | (2006.01) | |
| A61K 39/02 | (2006.01) | |
| C07K 16/12 | (2006.01) | |
| A61K 39/116 | (2006.01) | |
| A61K 39/00 | (2006.01) | |

(52) U.S. Cl.
CPC ......... *A61K 39/0208* (2013.01); *A61K 39/107* (2013.01); *A61K 39/116* (2013.01); *C07K 16/1239* (2013.01); *A61K 2039/521* (2013.01); *A61K 2039/552* (2013.01); *A61K 2039/70* (2013.01)

(58) Field of Classification Search
CPC .................................................. A61K 39/0208
See application file for complete search history.

(56) References Cited

FOREIGN PATENT DOCUMENTS

WO        99/63824       12/1999

OTHER PUBLICATIONS

Toranzo, Alicia E., et al., "A Review of the Main Bacterial Fish Diseases in Mariculture Systems," Elsevier, Amsterdam, Aquaculture vol. 246, No. 1-4 (May 18, 2005) pp. 37-61, XP027614565.
Thompson, F.L., et al., 2004 "Biodiversity of Vibros" Microbiol. and molecular biol. Reviews, pp. 403-431.
Greger, E., et al., "Vaccine development for winter ulcer disease, Vibrio viscosus, in Atlantic salmon, *Salmo salar* L" vol. 22, No. 3, May 1999, pp. 193-199, XP002701233.
Benediktsdottir E., et al., "Charaterization of Vibrio viscosus and Vibrio wodanis isolated at different geographical locations: . . . " International Journal of Systematic and Evolutionary Microbiology . . . vol. 50, (2000) pp. 479-488, XP003017238.
Hastein, T., et al., "Bacterial Vaccines for Fish—an Update of the Current Situation Worldwide," Developments in biologicals, Karger, Basel, vol. 121, Jan. 1, 2005, pp. 55-74, XP00913490.
Gudmundsdottir, Bjarnheidur K., et al., "Vaccination against atypical furunculosis and winter ulcer disease of fish," ScienceDirect, Vaccine 25 (2007) pp. 5512-5523, XP022148588.
Sorum, H., "Vintersar hos oppdrettslaks-et smarbeid mellom to bakterier for a dempe sykdommen?" Faktaark fran forskningsradet Nov. 26, 2009 (Translation Not Available).
Thorarinsson, R., Lystad, Y (2003), Norsk Fiskeoppdrett, nr. 10, 34-38, "Vintersar: Ny kunnskap skaper optimisme" (Translation Not Available).

*Primary Examiner* — Albert Navarro
(74) *Attorney, Agent, or Firm* — Casimir Jones, S.C.; John Jones; Tanya Arenson

(57) ABSTRACT

The present invention relates to novel compositions for medical use, particularly for use as vaccines. The present invention relies upon the dependence of the bacteria of the species *Alliivibrio wodanis* (formerly *Vibrio wodanis*) in the pathogenesis in the unrecognized, novel disease wodanosis (Norwegian: odinose), as well as in the chronic disease stages of winter ulcer in a composition together with *Moritella viscosa* (*M. viscosa*). in addition, it is also related herein to a composition comprising inactivated bacteria of one or more culture(s) of the species *M. viscosa* cultivated in physical contact with cells of *A. wodanis* to improve the technical composition and protection of a vaccine against winter ulcer. The invention also relates to use of such vaccine compositions in prevention and/or treatment of wodanosis and winter ulcer, methods for the production of such vaccines, and to methods for preventing, controlling and combating *Alliivibno wodanis* infection and chronic winter ulcer in fish.

18 Claims, 14 Drawing Sheets

FISH VACCINE

CROSS REFERENCE TO RELATED APPLICATIONS

The present application is a Section 371 U.S. national stage entry of pending International Patent Application No. PCT/EP2013/059972, international filing date May 14, 2013, which claims priority to U.S. Provisional Patent Application No. 61/646,388, filed May 14, 2012, and which claims priority to NO Patent Application No. 20120561, filed May 14, 2012, the contents of which are incorporated by reference in their entireties.

TECHNICAL FIELD

The present disclosure relates to the field of vaccines, particularly vaccines for vaccinating fish against disease.

BACKGROUND OF THE DISCLOSURE

Winter ulcer is a known and only partly unsolved problem within the salmonid farming industry, especially relevant for the Atlantic salmon and rainbow trout farming. Winter ulcer causes annual losses of around NOK 100 million to the Norwegian aquaculture industry. In addition new findings show that more than 7 million salmons already vaccinated against winter ulcer are potentially lost to the industry only during the first 3 months after sea transfer due to ulcers that often is demonstrated to be winter ulcer. Industry officials has also identified a substantial lack of reporting of the illness, as the reporting of this disease is not mandatory and required. Out of the NOK 100 million registered losses, NOK 20 million are caused by down-classification of fish products due to scars and damaged muscle tissue which again causes a lowered meat quality.

Winter ulcer has also been a problem to the aquaculture industry in Scotland, Iceland, Faroe Islands, Ireland, Canada and Maine in USA (Bruno et al. 1998, Gudmundsdottir et al. 2006, Whitman et al. 2000).

*Moritella viscosa* has since long been shown to be causing winter ulcer in farmed salmonid fish. From the first known outbreaks of disease in the 1980s focus has been on preventing and controlling the disease by controlling the bacterium *M. viscosa*. Since 1993, fish have been vaccinated against winter ulcer, and the main strategy today is to use a multi-component vaccine in vaccination of smolts before sea launch. *M. viscosa* is one of the up to six microbial components in the multi-component vaccines from all the vaccine producers. The other components than *M. viscosa* are intended to protect against other diseases than winter ulcer. Vaccination of farmed Atlantic salmon has for nearly three decades been performed with one single intra-peritoneal injection of a multi-component vaccine protecting against up to 6 different infectious diseases before smoltification and sea launch. Since vaccination against winter ulcer started the vaccine effect has not been optimal, being successful with ≥60% relative protection.

From the first known outbreak of winter ulcer in the early 1980s, and throughout the time period to the present, it is well documented that *Vibrio wodanis* (*V. wodanis*) is isolated along with *M. viscosa* from both head kidney and wounds in diseased salmon. It was from the beginning of the 1990s, both in Norway and Iceland documented that *M. viscosa* could reproduce many of the symptoms seen in winter ulcer by using a healthy salmon in the challenge. Parallel challenge with *V. wodanis* did not produce any disease. It was employed intramuscular challenge in these early experiments. Hence, it was concluded that *V. wodanis* did not have any important role in the development of winter ulcer.

Aunsmo et al. in 2008 document ulcers as accounting for 43% of the mortality in Atlantic salmon smelts already vaccinated against winter ulcer during the 3 first months after transfer to sea. It was shown that ulcers occurred in outbreaks with both *M. viscosa* and *V. wodanis* isolated from the kidneys of vaccinated but diseased salmon. In addition ulcers occurred as a cause of low baseline mortality during the first 3 months. Further winter ulcer occurs as a problem in all parts of the growth period.

The diseased post-smolts will also have a lower chance of becoming fully grown salmons having a higher mortality rate. The study published by Aunsmo in his 2010 dissertation had followed 2.7 million vaccinated post-smolts after transfer to sea in 20 different cages at 10 different localities in Norway. Overall mortality of the smolts was about 2.5% with the main cause of mortality explained by wounds (mainly winter ulcer) accounting for 43% of deaths in spite of the use of the only relatively effective commercial multi-component vaccine with the winter ulcer component. Extrapolated, 2.5% of the about 280 millions of salmon smolts 'launched' in total annually in Norway die from wounds that primarily is caused by winter ulcer the first 3 months after transfer from freshwater to net pens in sea.

Wodanosis as defined herein may produce skin ulcers in combination with septicemia or may be dominated by septicemia in the summer months which may mean that as much as 4-5% of the smolts are lost the first 3 months in sea because of either winter ulcer or wodanosis.

Winter ulcer occurs throughout the complete growth period except for the summer months and the total losses including loss of salmon near to slaughter is not known. However, in 2008 it was reported a direct loss from down-classification of slaughtered salmon of NOK 20 million suspected to be mainly caused by winter ulcer in only one single salmon farm (ref Fiskehelserapporten V I, 2008).

Winter ulcer is a disease not required to report, but by an annual phone call to the local Fish Health Services made by an official at the National Veterinary Institute annually between 35 and 55 farms is "remembered" to have had outbreaks of winter ulcer by the various Fish Health Services. In the fish health report from the National Veterinary Institute covering 2010 it is noted that a "Smolt syndrome" has been recorded just after transfer to sea. The smolts grow poorly and develop ulcers and it is related to improper smoltification in large batches of salmon transferred to unusually cold water. It is reason to believe that winter ulcer bacteria together with *Tenacibaculum* spp. bacteria may be related to these ulcer problems.

As a result from a collaboration between the vaccine company Alpharma (Pharmaq from 2004) and the Icelandic fish health research scientists at Keldur, University of Iceland, Reykjavik, an autogen vaccine against atypical furunculosis was made in 1991. From 1992 *V. wodanis* was added to this vaccine against atypical furunculosis because the land-based fish farms in Iceland pumped seawater from relatively large depths that resulted in winter ulcer in the tanks. Possibly because *V. wodanis* was easier to cultivate than *M. viscosa*, *V. wodanis* was chosen for this specially made autogenic vaccine that however did not improve the situation. From 1993 *M. viscosa* was included as a third component in the vaccine and the occurrence of winter ulcer dropped considerably.

However, after a collective evaluation in 1995 *V. wodanis* was removed from the vaccine without any increase in the number of outbreaks in the land-based tanks. (Thorarinsson og Lystad, Norsk Fiskeoppdrett, nr 10, 2003).

In 2007 *V. wodanis* was reclassified as *Aliivibrio wodanis* (*A. wodanis*) (WoRMS (2011). *Aliivibrio wodanis* Lunder, Serum, Holstad, Steigerwalt, Mowinckel & Brenner, 2000. Accessed through: World Register of Marine Species at http://www.marinespecies.org/aphia.php?p=taxdetails&id=570711 on 2012 May 12). The terms *A. wodanis* and *V. wodanis* are used as synonyms in this description.

*A. wodanis* has once previously been included in an experimental vaccine against winter ulcer in Atlantic salmon in a challenge and vaccination study without causing increased protection against winter ulcer (Greger and Goodrich, 1999). In the experiment no pathogenicity was demonstrated by *A. wodanis* by intraperitoneal injection in rainbow trout and therefore the vaccinated Atlantic salmon were not challenged with *A. wodanis*. The lack of disease development in rainbow trout at 10° C. after intraperitoneal injection may be caused by fish species specificity or any methodological impact not reported. The vaccinated salmon fry was challenged intraperitoneally with *M. viscosa* in the study of Greger and Goodrich (1999) and no increased protection against *M. viscosa* caused after introduction of *A. wodanis* in the vaccine was reported.

Thorarinsson & Lystad et al (2003), summarized research and field experiences related to the virulence of *V. wodanis* in winter ulcer, but concluded that it did not have an immediate role in the disease. In addition, it was also mentioned therein using *V. wodanis* in a vaccine did not provide any protection against winter ulcer.

A specific vaccine tested in the field on Iceland containing *A. wodanis* did not improve the protection against winter ulcer and *A. wodanis* was later withdrawn from the vaccine since *M. viscosa* alone was reported to protect effectively against winter ulcer (Thorarinsson & Lystad et al (2003)).

Greger & Goodrich (1999) also concluded that *V. wodanis* was not a pathogen. The same conclusion was drawn by Lunder et al. 1995.

Accordingly no virulence in disease has yet been proven for *A. wodanis*. In addition, no medical use thereof and particularly not a medical use thereof in the form of a functional vaccine has been proven. Furthermore, the role of *A. wodanis* in winter ulcer has never been clarified, as it has been concluded to be of no use in the development of vaccines for this disease. Hence, the role of *V. wodanis* in diseases affecting fish remains blurred, and especially its interaction, if any, with *M. viscosa*.

In summary, there is a need in the art to overcome or at least mitigate the problems associated with disease in fish, such as Salmonidae, by finding alternative vaccine solutions to the vaccines available as of today. There is a further need in the art for improvements of the vaccines to winter ulcer as well as vaccines for the treatment and/or prevention of the herein defined novel disease, wodanosis. There is a further need in the art for an improved vaccine which will remove most of the loss caused by ulcers in the salmonid farming and also improve the product quality due to the occurrence of reduced scars and connective tissue in the meat of salmon surviving winter ulcer especially in spring and summer when sea water temperatures rise and ulcers heal leaving scars.

SUMMARY OF THE DISCLOSURE

The above presented problems have now been overcome, or at least mitigated, by the findings presented herein resting on a novel vaccine concept based upon the role of the bacterium *Alliivibrio wodanis* (*A. wodanis*) in the pathogenesis in causing wodanosis as well as in winter ulcer together with *Moritella viscosa* (*M. viscosa*). It is shown herein, the importance of these two bacteria in disease in fish, especially in winter ulcer and wodanosis and furthermore the importance of their interaction in the pathogenesis and the different stages thereof.

This is the first time that a functioning vaccine has been produced that is effective against two different infectious diseases caused by two causative bacteria that in a complex interplay modulate the combined pathogenesis tightly. The findings as presented herein also support the concept of the presence of acute and chronic disease stages in both wodanosis and winter ulcer, which also necessitates the development of a vaccine which is effective against all specific stages of disease.

Accordingly, the present disclosure relates to a composition comprising inactivated bacteria of spp. *Alliivibrio wodanis* (*A. wodanis*) for medical use, such as inactivated bacteria of one or more single culture(s) of *A. wodanis*. In addition, it is also related to herein, a composition which comprises inactivated bacteria of one or more single culture(s) of *A. wodanis*, and/or which further comprises, inactivated bacteria of one or more mixed culture(s) of spp. *A. wodanis* and *Moritella viscosa* (*M. viscosa*) for medical use. These compositions can also be complemented with inactivated bacteria of one or more single culture(s) of *M. viscosa* to be especially efficient as a protective vaccine against the winter ulcer part of the disease. Further, these compositions contain inactivated bacteria from one or more single and/or mixed cultures which have been cultured at different salt concentrations and temperatures, for optimizing the antigenic appearance of these bacteria when treating and/or preventing the acute and the chronic stages of disease of winter ulcer and wodanosis which vary due to the varying conditions in the sea further explained herein.

The compositions are described herein as vaccines, and for use in the treatment and/or prevention of wodanosis and/or winter ulcer. Also provided herein are methods for producing these compositions, methods for treating and/or preventing wodanosis and/or winter ulcer in fish, as well as vaccine compositions and kits comprising the inactivated bacteria as described herein.

Figure 1:
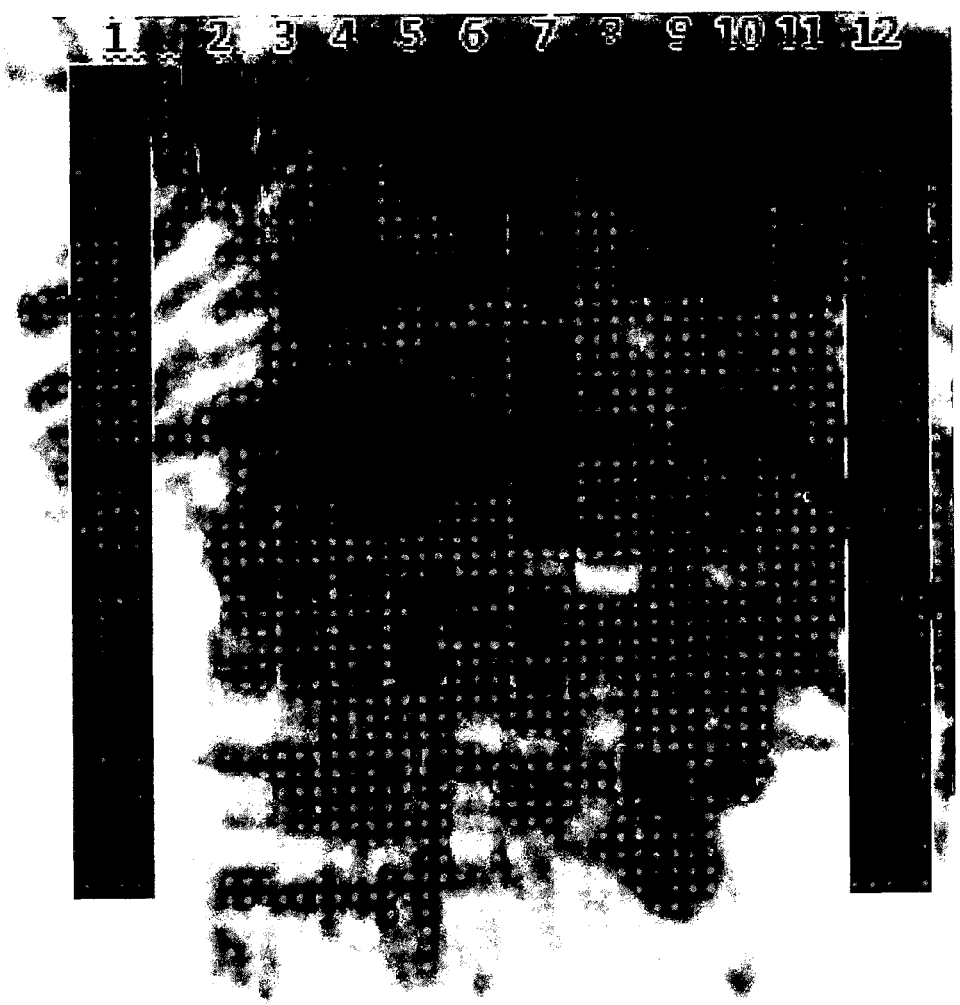
FIGS. 1 and 2
Figure 2:

Western blot of various isolates of *A. wodanis* cultivated at 12° C. in 2.5% NaCl (FIG. 1) and at 12° C. in 0.9% NaCl (FIG. 2) and developed with an antiserum produced in rabbit from a co-cultivation of *A. wodanis* and *M. viscosa* at 8° C. Lane 1: See Blue ladder (FIG. 1), Magic Marker (FIG. 2), Lane 2: NVI 03/09/160 Irish Atlantic salmon, Lane 3: NVI 04/60/17347 Atlantic cod, Lane 4: NVI 06/09/178 Atlantic salmon, Lane 5: NVI 06/09/170 Atlantic salmon, Lane 6: NVI 06/09/139 Atlantic salmon, Lane 8: NVI 06/09/194-5465 Atlantic salmon, Lane 9: NVI 06/09/194-5461 Atlantic salmon, Lane 10: NVI 06/09/441$^T$ Atlantic salmon, Lane 11: NVI 06/09/139 Atlantic salmon, Lane 12: See Blue ladder (FIG. 1), Magic Marker (FIG. 2).

FIG. 3

Mortality curves from bath challenge with a co-culture of *A. wodanis* NVI 06/09/139-Ft 5426 and *M. viscosa* NVI 06/09/139-Ft 5427 in a vaccination experiment with Atlantic salmon smolt at 8° C. (low temperature). Mortality is given as proportion on the Y-axis while days are given on the X-axis. The curve marked "Mv vaccine" represents a group of salmon that were vaccinated with *M. viscosa* bacteria that were cultivated as a single culture. The curve marked "Mv/Aw vaccine" represents a group of salmon that were vaccinated with bacteria from a co-culture of *M. viscosa* and *A. wodanis*.

FIG. 4

Mortality curves from bath challenge with a co-culture of *A. wodanis* NVI 06/09/139-Ft 5426 and *M. viscosa* NVI 06/09/139-Ft 5427, in a vaccination experiment with Atlantic salmon smolt at 9-10° C. (high temperature) (Example 3). Mortality is given as fraction on the Y-axis while dates (month-day) are given on the X-axis. The curve marked "Mv" represents a group of salmon that were vaccinated with *M. viscosa* bacteria that were cultivated as a single culture. The curve marked "Mv/Aw" represents a group of salmon that were vaccinated with bacteria from a co-culture of *M. viscosa* and *A. wodanis* while the curve marked "Vw" represents a group of salmon that were vaccinated with *A. wodanis* bacteria that were cultivated as single culture.

FIG. 5

Figure 4:
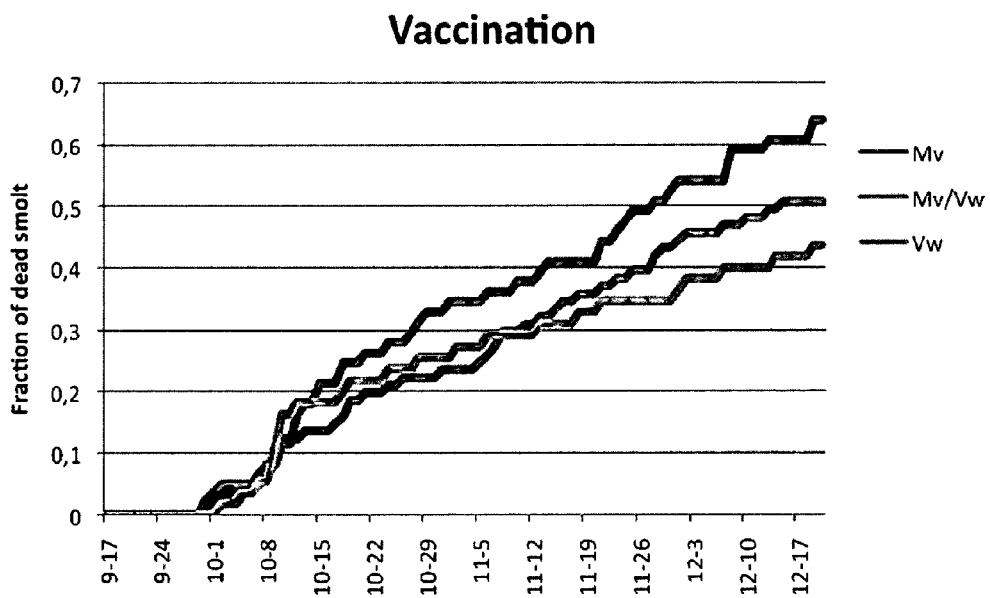

Seawater temperature during the vaccination experiment in FIG. 4 Example 3, degrees Celsius on the Y-axis and days on the X-axis

FIG. 6

Seawater temperature (Example 5) in the tanks of the experiment with intraperitoneal challenge with *A. wodanis* and *M. viscosa* at high temperature (Tank 3, 10° C.) and low (Tank 7, 8° C.). Y-axis degrees Celsius, X-axis dates. "Kar" (Norwegian) means Tank.

FIG. 7

Seawater temperature in the tanks of the experiments in Example 3, 4 and 5 that were run in parallel. Y-axis degrees Celsius, X-axis dates. "Kar" (Norwegian) means Tank.

FIG. 8

Salinity in per mille (Y-axis) in the marine tank water of the experiments in Example 3, 4 and 5 after mixing in freshwater at 8° C. to regulate the temperature, X-axis indicate dates.

FIG. 9 a

Western blot membranes with antigens from *M. viscosa* NVI 06/09/139, Ft 5427, and *A. (V.) wodanis* NVI 06/09/139, Ft 5426, cultured as single cultures at 8° C. and in 2.5% NaCl and applied in three repeated lanes for each strain and transferred identically to both membranes. The upper membrane was blotted with rabbit antibody (X) against a co-culture of *M. viscosa* NVI 06/09/139, Ft 5427, and *A. (V.) wodanis* NVI 06/09/139, Ft 5426 in 0.9% NaCl at 8° C. The lower membrane was blotted with rabbit antibody (Y) against separately grown cultures of *M. viscosa* NVI 06/09/139 and *A. (V.) wodanis* NVI 06/09/139 in 0.9% NaCl at 8° C. that were mixed after growth just before the rabbit was immunized.

FIG. 9 b

Western blot membranes with antigens from *M. viscosa* NVI 06/09/139 and *A. (V.) wodanis* NVI 06/09/139 cultured as single cultures at 8° C. and in 0.9% NaCl and applied in three repeated lanes for each strain and transferred identically to both membranes. The upper membrane was blotted with rabbit antibody (X) against a co-culture of *M. viscosa* NVI 06/09/139 and *A. (V.) wodanis* NVI 06/09/139 in 0.9% NaCl at 8° C. The lower membrane was blotted with rabbit antibody (Y) against separately grown cultures of *M. viscosa* NVI 06/09/139 and *A. (V.) wodanis* NVI 06/09/139 in 0.9% NaCl at 8° C. that were mixed after growth just before the rabbit was immunized.

FIG. 9 c

Western blot membranes with antigens from *M. viscosa* NVI 06/09/139 and *A. (V.) wodanis* NVI 06/09/139 cultured as single cultures at 12° C. and in 2.5% NaCl and applied in three repeated lanes for each strain and transferred identically to both membranes. The upper membrane was blotted with rabbit antibody (X) against a co-culture of *M. viscosa* NVI 06/09/139 and *A. (V.) wodanis* NVI 06/09/139 in 0.9% NaCl at 8° C. The lower membrane was blotted with rabbit antibody (Y) against separately grown cultures of *M. viscosa* NVI 06/09/139 and *A. (V.) wodanis* NVI 06/09/139 in 0.9% NaCl at 8° C. that were mixed after growth just before the rabbit was immunized.

FIG. 9 d

Western blot membranes with antigens from *M. viscosa* NVI 06/09/139 and *A. (V.) wodanis* NVI 06/09/139 cultured as single cultures at 12° C. and in 0.9% NaCl and applied in three repeated lanes for each strain and transferred identically to both membranes. The upper membrane was blotted with rabbit antibody (X) against a co-culture of *M. viscosa* NVI 06/09/139 and *A. (V.) wodanis* NVI 06/09/139 in 0.9% NaCl at 8° C. The lower membrane was blotted with rabbit antibody (Y) against separately grown cultures of *M. viscosa* NVI 06/09/139 and *A. (V.) wodanis* NVI 06/09/139 in 0.9% NaCl at 8° C. that were mixed after growth just before the rabbit was immunized.

FIG. 10

Cumulative mortality in vaccination trial where Atlantic salmon (average 150 gram) were bath challenged 5 months and 1 week (21. Dec. 2012) after intraperitoneal vaccination. There was minimal mortality in the experimental tank the weeks before challenge. The water supplied was natural undesinfected sea water taken from a depth of 60 meter in the Oslofjord representing a sub-branch of the Gulf current. The water had a temperature of approximately 7.5° C. from before the time of bath challenge to 16. January when the intake water was heated with electricity to obtain 2 degrees Celsius increase. From 16. January the sea water temperature was approximately 9.5° C. until mid-February.

Group 1, (n=28 at challenge) was vaccinated with PBS buffer and was negative control, 13 died within 39 days from bath challenge.

Group 2, (n=38 at challenge) was vaccinated with *M. viscosa* cultivated at 8° C. at both 2.5 and 0.9% NaCl, i.e. one culture comprising *M. viscosa* cultivated at 8° C. at 2.5% NaCl and one culture comprising *M. viscosa* cultivated at 8° C. at 2.5% were mixed together and used for the vaccination. 11 died within 39 days from challenge.

Group 3, (n=34 at challenge) was vaccinated with *A. wodanis* cultivated at 10° C. at both 2.5 and 0.9% NaCl, i.e. one culture comprising *A. wodanis* cultivated at 10° C. at 2.5 NaCl and one culture comprising *A. wodanis* cultivated at 10° C. at 0.9% NaCl were mixed together and used for the vaccination. 26 died within 39 days from challenge.

Group 4, (n=39 at challenge) was vaccinated with *A. wodanis* and *M. viscosa* cultivated in same culture flask from inoculation at both 8 and 10° C. at both 2.5 and 0.9% NaCl, four different cultures, i.e. one mixed culture of *A. wodanis* and *M. viscosa* cultivated at 8° C. and 0.9% NaCl, one mixed culture of *A. wodanis* and *M. viscosa* cultivated at 8° C. and 2.5% NaCl, one mixed culture of *A. wodanis* and *M. viscosa* cultivated at 10° C. and 0.9% NaCl and one mixed culture of *A. wodanis* and *M. viscosa* cultivated at 10° C. and 2.5% NaCl were mixed together and used for the vaccination. 13 dies within 39 days from challenge.

Group 5, (n=31 at challenge) was vaccinated with *M. viscosa* cultivated at 8° C. at both 2.5 and 0.9% NaCl (as in Group 2), with *A. wodanis* cultivated at 10° C. at both 2.5 and 0.9% NaCl (as in Group 3), and with *A. wodanis* and *M. viscosa* (as in Group 4) cultivated in same culture flask from inoculation at both 8 and 10° C. at both 2.5 and 0.9% NaCl, eight different cultures, 5 died within 39 days from challenge.

FIG. 11

Unvaccinated Atlantic salmon contracting "Winter ulcer" (Lunder et al. 1995). Arrows indicate periods of the year when the various diseases occur. Antigens (cultivated at both 2.5 and 0.9% NaCl) useful in vaccine to protect farmed salmonids at various parts of the year are written accordingly inside arrows Thickness of arrow indicates relative frequency of diseased fish with that diagnosis. Wodanosis caused by *A. wodanis* (Aw) causing acute disease is shown with the upper light grey arrow. Wodanosis and Winter ulcer combined in salmon co-infected with both *A. wodanis* and *M. viscosa* (Mv) is a chronic disease and is shown by the middle light grey arrow. Winter ulcer caused by *M. viscosa* generating a peracute disease is shown by a dark grey arrow. Typical annual temperature fluctuation in sea water at Atlantic salmon farms is indicated by a grey line with temperature shown on the y-axis and months at x-axis.

FIG. 12

Illustration of Atlantic salmon vaccinated with commercial vaccines with *M. viscosa* cultivated at high salt and low temperature contracting "Winter ulcer". Arrows indicate periods of the year when the various diseases occur. Thickness of arrow indicates relative frequency of diseased fish with that diagnosis. Wodanosis caused by *A. wodanis* causing acute disease is shown with the upper light grey arrow. Wodanosis and Winter ulcer combined in salmon co-infected with both *A. wodanis* and *M. viscosa* is a chronic disease and is shown by the middle light grey arrow. Winter ulcer caused by *M. viscosa* generating a peracute disease is shown by a dark grey arrow. Typical annual temperature fluctuation in sea water at Atlantic salmon farms is indicated by a grey line with temperature shown on the y-axis and months at x-axis.

FIG. 13

Illustration of Atlantic salmon vaccinated with commercial vaccines with *M. viscosa* cultivated at high salt and low temperature diseased and living with what is currently defined as "Winter ulcer" at different time during the year. Arrows indicate periods of the year when the various diseases occur. Thickness of arrow indicates relative frequency of diseased fish with that diagnosis. Wodanosis caused by *A. wodanis* causing acute disease is shown with the upper light grey arrow. Wodanosis and Winter ulcer combined in salmon co-infected with both *A. wodanis* and *M. viscosa* is a chronic disease and is shown by the middle light grey arrow. Winter ulcer caused by *M. viscosa* generating a peracute disease is shown by a dark grey arrow. Typical annual temperature fluctuation in sea water at Atlantic salmon farms is indicated by a grey line with temperature shown on the y-axis and months at x-axis.

DEFINITIONS

*Aliivibrio wodanis* (*A. wodanis*) (Urbanczyk et al. 2007), formerly called *Vibrio wodanis* (*V. wodanis*), which names may be used interchangeably herein, is a bacterium which was described in parallel with *Moritella viscosa* (*M. viscosa*) (Benediktsdòttir et al. 2000) (formerly called *Vibrio viscosus* (*V. viscosus*) (Lunder et al. 2000) for the first time by Lunder (1992), Lunder et al. (1995) and Lunder et al. (2000) and later by Benediktsdòttir et al. (2000). It is to be noted that any of the compositions as presented herein can be prepared from any isolate/strain of *A. wodanis* and/or *M. viscosa*, as it may be desirable depending on which geographical area the vaccine composition is intended for. Still, strong cross protection between strains is an expected measure. Accordingly, the vaccinating effect does not solely rely upon the specific strain used. The type strains of *M. viscosa* ((NVI 881478T (=NCIMB 13584$^T$)) and *A. wodanis* ((NVI 881441$^T$ (=NCIMB 13582$^T$)) are public and available at the National Collection of Industrial and Marine Bacteria, Aberdeen, Scotland and were deposited May 3, 1999 by Henning Swum, Norwegian School of Veterinary Science/Norwegian College of Veterinary Medicine, Post Box 8146 Dep, 0033 Oslo Norway. They may be commercially obtained therefrom. These type strains are also available from ATCC (American Type Culture Collection, 10801 University Boulevard, P.O. Box 1549, Manassas, Va. 20110 USA,); BAA-105 (*Moritella viscosa*, NVI 88/478$^T$) and BAA-104 (*Aliivibrio wodanis*, NVI 88/441$^T$) and from CRBIP (Centre de Ressources Biologiques de l'Institut Pasteur, Institut Pasteur Service des Archives, 28 rue du Dr Roux, 75724 Paris cedex 15, France) CIP109754 T *Moritella viscosa*, NVI 88/478$^T$, deposited 2007 by Henning Sørum and CIP108769 T *Aliivibrio wodanis*, NVI 881441$^T$ deposited 2005 by Henning Sørum.

In addition the reference strains of *M. viscosa* (NVI 06/09/139-Ft 5427 (NCIMB accession number 42122)) and *A. wodanis* (NVI 06/09/139-Ft 5426 (=NCIMB accession number 42121)) have been deposited according to the Budapest Treaty at the National Collection of Industrial and Marine Bacteria (NCIMB Ltd., Ferguson Building, Craibstone Estate, Bucksburn, Aberdeen, AB21 9YA, Scotland) by the depositor Norwegian School of Veterinary Science, Post Box 8146 Dep, 0033 Oslo Norway on Mar. 7, 2013 These strains are also publically available from the Norwegian School of Veterinary Science and further described in the publications Karlsen et al 2012, Bjørnsdottir et al 2012.

Further strains of *M. viscosa* and *A. wodanis* have been described, such as by Ast et al. (Syst Appl Microbiol, 2009 September; 32(6):379-86), Lunder et al. (Int. J. Syst. Evol. Microbiol. 50: 427-450), Benediktsdòttir et al. (Int J Syst Evol Microbiol, 2000, 50: 479-88) and Whitman et al. (Aquacul. Assoc. Canada Spec. Publ. 2000, No. 4, 115-117).

The type strains, reference strains and the other strains referred to herein are isolated from its source and are biologically pure.

The strains mentioned herein were prospected in Norway.

"Wodanosis" (Norwegian: odinose) is a disease characterized by a pathogenesis dominated by septicemia similar to cold water vibriosis caused by *Aliivibrio salmonicida* (formerly *Vibrio salmonicida*), a close relative to *A. wodanis*. In addition to a minor extent ulcers mostly in the form of depressions caused by necrosis in the skin at the base of the back fin and tail fins leading to loss of the fin and necrosis of the area around the fin base, a form of the disease described "fin rot". Wodanosis as a separate disease is mainly seen in fish at temperatures of sea-water from about 9 to 10 degrees Celsius and above, but may also occur in sea water at temperatures down to less than about 6° C., which is further explained herein. The reason for this epidemiological scenario is probably because at sea water temperatures below 8-9° C. diseased farmed Atlantic salmon with symptoms of "winter ulcer" in a population vaccinated against *M. viscosa* will most commonly have a chronic co-infection between *M. viscosa* and *A. wodanis* where *A. wodanis* downregulates the virulence in *M. viscosa* and the antigenic outlook of both bacteria changes (Example 6).

Figure 11:
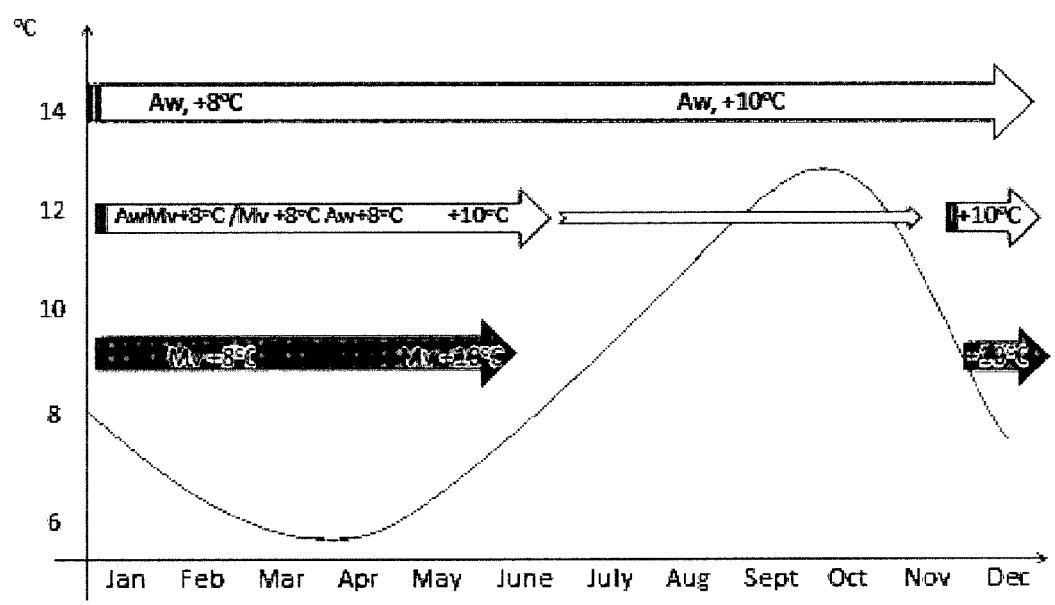
Figure 12:
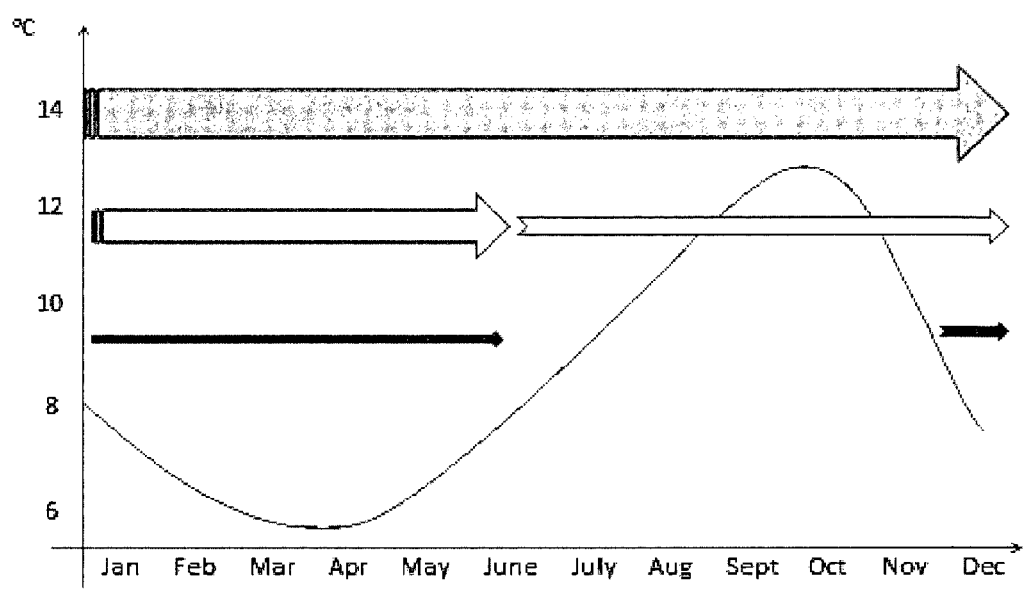
Figure 13:
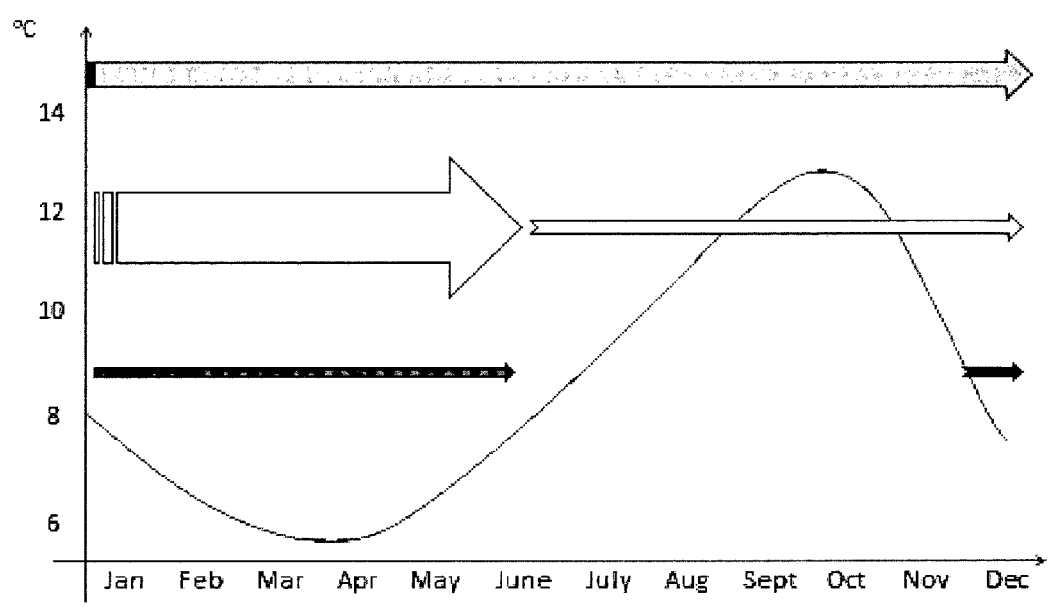

Sole wodanosis caused by *A. wodanis* will most often occur in water containing merely *A. wodanis* without *M. viscosa* where *A. wodanis* causes acute disease and relatively high mortality at this temperature as in Example 7 and also as illustrated in FIGS. 11, 12 and 13, i.e. at higher temperatures. The internal pathological changes caused by the septicemia of fish with wodanosis are mainly bleedings in the liver, peritoneal fat tissues and ascites. The main symptoms of wodanosis have been observed but not recognized as separate from symptoms from winter ulcer by Jensen (2003). Wodanosis may also occur as a separate disease without nearly any relation with *M. viscosa* in sea-water with low concentration of *M. viscosa* but with relatively high concentration of *A. wodanis* occurring at higher sea temperatures. The density of *M. viscosa* and *A. wodanis* in the marine water varies apparently independent of each other at various depths dependent of currents and other unknown factors. In such cases the mortality caused by wodanosis may be high even at temperatures down to 6 degrees Celsius or even lower. Salmon die from septicemia but ulcers of the skin, mandibula, head and eye and fin rot in one or more of all fins of all fins may also be common. Eroded sharp fin spines are probably an important mechanical cause of self-made wounds and wounds made in other fish that are used by *A. wodanis* in establishing wodanosis. When *M. viscosa* is infecting salmon in cooperation with *A. wodanis, M. viscosa* is dominating the disease when the temperatures are below 9 degrees Celsius. However *A. wodanis* is controlling the virulence of *M. viscosa* making the infection more prolonged and not as aggressive as if *M. viscosa* is infecting alone. However, above 9 degrees Celsius *M. viscosa* is not particularly active in creating infection. This means that the temperature span for wodanosis may be wider than for winter ulcer at the warmer side. Ulcers made from a co-infection of *M. viscosa* and *A. wodanis* are not commonly possible to separate macroscopically from ulcers occurring in wodanosis or winter ulcer caused by *A. wodanis* and *M. viscosa*, respectively.

"Winter ulcer" is a disease which is characterized by skin ulcers that develop from skin swellings into open ulcers and later into larger ulcerated skin areas where the underlying muscle tissue is exposed and often destroyed by necrosis. Winter ulcer is mainly occurring at sea water temperatures from <6 to 8° C. wherein *M. viscosa* is most clinically active and is aggressively attacking the skin of the fish directly creating small ulcers and in addition infecting the fish septicemically mainly through the gill epithelium (Lunder et al. 1995, Løvoll at al. 2008, Karlsen at al. 2012).

"Salmonidae" is a family of ray-finned fish, which is the only living family currently placed in the order Salmoniformes. These are also referred to herein as salmonids. Salmonidae includes salmon, trout, chars, freshwater whitefishes and graylings. An example of a fish suitable for being vaccinated with a composition as defined herein is a fish originating from the family Salmonidae, but said composition may also be suitable for vaccinating other fish than salmonids, such as Atlantic cod, turbot and cleaner fish, including five species of wrasse (Labridae), used on fish farms in Norway and to a lesser extent in Scotland, Shetland and Ireland to reduce the infestation of sea lice on the skin of Atlantic salmon.

A composition comprising "inactivated bacteria" as disclosed herein refers in the present context to a composition comprising bacteria, a component thereof, and/or one or more antigenic part(s) thereof, also including extracellular products such as toxins or enzymes produced thereby, which due to one or more modifications have lost their virulence, but which still induces an immune response in a recipient, e.g a fish, which is sufficient to provide an immunizing effect. A component or an antigenic part of a bacterium, such as a surface protein or a part thereof, is a component or part of a bacterium which is sufficient to by itself induce an immune response. A composition comprising inactivated bacteria may e.g. be killed or naturally dead bacterial cells, attenuated cells (e.g. attenuated by directed or non-directed mutation), or a component comprising one or more antigenic part(s) thereof. Inactivation of bacteria can be performed by using chemicals, such as formalin, or by using heat, radiation, or antibiotics, but is not limited thereto. A composition comprising inactivated bacteria may in the present context be formulated as a liquid or as a dry powder, according to procedures known in the art.

A "single culture" of bacteria of either *A. wodanis* or *M. viscosa* refers to a culture that contains one species of bacteria, e.g. the colonies or the suspended cells formed during the cultivation process will contain either single homogenic cells of *A. wodanis* or *M. viscosa*, i.e. either of these. These cultures contain non-modified, original bacteria, i.e. meaning that their physical external appearance has not been altered by the influence of other factors present in the culture, such as other bacteria. A number of different single cultures of the different species may be mixed together in a vaccine.

On the other hand, a "mixed culture", also referred to herein as a co-culture, refers to a culture comprising at least two different species of bacteria, such as in the present context, a culture comprising bacteria of the species *A. wodanis* and *M. viscosa*. In such a mixed culture, the cells are cultured in a way that creates physical cell-cell contact between the cells of at least two species, e.g. *A. wodanis* and *M. viscosa*. It may also refer to a culture where one or more components extracted from *M. viscosa* or *A. wodanis*, or produced by recombinant gene technology from gene(s) of *M. viscosa* or *A. wodanis* cells, when added to a single culture of *A. wodanis* or *M. viscosa*, create the same impact on the *A. wodanis* cells or the *M. viscosa* cells as a mixed culture between the two species. A number of different cultures grown together or grown under impact from components of other cultures may be mixed together in a vaccine and/or a number of different strains.

Accordingly, a "mixed culture", also referred to herein as a co-culture, may also refer to a single culture of *M. viscosa* to which extracellular products from another mixed culture of *A. wodanis* and *M. viscosa* have been added, thereby providing an external influence on the single culture of *M. viscosa* which changes the physical appearance of the cell membrane bound structures or other antigens of *M. viscosa*. A "mixed culture" may be started off with a few cells of each species of *A. wodanis* and *M. viscosa* and then growth in the culture then occurs in a way ensuring that most cells of each species has been in physical contact with cells of the other bacterial species during propagation/growth of the culture.

A number of different single cultures of the different species may be mixed together in a vaccine and/or a number of different strains of the same bacterial species.

A "culture" includes all forms of culture, both in broth, on agar and in any other media like eukaryotic cell cultures, eukaryotic/animal/fish tissue within research animals or any other physical measure. The temperature and the salt concentration (e.g. NaCl) conditions for each culture can be determined separately, and depending on the circumstances and the materials used.

In the present context, examples of temperatures when said bacteria are cultured, but to which the invention is not limited, is referred to as "low" at about 7-8° C. and referred to as "high" at about 10-12° C., such as about 7, 8, 9, 10, 11 or 12° C. Temperature conditions may be selected as further described herein. "Low" may also refer to temperatures below 7° C. and "high" temperature may also refer to temperatures above 12° C.

The culture temperature is referring to the temperature used throughout. The cultures may be made in a temperature interval from +2° C. to 16° C. however a suitable temperature interval for growing cultures for producing antigens for the low temperature range is from 7 to 8° C. and for the high temperature interval 10 to 12° C.

The important switch in the bacterial antigenic outlook in both *A. wodanis* and *M. viscosa* occurs at about 9° C. in the sea water or laboratory culture. This means that for all the temperatures below 9° C. that support growth of these bacteria the low temperature outlook will occur on the bacterial cells of both species included herein. The same is relevant for growth at temperatures above 9° C. *A. wodanis* may grow from +25° C. to less than +4° C. and *M. viscosa* will grow from +21° C. and down to less than +4° C. Cultivation at temperature intervals of 7 to 8° C. and 10 to 12° C. for gaining the cold and warm antigenic outlook of the bacterial cells, respectively was selected as convenient and still functional in the included examples. Similarly salt concentrations other than +0.9° C. and +2.5° C. may be used to gain the high and low NaCl effect on the antigenic outlook of the bacteria. The switch is close to 1% NaCl.

A salt used herein may be a sodium salt, such as NaCl, or any other mineral mixture including marine salt. In the present context, examples of salt conditions are referred to as "low" when said concentration of salt is about 0.9% salt (which is similar to the salt concentration inside the fish body), and "high" when said concentration of salt is about 2 to 4% salt, such as about 2, 2.5, 3, 3.5 or 4% of salt (similar to the salt concentration in the marine water, a marine salt mixture may also be used), such as NaCl, and as further defined herein.

The concentration of salt is referring to the concentration of salt in the culture broth used from the start of the experiment.

When the term "about" is used herein, this refers to a deviation of the concentration, temperature or the like of about ±10%.

As an example, cultures of *A. wodanis* and *M. viscosa* may be made from the head kidney of diseased or dead fish or directly from ulcers or necrotic tissue from any place on or in the fish onto blood agar plates (Blood agar base 2, Difco) with about 5% cattle or sheep blood and 2.5 and 0.9% NaCl by a metal or plastic loop. The cultures are then plated secondary or blood agar plates with 2.5% NaCl and frozen in Luria broth with 2.5% NaCl and 10% glycerol in 1 ml plastic ampulles at −80° C. The frozen cultures may be restreaken at blood agar plates with 2.5% salt, such as NaCl, whenever needed. All plates may be cultivated at various temperatures from 8 to 12, such as at about 8, 9, 10, 11, or 12 degrees Celsius depending on the sea water temperature where the fish where sampled. Further suitable temperature intervals for culture of said bacteria are disclosed herein.

In the context of the present disclosure, it is further encompassed a composition comprising inactivated bacteria, wherein the bacteria of one or more single culture(s) and/or one or more mixed culture(s) have been cultivated at different temperature and salt conditions as mentioned herein, in response thereto generating a plethora of different antigenic compositions of the bacteria, which is suitable in the context of vaccines. Such inactivated bacteria originating from several single or mixed cultures may form a vaccine composition as disclosed herein.

An "adjuvant" is a pharmacological or immunological agent that modifies the effect of other agents, such as a drug or vaccine. An adjuvant may be included in a composition as defined herein to enhance the recipient's immune response to a supplied vaccine, while keeping the injected foreign material to a minimum. Examples of adjuvants are oil emulsions, such as Freunds Incomplete, and aluminium salts.

A "vaccine" as referred to herein, may refer to both a prophylactic and/or a therapeutic vaccine. A "vaccine", which is a term well-known in the art, is a biological preparation that improves immunity to a particular disease. Usually, a vaccine contains an agent that resembles a disease-causing microorganism, and is often made from weakened or killed forms of the microbe, its toxins or one or more of its surface proteins. The agent stimulates the body's immune system to recognize the agent as foreign, destroy it, and "remember" it, so that the immune system can more easily recognize and destroy any of these microorganisms that it later encounters.

A "pharmaceutically acceptable excipient" as referred to herein, refers to an optional component of the vaccine for instance one or more emulgators, which may facilitate the handling, storage and/or administration thereof, such as presenting the vaccine in a suitable form, e.g. as a gel or liquid, for administration. One example of an excipient used herein is standard PBS (Phosphate-buffered saline), but the invention is not limited thereto.

DETAILED DESCRIPTION

Hereby in this document for the first time ever in farmed fish such as salmonids, in particular Atlantic salmon (*Salmo salar* L.) and rainbow trout (*Oncorhynchus mykiss* L.), but also Atlantic cod (*Gadus morhua* L.) from North Atlantic coastal fish farms, a novel disease called wodanosis, is defined. The disease is characterized by septicemic infection resulting in ascites and often a mottled liver and swollen spleen and in prolonged cases fin rot typically on the bases of the tail fin and back fin. Typical outbreaks are occurring in the fish farms but more commonly a low level of mortality caused by wodanosis is occurring year round in most farms with Atlantic salmon. Highest mortalities in the farms caused by wodanosis is occurring in the spring, summer and autumn but also in winter months mortality is evident.

Hence, as shown herein, the present inventor has for the first time been able to illustrate the importance of the bacterium *Aliivibrio wodanis* in the herein identified pathogenic condition wodanosis, which is further described herein, as well as its role in winter ulcer. As previously mentioned, the bacterium *Aliivibrio wodanis*, described in parallel with *Montella viscosa* for the first time by Lunder (1992), Lunder et al. (1995) and Lunder et al. (2000) and later by Benediktsdòttir et al. (2000) was not until this date given any pathogenic relevance. However, herein it is provided the surprising finding that the bacterium *Aliivibrio wodanis* plays a significant role in the pathogenesis both of the established disease winter ulcer, in wodanosis as well as in a co-infection with the two bacteria causing wodanosis and winter ulcer also resulting in a chronic disease with extensive skin ulcers often with a prolonged disease development ending in septicemia and death later or sometimes fish may survive the co-infection because of the slower pathogenesis. This finding will contribute to the vaccine development for all these diseases, which is further shown herein and supported by vaccine experiments.

Strains of *A. wodanis* and *M. viscosa* used in the studies and experiments related to this disclosure are deposited at the Norwegian School of Veterinary Science and at the National Veterinary Institute, Oslo, Norway in addition to the type strain deposition at the NCIMB. It has been documented some strain variation among *M. viscosa* in a few studies lately (Grove et al. 2010) demonstrating variance related to both geography and fish host species. The strains disclosed in the present document are all publically available from the institute in addition to the type strains which may be obtained from ATCC, from CRBIP or from NCIMB, which is further referred to herein. Strains of use in the present disclosure have also been published, such as by Benediktsdottir et al (International Journal of Systematic and Evolutionary Microbiology, 2000). Further, the present disclosure is not limited to any particular strain of *Aliivibrio wodanis* or *Moritella viscosa*, but it is instead particularly useful to use any local isolated strain involved in an outbreak of wodanosis and/or winter ulcer.

Now, *Aliivibrio wodanis* has been shown to possess a virulent role in the acute stages of wodanosis, as well as in the chronic stages (co-infection resulting in chronic "winter ulcer") of winter ulcer and wodanosis due to its interaction with the bacterium *Montella viscosa*.

At temperatures from <6 to 8° C. it has been shown that *M. viscosa* is most clinically active and is aggressively attacking the skin of the fish directly creating small ulcers and in addition infecting the fish septicemically mainly through the gill epithelium (Løvoll et al. 2009, Karlsen et al. 2012). *M. viscosa* is not inhibited and phagocytized by the important scavenger system as part of the innate immune system of the skin constituted by the phagocytizing keratocytes (Malphigian cells). *A. wodanis* and other bacteria including most particulate material contaminating the skin surface is removed by the actively motile keratocytes that also normally starts healing wounds of the skin.

However, *A. wodanis* is early infecting the small ulcers created by *M. viscosa* and establish a co-infection together with *M. viscosa*. By physical contact between the two species of bacterial cells *A. wodanis* is modulating and reducing the virulence of *M. viscosa*, including down-regulation and inhibition of production of hemolysins and other toxins produced by *M. viscosa*. Even the cell-growth of *M. viscosa* is inhibited by *A. wodanis* at an early stage in the co-infection. *A. wodanis* is also down-regulating its own virulence in co-infection with *M. viscosa* in chronic "winter ulcer".

This inhibitory activity caused by *A. wodanis* is most prominent at salt concentrations around 0.9% and almost not visible at around 2.5 to 3% NaCl concentration. In the ulcers there seems to be a biofilm-like mucoid layer covering the ulcer surface. This biofilm-like layer is mostly dominated by a *Tenacibaculum* sp. bacterium that is difficult to cultivate (O'Halloran et al. 1991, Olsen et al. 2011) and that has been linked to ulcer pathogenesis only in Atlantic salmon with scarified skin. This biofilm-like layer is probably important in protecting the ulcerated fish from loss of body liquid caused by the osmotic power and death because of physiological "drought". Under this seal of a biofilm created by mostly *Tenacibaculum* sp. *M. viscosa* and *A. wodanis* is continuing its "slave-and-master" activity at a physiological salt concentration which enables *A. wodanis* to inhibit the virulence of *M. viscosa* in a way that prolongs the infection for weeks and months and that creates larger and larger ulcers extending to a high percentage of the skin surface. In challenge situations without *A. wodanis* involved *M. viscosa* is often aggressively killing the fish within a few days before the ulcer reach the extended size.

*M. viscosa* can also alone cause septicemic infections by using the gills as admission portal and is found in internal organs as a result (Karlsen et al 2012). In the field situation *A. wodanis* is in most cases co-infecting the fish septicemically together with *M. viscosa* and is down-regulating the virulence of *M. viscosa* and itself as in the ulcers, prolonging the life of infected individuals substantially.

At temperatures in sea-water from 9 to 10 degrees Celsius and higher *A. wodanis* is getting more aggressive as a pathogen in addition to performing the inhibitory control of the virulence factors in *M. viscosa* even more strictly while in parallel *M. viscosa* looses its virulence also as single species infectant at those warmer temperatures. At temperatures from 9° C. and up *M. viscosa* is not active in creating ulcers in the skin when *A. wodanis* is co-infecting. At these higher temperatures skin ulcers are relatively rarely observed and the winter ulcer disease is known to occur below 8° C. only.

However, ulcers are occurring at a relatively low frequency at these higher temperatures as part of the wodanosis disease caused by *A. wodanis* mostly in the form of depressions caused by necrosis in the skin at the base of the back fin and tail fins leading to loss of the fin and necrosis of the area around the fin base, also described as "fin rot".

In wodanosis the main pathological changes are created as a result of the septicemia caused by *A. wodanis*. However, still to some extent at these higher temperatures when *A. wodanis* is dominating the pathogenesis it is common to find *M. viscosa* together with *A. wodanis* in the head kidney and other internal organs of the infected fish. However, at these higher temperatures it seems that *M. viscosa* is not causing disease and is clearly inhibited by *A. wodanis* at physiological salt concentrations but not clearly at marine salt concentrations. The role of *M. viscosa* at higher water temperatures is important as a factor that makes *A. wodanis* to down-regulate its own virulence. Between the high and low end of the temperature range for wodanosis and winter ulcer, respectively, the two bacteria gradually switch the "working" roles in the "master-and-slave relation" resulting also in a switch between the clinical diseases wodanosis and winter ulcer, respectively.

During this switch between winter ulcer and wodanosis *A. wodanis* is all the time in control of the virulence of *M. viscosa* as the "master". Both bacteria are found in a balanced concentration often between 40 and 60% of the cells for each of them in the infected ulcers or internal organs in the whole temperature range. In the laboratory the temperature range for growth for both *A. wodanis* and *M. viscosa* is between 4 and 25° C., however *A. wodanis* is known to grow faster at temperatures around 12° C. than *M. viscosa* that grow relatively better at a lower temperature level (Lunder et al. 2000).

All together *A. wodanis* can control the winter ulcer development at all relevant temperatures but at low temperatures it needs to be ahead in time of *M. viscosa* to be able to down-regulate the virulence of *M. viscosa*. In addition the relative concentration levels between the two pathogens decide how strong the down-regulation of the pathogenesis of both *M. viscosa* and *A. wodanis* will be.

In the field both *A. wodanis* and *M. viscosa* is apparently ubiquitous in the sea-water but possibly at various concentration levels in the water column where the net pens with fish are located. This explains that both bacteria are found together in the major part of the outbreaks of winter ulcer (Lunder et al. 1995).

Accordingly, it is shown herein that various levels of winter ulcer and wodanosis in the fish farms are a result of both temperature and concentrations of *A. wodanis* and *M. viscosa* in the sea. Common to field outbreaks of both winter ulcer and wodanosis is the dominating tendency to chronic development of both diseases with a relatively low level of mortality that continues for weeks and months instead of occurring as dramatic outbreaks, a scenario that has been reproduced in the infection studies. At higher water temperatures in the spring the ulcers heal off leaving scar tissue.

The unique effects of the physical contact between bacterial cells of *A. wodanis* and *M. viscosa* result in a change of the outlook of both bacterial cells. Western blot studies herein demonstrate a dramatic difference in the proteins produced by *A. wodanis* and to almost the same extent for *M. viscosa* when the bacteria are grown in single cultures compared to a mixed culture of the two bacteria.

Physical contact between cells of the two bacteria in addition regulate down the production of virulence factors in both bacteria. The temperature is a key switch between the two diseases, winter ulcer and wodanosis even in the same fish individual during the chronic stages that may extend across seasons with changes in sea water temperature. At low temperature winter ulcer is allowed to develop often at a low speed and at higher temperature wodanosis is developing normally producing low or moderate mortality. This regulation of both the antigen outlook of the bacteria and the production of virulence factors is a direct result of direct cell-to-cell contact between the two pathogens a phenomenon well documented in bio-assays in the laboratory including eukaryotic cell cultures.

Accordingly, the cell-to-cell surface interactions between these two bacteria have herein been shown to cause a change of structural characteristics on the cell surface, in addition to a modified production panorama of various extracellular toxins decreasing the acute virulence of the bacteria, but instead facilitating prolonged disease by keeping the fish infected but alive.

Most outbreaks of winter ulcer are modulated to a chronic disease by the impact of *Alliivibrio wodanis* through cell-to-cell contact with *Moritella viscosa*. This down-regulation of virulence by *Alliivibrio wodanis* in *Moritella viscosa* is occurring by direct bacterial cell contact in the skin ulcers but also as direct contact in the internal organs of the fish during septicemia. The result is that instead of a relatively high mortality caused by *Moritella viscosa* as demonstrated under experimental conditions, the winter ulcer disease caused by *Moritella viscosa* is appearing as a chronic disease with extensive development of skin ulcers in a relatively high number of fish but with a relatively low mortality. The outbreaks of winter ulcer are prolonged with low mortality until the temperature is rising in the spring. Due to this fact, it is important that a vaccine against winter ulcer is effective against all stages of disease, not only preventing the initial acute phase.

With higher temperatures in spring and summer *Moritella viscosa* is not able to cause ulcers. However, *Alliivibrio wodanis* is continuously causing wodanosis mostly with a low mortality also in the spring, summer and autumn at higher temperatures. However, wodanosis is not always characterized by ulcers as in the disease winter ulcer in the winter period. Still, in view thereof, it is not enough to vaccinate against winter ulcer to avoid severe disease affecting the fish.

As shown herein wodanosis may also occur as outbreaks where *A. wodanis* is the only or dominating pathogen. Various predisposing factors may facilitate such outbreaks of wodanosis of which a common factor is fin rot occurring the first weeks after sea launch of the Atlantic salmon smolts. This fin rot is very often occurring as a melting down of the skin and underlying connective tissue starting from the fin tip and rapidly developing towards the fin base leaving the fin spine naked in the sea water. The tail fin and pectoral fins are most commonly affected by this type of fin rot but the pelvic fins, the anal fin and the back fin may also be affected. The great motility of the pectoral fins results in self-created skin damage when the tip of the rotten fins with the eroded spines is touching the scales and skin behind the fin base. At first the scales are physically removed by the sharp bony spines but at some point *A. wodanis* seems to infect the wounded skin and create a typical ulcer that relatively often ends with perforation into the abdomen with partly evisceration as a result in some cases. In addition to hurting themselves with the eroded sharp spines fish with fin rot may easily create small wounds in the skin of other fish in particular in a densely populated net pen or in a net pen with stress and disorganized swimming. As a result in an outbreak of wodanosis in smelts suffering from fin rot it is common to observe skin ulcers on all parts of the fish body making it difficult to separate ulcers from the two separate infections winter ulcer and wodanosis.

In addition to ulcers caused by spines of "rotten" fins it is common in wodanosis to observe infection and necrosis of the tip of the mandibula. This "jaw rot" may develop slowly but can also relatively rapidly develop into complete disappearance of all the soft tissue of the mandibula making it impossible for the fish to eat with a resulting loss of body weight. Also the upper jaw may be affected by ulcers that may develop to include larger parts of the head. However, this is far less common than rot in the mandibula (lower jaw). It seems that in crowded pens the smolts quite easy get small scratches on the tip of the mandibula probably during feeding or collision with net walls and other types of equipment.

As with other types of infections wodanosis may cause infection in the connective tissue surrounding one of the eyes. The result is swelling and less room for the eye in the scull. Often the infection attacks the eye bulb with a final puncture as the result.

During both spine initiated ulcers, mandibular infection and eye infection *A. wodanis* normally causes a septicemic infection that invariably is occurring when the fish is dying from wodanosis. The fin rot affections most often have a combined occurrence of *Tenacibaculum* sp and *A. wodanis*, but in some cases the necrotic tissue is dominated by *A. wodanis*. In general it seems that *A. wodanis* need predisposing damage in the skin before creating typical ulcers indistinguishable from winter ulcers caused by *M. viscosa* that seem to cause primary ulcers more actively.

Fin rot is not commonly occurring in Atlantic salmon after some months in the sea and it seems that wodanosis has an even but low morbidity during the rest of the production cycle in the sea.

Even if *Aliivibrio wodanis* and *Moritella viscosa* each can cause separate infections the two bacteria are almost as a rule physically occurring together in fish that have two separate infections in parallel, both chronically, and with *Aliivibrio wodanis* as the master down-regulator of the virulence including its own demonstrated in the two separate but still intimately related infections. *Moritella viscosa* is a skin ulcer causing bacterium in the cold winter months which is a feature not dominant in the double-infection in the summer months. However, in challenge *M. viscosa* alone is able to cause winter ulcer with typical skin lesions even at temperatures above 8° C., demonstrated in challenges up to 10-12° C. (Lunder et al. 1995). Most salmon, however, dies before extensive skin ulcers develop when *M. viscosa* is used as the sole challenging pathogen. In the warmer periods of the year wodanosis with a low occurrence of skin ulcers is causing mortality. However, year-round *Aliivibrio wodanis* and *Moritella viscosa* are occurring together in the diseased fish in a double infection mastered by *Aliivibrio wodanis*, In view thereof, there is a need to prevent infections by both bacteria to maintain healthy fish populations.

Lunder et al. 1995 cultivated bacteria from ulcers and kidney from salmon with winter ulcer in eight separate farms with a mortality due to winter ulcer from 0 to 2% per week. None of these farms had vaccinated against *M. viscosa* since the study was performed before any commercial vaccine was developed. Salmon with winter ulcer had been observed in the farms in a period varying from 2 to 5 months before sampling. The farms were located all along the coast of Norway and the temperature in the water when sampling varied between 4 and 8 degrees Celsius. This sampling of 169 salmon related to winter ulcer was at the time considered to be representing typical winter ulcer disease. However, the results show that *M. viscosa* was isolated without *V. wodanis* in 7% of the ulcers while *A. wodanis* was isolated without *M. viscosa* in 33% of the ulcers. The two bacteria were isolated together from 59% of the ulcers. The figures from the cultivation from the head kidney were 13, 34 and 28%, respectively. From salmon without ulcers *M. viscosa* were found alone in the kidney in 4% of the salmon while *A. wodanis* was found alone in 9% of the kidneys from salmon without ulcer. When both bacteria were found together in the kidney there were always ulcers in the skin. The results from this study probably represent the real distribution between winter ulcer and wodanosis in farmed Atlantic salmon even today in an unvaccinated population at temperatures from 4 to 8 degrees Celsius. It means that approximately every third salmon with ulcers is having wodanosis without connection to *M. viscosa* while only approximately every ten salmon with ulcers have winter ulcer caused by *M. viscosa* without relation to *A. wodanis*. Finally about six of ten salmon with ulcers have a co-infection with both *M. viscosa* and *A. wodanis*, meaning they have both real winter ulcer and wodanosis simultaneously in a very intimate pathogenesis. The reason why only 10% of the sampled salmon were shown to present real winter ulcer infection caused by *M. viscosa* only is possibly because salmon with pure winter ulcer caused by *M. viscosa* alone is having a more acute infection and will die faster than in salmon with a co-infection as is demonstrated in bath infections with *M. viscosa*. This indicates that fish with wodanosis at these low temperatures have an intermediate mortality between winter ulcer and a co-infection of both pathogens that is having a chronic development in most cases. This hypothesis is supported by the fact that only half the salmon with infection with *M. viscosa* alone had developed ulcers while all salmon with wodanosis had developed ulcers. In contrast to this fact two thirds of the fish with ulcers had a co-infection with both pathogens in the ulcers but only half of these salmon had developed septicemia with both the pathogens established in the head kidney. This supports the results demonstrating that the co-infection of winter ulcer and wodanosis slows down the development of the pathogenesis drastically making the outbreaks less acute and more prolonged leaving many diseased salmon to survive when the water temperature rises and additionally reduces the virulence of *M. viscosa*.

Lunder et al. 1995 made a nice study with clearly representative results from unvaccinated farm populations which is verified by the observations made and the fish experiments performed to support this application. However, the authors erroneously concluded that *A. wodanis* had no active role in the pathogenesis of the ulcer disease studied and originally called winter ulcer clinically at the time. The reason for this conclusion was mainly that the authors were not able to reproduce infection by challenging Atlantic salmon with *A. wodanis*. Because of this the commercial vaccine companies included only *M. viscosa* to protect against "winter ulcer". This mistake has resulted in only approximately 60% protection against ulcers in farmed Atlantic salmon. Other scientific authors have also made the same mistake (Greger and Goodrich 1999) and the vaccine producer Pharmaq AS while using *A. wodanis* in a commercial autogenic vaccine against both winter ulcer and atypical furunculosis on Iceland from 1992 to 1995 (Thorarinsson et al. 2003). The conclusion was that *A. wodanis* did not contribute to the protection of salmon against ulcer disease. The reason for this conclusion is most probably because the vaccine was not properly made technically as shown in this application. However, it may also be that *A. wodanis* was not contributing markedly to increased disease development but rather to a reduced speed in the disease development when in a co-infection with *M. viscosa* at sea temperatures between 4 and 8 degrees Celsius. Co-infections with *M. viscosa* and *A. wodanis* were occurring regularly and that apparently was the case on Iceland. *A. wodanis* is low-virulent below 8 degrees Celsius when it is in co-infection with *M. viscosa*, it is merely functioning in reducing the virulence of *M. viscosa* in the co-infected salmon at these temperatures. As shown in the studies presented in this application the inclusion of *A. wodanis* in the autogenic vaccine without proper preparation of the vaccine cultures and correct construction of the antigen mix may have increased the virulence of *M. viscosa* in co-infected salmon by "strangling" *A. wodanis*, the master down-regulator of *M. viscosa* virulence, by directing increased immune defense against *A. wodanis*. In particular this may have been the case in the period from 1992 to 1993 when only *A. wodanis* were included in the combination vaccine with atypical *A. salmonicida*. However, even after including *M. viscosa* in the vaccine the effect of having *A. wodanis* included in the vaccine may have been in total negligible or even negative without proper preparation of the vaccine contents.

As a summary it may be stated that the study design of the field sampling in Lunder et al. 1995 was close to optimal and the results are excellent for a correct conclusion but because Koch's postulates were not fulfilled for *A. wodanis* in the hands of the authors as much as between 10 and 20% loss of cultured Atlantic salmon in sea in most Atlantic salmon producing countries caused by wodanosis in almost 20 years is the cost of the erroneous conclusions. It may be said that even if Koch's postulates should have been fulfilled by Lunder et al. 1995 the major vaccine company manufacturing fish vaccines at the time in cooperation with a leading research group on winter ulcer were not able to create an effective vaccine against wodanosis. In fact their experience and conclusions from the inclusion of *A. wodanis* in winter ulcer vaccines cemented the mistaken conclusions drawn from winter ulcer studies at the time. Knowing what is probably the major parts of the intricate complexity of the intimate interplay between the two major actors of ulcer disease in salmon and some other fish species (*A. wodanis* and *M. viscosa*) it is understandable why it took 25 years to unravel the secrecies of the "warrior" (*M. viscosa*)—"master" (*A. wodanis*)—relation of these important fish pathogens.

In summary and in view of the surprising findings discussed in the above, it is now possible to produce vaccine compositions which are optimized for the treatment and/or prevention of winter ulcer, wodanosis or a co-infection of both diseases, wherein said vaccine compositions comprises inactivated bacteria obtained from one or more single and/or mixed cultures of *Aliivibrio wodanis* and *Moritella viscosa*. A vaccine composition enabling an as complete protection as possible against wodanosis and winter ulcer may be obtained by preparing a vaccine comprising inactivated bacteria obtained from one or more single culture(s) of *A. wodanis* and *M. viscosa*, as well as one or more mixed culture(s) of these bacteria wherein the cultures may be prepared by growing the bacteria at all possible combinations of high and low temperature and salt conditions as disclosed elsewhere herein. One strain of each bacterium may be cultured. Also, it is to be understood, that by selecting the strains of *A. wodanis* and/or *M. viscosa* according to the strains most prevalent in the area where the fish are to be grown, a better protection is obtained. A vaccine composition mainly protecting against wodanosis may be prepared by growing bacteria at a high temperature and a low salt concentration, such as at about 10° C. and 0.9% salt. A vaccine composition mainly protecting against wodanosis may also be prepared by growing bacteria at both a high and low temperature and a high and low salt concentration, such as at about 10 and 8° C. and 2.5 and 0.9% salt. A vaccine composition mainly protecting against winter ulcer may be prepared by growing bacteria at a low temperature and a high salt concentration, such as at about 8° C. and 2.5% salt. However, as mentioned above, a very good disease protection is obtained by mixing one or more single and one or more mixed culture(s) of the bacteria grown at different salt and temperature conditions as disclosed elsewhere herein.

Hence, to prevent and/or treat the chronic stages of the two diseases, it is envisaged a composition comprising inactivated bacteria of one or more mixed culture(s) of *Aliivibrio wodanis* and *Moritella viscosa*, providing an immunogen which is different to inactivated bacteria when they have been cultured as single cultures, thereby having different immunogenic properties.

Accordingly, for the acute stages of wodanosis, a composition comprising inactivated bacteria of one or more single culture(s) of *Alliivibrio wodanis* is particularly useful, which can then be complemented with inactivated bacteria of one or more mixed culture(s) of *Alliivibrio wodanis* and *Moritella viscosa* for the chronic stages of the disease.

Hence, further envisaged herein is a complement to an existing vaccine for winter ulcer, which complement comprises a composition of inactivated bacteria of one or more mixed culture(s) of *Alliivibrio wodanis* and *Moritella viscosa* to prevent and/or treat the chronic stage pathogenesis of winter ulcer. Accordingly, encompassed by the present disclosure is a vaccine composition comprising inactivated bacteria of one or more mixed culture(s) of *Alliivibrio wodanis* and *Moritella viscosa*, which can be prepared according to a method as disclosed herein. This will be a suitable way of combating chronic disease as it has now been shown that *Alliivibrio wodanis* is able to down-regulate the virulence and pathogenicity of the bacterium *Moritella viscosa* that is causing winter ulcer, changing the appearance thereof. Such a composition can form a separate vaccine, or complement an already existing vaccine for winter ulcer. It can also form a separate vaccine component of a vaccine directed to wodanosis.

Such one or more single and/or mixed cultures may be cultured at different salt and temperature conditions to optimize the antigenic appearance of the vaccine which is further described herein.

Accordingly, it is related to herein, inactivated bacteria of spp. *Aliivibrio wodanis* (*A. wodanis*) for medical use. Hence, the present disclosure relates to a composition comprising inactivated bacteria of spp. *Aliivibrio wodanis* (*A. wodanis*) for medical use. Said composition may comprise inactivated bacteria of one or more single culture(s) of *A. wodanis*. It is also related herein to a composition which comprises inactivated bacteria of one or more mixed culture(s) of spp. *A. wodanis* and *Moritella viscosa* (*M. viscosa*) for medical use, and which optionally further comprises inactivated bacteria of one or more single culture(s) of *A. wodanis*. It is also related to herein a composition which comprises inactivated bacteria of one or more single culture(s) of *A. wodanis*, inactivated bacteria of one or more mixed culture(s) of *A. wodanis* and *M. viscosa* and inactivated bacteria of one or more inactivated single culture(s) of *M. viscosa*, for medical use. In addition, it is also related to a composition which comprises inactivated bacteria of one or more single culture(s) of *A. wodanis*, and inactivated bacteria of one or more single culture(s) of *M. viscosa*, for medical use. Furthermore, it is also related to a composition which comprises inactivated bacteria of one or more mixed culture(s) of spp. *A. wodanis* and *M. viscosa* and inactivated bacteria of one or more single culture(s) of *M. viscosa*, for medical use.

Inactivated bacteria obtained from single culture of *A. wodanis* and *M. viscosa* may also have a vaccinating effect in the primary stages of the pathogenesis of the co-infection between *A. wodanis* and *M. viscosa* before the two bacteria have come into direct cell-to-cell contact on or in the host and because of that changed the cellular antigenic outlook.

Inactivated bacteria originating from the single culture is mostly useful for providing the vaccinating effect for wodanosis (caused by *A. wodanis* alone) and winter ulcer (caused by *M. viscosa* alone) acute primary stages of disease.

Without wishing to be bound by theory, it may be possible that one or more antigens expressed when *A. wodanis* and *M. viscosa* are grown in single cultures may enlarge the vaccinating effect caused by the co-cultured bacteria, an effect that is not the same as seen as a result of co-cultured bacteria, and vice versa.

Whenever a "composition" is referred to herein, this refers to a bacterial composition as identified in the above, or as otherwise exemplified herein, containing the different combinations of inactivated bacteria obtained from one or more single and/or mixed bacterial culture(s) of *A. wodanis* and/or *M. viscosa*, and/or one or more components and/or antigenic part(s) thereof, as further defined herein, even though every combination of inactivated bacteria is not explicitly mentioned in every aspect or in every use thereof. Accordingly, inactivated bacteria of *A. wodanis* and/or *M. viscosa* originating from one or more single and/or mixed culture(s), which may be prepared during different temperature and salt conditions as disclosed herein, and/or one or more components and/or antigenic part(s) thereof as further defined herein can be combined in all aspects as clarified herein, and as further supported by the claims.

Accordingly, there is provided herein a composition comprising inactivated bacteria as defined herein wherein said inactivated bacteria have been obtained from one or more mixed and/or single culture(s) of *A. wodanis* and/or *M. viscosa* which has/have been cultivated at a temperature of about 10-12° C. (high), such as at about 10, 11 or 12° C.

Further, there is provided herein a composition comprising inactivated bacteria as defined herein, wherein said inactivated bacteria have been obtained from one or more mixed and/or single culture(s) of *A. wodanis* and/or *M. viscosa* which has/have been cultivated at a temperature of about 7-8° C. (low), such as about 8° C. There is also provided herein a composition as defined herein comprising inactivated bacteria wherein said inactivated bacteria have been obtained from one or more mixed and/or single culture(s) of *A. wodanis* and/or *M. viscosa* which has/have been cultivated at a salt, such as a sodium salt, e.g. NaCl, concentration of about 0.9% (low). There are also provided combinations thereof. In addition, there is provided a composition comprising inactivated bacteria as defined herein, wherein said inactivated bacteria have been obtained from one or more mixed and/or single culture of *A. wodanis* and/or *M. viscosa* which has/have been cultivated at a salt, such as a sodium salt, e.g. NaCl, concentration of about 2.5% (high). Such compositions may be used as a vaccine composition, such as for the use in the prevention and/or treatment of wodanosis and/or winter ulcer, whichever suitable depending on the temperature in sea water which is further explained herein.

Examples of strains of *A. wodanis* and/or *M. viscosa* that may be used in the context of the present disclosure provided herein are the commercially available type strains (NVI 88/478[1], *M. viscosa*, NVI 88/441[T], *Aliivibrio wodanis*,) as well as the reference strains *M. viscosa* (NVI 06/09/139-Ft 5427 (NCIMB accession number 42122)) and *A. wodanis* (NVI 06/09/139 Ft 5426 (=NCIMB accession number 42121)), but is not limited thereto.

It also refers to a composition, comprising the combinations of inactivated bacteria prepared from one or more single and/or mixed culture(s) of *A. wodanis* and/or *M. viscosa* which have been obtained through a method for preparing one or more bacterial composition(s) as described herein.

A composition comprising inactivated bacteria as described herein can further comprise an adjuvant, and/or a pharmaceutically acceptable excipient.

In addition to the inactivated bacteria, and/or one or more components and/or antigenic part(s) thereof and/or adjuvants in a vaccine composition, emulgators may be added, such as highly refined polyoxyethylenesorbitan and sorbitan oleates, such as polysorbate 85, polysorbate 80, PEG-6 sorbitan oleate, and sorbitan oleate etc. Emulgators are added to stabilize the vaccine emulsion in particular when mineral oils are added as adjuvant. When oil-in-water or water-in-oil emulsions are made they may be instable if not used soon after. It is also possible to instead if adding an external emulgator, to emulgate mechanically and use the vaccine the same day as it is prepared. For vaccines that need to be stored, emulgators are added often in a mixture of up to typically 3 to 4 in accordance with procedures known to the manufacturer. A successful emulgator-mix makes it possible to store the vaccine effectively for a longer period. Typically from 5% and up to 10 or 12% emulgator can be part of a commercial vaccine composition. However, methods and means for preparing a vaccine composition suitable for storage are well known for the skilled practitioner within this field.

Vaccine components may be in liquid form both as hydrophilic and lipophilic, which phased may often then be mixed in emulsions that need to be stabilized for storage. Examples may be found in Roar Gudding (Editor) et al. "Fish Vaccinology", Developments in Biological Standardization, 484 sider.

In addition, dry vaccines may also be prepared from the compositions as disclosed herein, and then dissolved before usage. This is particularly for, dip, bath or oral vaccines that are not using oil adjuvants or similar.

Encompassed by the present invention is also a composition comprising inactivated bacteria of spp. *Aliivibrio wodanis* (*A. wodanis*), such as one or more single culture(s) thereof, for use as a vaccine, such as a vaccine for the treatment and/or prevention of wodanosis and/or for the treatment and/or prevention of winter ulcer, said composition comprising, or further comprising, inactivated bacteria of one or more mixed culture(s) of spp. *A. wodanis* and *Montella viscosa* (*M. viscosa*), and/or inactivated bacteria of one or more single culture(s) of *M. viscosa*. Accordingly, it is related to herein a composition comprising one or more single culture(s) of *Aliivibrio wodanis* (*A. wodanis*) and one or more mixed culture(s) of spp. *A. wodanis* and *Moritella viscosa* (*M. viscosa*) for use as a vaccine and for use in the treatment and/or prevention of wodanosis. Such a composition may also be useful in the treatment and/or prevention of winter ulcer. Further comprised herein is a composition comprising inactivated bacteria of one or more mixed culture(s) of spp. *A. wodanis* and *Moritella viscosa* for use as a vaccine, such as a vaccine for the treatment and/or prevention of wodanosis and/or for the treatment and/or prevention of winter ulcer.

As wodanosis and winter ulcer may occur as a co-infection depending on the temperature of the sea water and occurrence of the bacteria in sea-water, combinations of the above compositions are useful in the treatment and/or prevention of these conditions.

In addition, it is also related to a composition which comprises inactivated bacteria, wherein said inactivated bacteria are selected from the group consisting of bacteria of one or more single culture(s) of *A. wodanis* and *M. viscosa*, one or more mixed culture(s) of *A. wodanis* and *M. viscosa*, and/or a combination thereof, as further defined herein, for medical use, such as for use as a vaccine, e.g. in the treatment and/or prevention of wodanosis and/or winter ulcer. It is to be understood that such a composition can further comprise adjuvants and other components suitable to use in a vaccine composition.

A composition as defined herein may also be used in the manufacture of a vaccine and/or a medicament, such as in the manufacture of a medicament and/or a vaccine for use in the treatment and/or prevention of wodanosis and/or winter ulcer. A composition for use as a vaccine may also be referred to as a vaccine composition herein.

Accordingly, comprised herein is e.g. the use of a composition which comprises inactivated bacteria of spp. *Aliivibrio wodanis* (*A. wodanis*), such as inactivated bacteria of one or more single culture(s) of *A. wodanis*, comprising, or further comprising inactivated bacteria of a mixed culture of spp. *A. wodanis* and *Moritella viscosa* (*M. viscosa*), optionally further comprising inactivated bacteria of one or more single culture(s) of *M. viscosa*, in the manufacture of a medicament for the treatment and/or prevention of wodanosis, or in the manufacture of a medicament for the treatment and/or prevention of winter ulcer.

Accordingly, it is related to herein a composition comprising all components described in the above, for use as a vaccine, for use in the treatment and/or prevention of winter ulcer or wodanosis or a co-infection of the disease states.

Hence, the present disclosure relates to a composition which comprises any combination(s) of inactivated bacteria obtained from a single and/or mixed cultured in accordance with the above conditions. Such cultures may contain inactivated bacteria obtained from one or more culture(s) or strain(s) of the respective *A. wodanis* and *M. viscosa*

The purpose of using inactivated bacteria from a variety of cultures in the preparation of a vaccine as presented herein is to obtain an antigenic variance of the inactivated bacteria of the vaccine which is due to that the physical appearance and virulence of *A. wodanis* and *M. viscosa*, respectively, changes when the sea water temperature changes. This surprising finding revealed the importance of mirroring such varieties in vaccine preparations for these conditions.

As further mentioned herein, different salt concentrations and temperatures may be used when culturing bacteria for preparing a vaccine composition comprising inactivated bacteria with an optimal antigenic appearance for the respective disease state that is to be treated.

Examples of culture conditions that may be used for preparing cultures with different antigenic appearance, which may then be used in the present context is a composition comprising inactivated bacteria obtained from:

one or more mixed culture(s) of *A. wodanis* and *M. viscosa* using high salt concentration and high temperature, one or more mixed culture(s) of *A. wodanis* and *M. viscosa* using high salt concentration and low temperature, one or more mixed culture(s) of *A. wodanis* and *M. viscosa* using low salt concentration and high temperature, one or more mixed culture(s) of *A. wodanis* and *M. viscosa* using low salt concentration and low temperature, one or more single culture(s) of *A. wodanis* using high salt concentration and high temperature, one or more single culture(s) of *A. wodanis* using high salt concentration and low temperature, one or more single culture(s) of *A. wodanis* using low salt concentration and high temperature, one or more single culture(s) of *A. wodanis* using low salt concentration and low temperature, one or more single culture(s) of *M. viscosa* using high salt concentration and high temperature, one or more single culture(s) of *M. viscosa* using high salt concentration and low temperature, one or more single culture(s) of *M. viscosa* using low salt concentration and high temperature and/or one or more single culture(s) of *M. viscosa* using low salt concentration and low temperature, or a combination thereof. A composition comprising all components may be particularly suitable for treating and/or preventing both winter ulcer and/or wodanosis.

A further example is a composition comprising inactivated bacteria obtained from one or more of the following:

one or more single culture(s) of *M. viscosa* cultivated at about 8 degrees Celsius and at about 0.9% NaCl, one or more single culture(s) of *M. viscosa* cultivated at about 8 degrees Celsius and at about 2.5% NaCl, one or more single culture(s) of *A. wodanis* cultivated at about 10 degrees Celsius and at about 0.9% NaCl, one or more single culture(s) of *A. wodanis* cultivated at about 10 degrees Celsius and at about 2.5% NaCl, one or more mixed culture(s) of *M. viscosa* and *A. wodanis* cultivated at about 8 degrees Celsius and at about 0.9% NaCl, one or more mixed culture(s) of *M. viscosa* and *A. wodanis* cultivated at about 8 degrees Celsius and at about 2.5% NaCl, one or more mixed culture(s) of *M. viscosa* and *A. wodanis* cultivated at about 10 degrees Celsius and at about 0.9% NaCl, one or more mixed culture(s) of *M. viscosa* and *A. wodanis* cultivated at about 10 degrees Celsius and at about 2.5% NaCl, or a combination thereof. A composition comprising all components may be particularly suitable for treating and/or preventing both winter ulcer and/or wodanosis.

For use in the treatment and/or prevention of winter ulcer there is provided herein a composition which is particularly suitable therefore comprising inactivated bacteria of one or more single culture(s) of *M. viscosa*, inactivated bacteria of one or more mixed culture(s) of *A. wodanis* and *M. viscosa* and optionally inactivated bacteria of one or more single culture(s) of *A. wodanis*. A further suitable composition for use in the treatment and/or prevention of winter ulcer comprises inactivated bacteria obtained from one or more single culture(s) of *M. viscosa* cultured at a low temperature, such as about 8° C. and at a high salt concentration, such as about 2.5% salt, such as a sodium salt, such as NaCl, inactivated bacteria of one or more mixed culture(s) of *A. wodanis* and *M. viscosa* cultured at a low temperature, such as at about 8° C. and at high salt concentration, such as at about 2.5% salt, such as a sodium salt, such as NaCl, and optionally inactivated bacteria of one or more single culture(s) of *A. wodanis* cultured at a low temperature, such as at about 8° C. and at high salt concentration, such as about 2.5% salt, such as sodium salt, such as NaCl. When such a composition also comprises inactivated bacteria obtained from one or more single culture(s) of *A. wodanis* cultured at a low temperature, such as about 8° C., such a composition is also useful for the treatment and/or prevention of wodanosis or a co-infection of wodanosis and winter ulcer as *A. wodanis* may be active also at lower temperatures which is further described herein.

For use in the treatment and/or prevention of wodanosis there is provided herein a composition which is particularly suitable therefore comprising inactivated bacteria obtained from one or more single culture(s) of *A. wodanis*, inactivated bacteria obtained from one or more mixed culture(s) of *A. wodanis* and *M. viscosa* and optionally inactivated bacteria obtained from one or more single culture(s) of *M. viscosa*. A further suitable composition for use in the treatment and/or prevention of wodanosis is a composition comprising inactivated bacteria obtained from one or more single culture(s) of *A. wodanis* cultured at high temperature, such as about 10° C., and at low salt concentration, such as at about 0.9% salt, such as a sodium salt, such as NaCl, one or more mixed culture(s) of *A. wodanis* and *M. viscosa* cultured at high temperature, such as at about 10° C. and at a low salt concentration, such as at about 0.9% salt, such as a sodium salt, such as NaCl, and optionally one or more single culture(s) of *M. viscosa* cultured at a high temperature, such as about 10° C. and at low salt concentration, such as about 0.9% salt, such as a sodium salt, such as NaCl.

There is further provided herein a composition suitable for use as a vaccine for the treatment and/or prevention of a co-infection of winter ulcer and wodanosis which comprises inactivated bacteria obtained from:

a) one or more single culture(s) of *M. viscosa* cultured at low temperature, such as about 8° C., and at low salt concentration, such as about 0.9% salt, such as a sodium salt, such as NaCl, b) one or more single culture(s) of *M. viscosa* cultured at low temperature, such as about 8° C., and at high salt concentration, such as about 2.5% salt, such as a sodium salt, such as NaCl, c) one or more single culture(s) of *A. wodanis* cultured at high temperature, such as about 10° C., and at low salt concentration 0.9%, such as a sodium salt, such as NaCl, d) one or more single culture(s) of *A. wodanis* cultured at high temperature, such as about 10° C., and at high concentration, such as about 2.5% salt, such as a sodium salt, such as NaCl, e) one or more mixed culture(s) of *M. viscosa* and *A. wodanis* cultured at low temperature, such as about 8° C., and at low salt concentration, such as about 0.9% salt, such as a sodium salt, such as NaCl, f) one or more mixed culture(s) of *M. viscosa* and *A. wodanis* cultured at low temperature, such as about 8° C., and at high salt concentration, such as about 2.5% salt, such as a sodium salt, such as NaCl, g) one or more mixed culture(s) of *M. viscosa* and *A. wodanis* cultured at high temperature, such as about 10° C., and at low salt concentration, such as about 0.9% salt, such as a sodium salt, such as NaCl, h) one or more mixed culture(s) of *M. viscosa* and *A. wodanis* cultured at high temperature, such as about 10° C., and at high salt concentration, such as about 2.5%, such as a sodium salt, such as NaCl, and optionally i) one or more single culture(s) of *A. wodanis* cultured at low temperature, such as about 8° C., and at high salt concentration, such as about 2.5% salt, such as a sodium salt, such as NaCl, and further optionally j) one or more single culture(s) of *A. wodanis* cultured at low temperature, such as about 8° C., and at low salt concentration, such as about 0.9%, such as a sodium salt, such as NaCl, and further optionally k) one or more single culture(s) of *M. viscosa* cultured at high temperature, such as about 10° C., and at high salt concentration, such as about 2.5% salt, such as a sodium salt, such as NaCl, and further optionally l) one or more single culture(s) of *M. viscosa* cultured at high temperature and at low salt concentration, such as about 0.9% salt, such as a sodium salt, such as NaCl.

The last composition comprising *A. wodanis* cultured at a low temperature (° C.) is particularly suitable when to treat and/or prevent wodanosis occurring when the sea water comprises lower temperatures, such as further explained herein.

There is further provided herein the use of the compositions as a vaccine for the manufacture of a medicament for the treatment and/or prevention of winter ulcer and/or wodanosis, as applicable, or the use of any of the compositions in the manufacture of a vaccine for the treatment and/or prevention of winter ulcer and/or wodanosis, as applicable.

Further comprised herein is a method for preparing one or more composition(s) of inactivated bacteria as defined herein, comprising the steps of: a) separately cultivating one or more single culture(s) of *A. wodanis*, and/or one or more mixed culture(s) of *A. wodanis* and *M. viscosa* and optionally one or more single culture(s) of *M. viscosa*, b) inactivating bacteria of the culture(s) from step a), c) optionally combining the separate cultures of inactivated bacteria of step b) into one or more composition(s), and d) preparing one or more composition(s) of inactivated bacteria from one or more culture(s) of step b) or from one or more of the composition(s) of step c). Furthermore, in said method, an additional step may be performed before step b) wherein in said step, to one or more single culture(s) of bacteria of *A. wodanis* or *M. viscosa* cultivated in step a) extracellular products obtained from one or more mixed culture(s) with bacteria of *M. viscosa* and *A. wodanis* is/are added to single culture. The cultures used for preparing one or more composition(s) of inactivated bacteria may be any of the cultures exemplified herein, wherein different temperature and/or salt concentrations have been used to obtain compositions which are suitable for treating and/or preventing the disease states which may vary depending on sea temperature which is further described herein.

The cultivation of bacteria in step a) may be performed at a low temperature of about 7-8° C., such as about 8° C. or a high temperature such as about 10-12° C. and/or using a low salt concentration in said culture of about 0.9% salt or a high concentration of about 2 to 4% salt, such as about 2.5%. Said salt may be a sodium salt such as NaCl or any other equally suitable salt as natural marine salt or any artificial marine salt preparation. It is important to include the sodium component of any salt mixture. The medium used may be a regular laboratory medium as for cultivating bacteria, liquid media as broth (for instance Luria broth) for cultivating bacteria in suspensions or solid media added agar (for instance Luria agar, blood agar or similar) meant for cultivating bacteria in colonies.

After cultivation the bacterial cells may be collected by being spun down or filtered off from the medium, and thereafter washed in a buffer, such as a PBS buffer, inactivated and thereafter mixed directly with an adjuvant, if applicable, and for storage, an emulgator.

Inactivation of said bacteria in step c) may be performed by typically adding formalin to said one or more culture(s), such as about 1% formalin to said culture(s) for two hours at about 4° C. before washing the killed bacteria, keeping the cultures at a temperature above 30° C. for a time period sufficient for inactivating the bacteria, and/or by attenuating said bacterial culture(s), such as by repeated cultivations with or without mutagenic chemicals in the culture, by radiation or any other relevant measure until random mutations occur in one or more genes relevant for a successful pathogenesis. Alternatively attenuation of the bacteria by directed knock-out mutations of one or more of the virulence genes is performed. Normally formalin is used for inactivating bacteria included in vaccine preparations. However, formalin is considered to be an active denaturing agent of proteins resulting in discrepancy between the acquired immunological memory based on denatured bacterial surface proteins and the natural proteins of the pathogen approaching the host. This "blurred" image of the pathogen may be sharper by inactivating the bacterial cells prepared for the vaccine by a temperature above the level these psychrophilic bacteria can survive but still below the temperature when the bacterial proteins denaturate by heat, typically above 40-42° C., but the inactivation method is not limited to these conditions. This principle of inactivation is an example of an elegant way of inactivating psychrophilic bacterial pathogens for vaccine preparation. The same sharp immunological memory image of the outlook of the pathogen is also acquired by inactivating the bacteria by radiation or chemicals degrading specifically the nucleic acids. When this is noted there are studies indicating in general that formalin-killed bacteria may be stronger antigens and thereby causing a better immune reaction than the natural antigens. Therefore formalin may be an alternative component of said vaccine preparations for this reason.

Heat may also be used as an inactivation method, such as by heating said one or more culture(s) to about 30° C. for about 16 hours. The heat inactivation with relatively low temperature keeps the antigens natural without being denatured, and is therefore particularly useful in the present context. An example of a heat inactivation procedure for inactivating bacteria comprises growing vaccine cultures to late logarithmic phase and inactivation by heating the cultures to about 30° C. for about 16 hours without emptying the cultures from the culture flasks and without adding any extra component(s). After such a heat inactivation at 30° C. the viability of the cultures may be controlled by cultivation on blood agar plates with 2.5% and 0.9% salt, such as NaCl before the cells are spun down and washed (e.g. in Phosphate Buffered Saline, PBS) Thereafter, such heat inactivated bacteria are used directly in a vaccine preparation as provided herein, a method wherein the inactivation is performed by adding heat, such as by heating the cultures to about 30° C. for about 16 hours.

It is also related to herein any composition which is obtainable by, or obtained by, the present method, as well as to a medical use of such a composition. Also comprised herein is the use of the composition of inactivated bacteria obtained by the method as a vaccine, as well as in the manufacture of a vaccine. Said composition obtainable, or obtained by, by said method can also be used in the treatment and/or prevention of wodanosis, as well as in the manufacture of a medicament for the treatment and/or prevention of wodanosis. Said composition obtainable by, or obtained by, said method can also be used in the treatment/and or prevention of winter ulcer, as well as in the manufacture of a medicament for the treatment/and or prevention of winter ulcer.

Comprised herein is further a method for preventing and/or treating wodanosis in a fish, comprising administering an effective amount of one or more composition(s) comprising inactivated bacteria as defined herein, and/or one or more composition(s) which has been obtained by a method presented herein to a fish, which amount is sufficient to trigger an immune response in said fish. The amount of composition that is to be administered is typically in the range of about 0.2 to 0.05 milliliter (ml) for intraperitoneal application, but is not limited thereto. For dip or bath vaccination the vaccine is diluted in the water body where the fish is left either anaesthetized (dip) for a short period of less than a minute or swimming (bath) for a longer period up to one hour.

In addition, it is comprised herein a method for preventing and/or treating winter ulcer in a fish, comprising administering an effective amount of one or more composition(s) comprising inactivated bacteria as defined herein, and/or one or more composition(s) which has been obtained by a method presented herein to a fish, which amount is sufficient to trigger an immune response in said fish. The amount of composition that is to be administered is typically in the range of about 0.2 to 0.05 milliliter (ml) for intraperitoneal application, but is not limited thereto. For dip or bath vaccination the vaccine is diluted in the water. For the oral vaccination the vaccine may be included in the fish feed.

In a method as described herein any fish may be treated, which fish has been affected by the disease. Suitable fish may for example be salmonids (Salmonidee), e.g. salmon, Atlantic salmon, or rainbow trout or other fish species as Atlantic cod, turbot and cleaner fish, including five species of wrasse (Labridae), used on fish farms in Norway and to a lesser extent in Scotland, Shetland and Ireland to control infestation with sea lice.

When a fish is vaccinated with a composition as defined herein, this may e.g. be performed by intraperitoneal injection, by bath vaccination (see example e.g. in Løvoll, M., 2009), or by oral vaccination, but is not limited thereto. For dip or bath vaccination the vaccine is diluted in the water body where the fish is left either anaesthetized (dip) for a short period of less than a minute or swimming (bath) for a longer period up to one hour. For the oral vaccination the vaccine may be included in the fish feed once or repeatedly at boostering intervals.

Also encompassed herein is a composition comprising inactivated bacteria of spp. *M. viscosa* for use in the treatment of wodanosis, e.g when said inactivated bacteria originates from one or more single culture(s) of *M. viscosa*, which has been explained herein. It also relates to the use of a composition comprising inactivated bacteria of spp. *Moritella viscosa*, e.g. one or more single culture(s) of *M. viscosa* for the manufacture of a medicament for the treatment and/or prevention of wodanosis.

Furthermore, it is disclosed herein a kit for vaccinating fish, said kit comprising one or more composition(s) of inactivated bacteria as defined herein, means for handling said composition(s) and optionally instructions for use. Said means for handling said composition(s) may e.g. be a plastic or other relevant container meant for refilling automated syringes handled manually by vaccinators or for use in robotic devices used for injection of the anaesthetized fish, container with composition meant for preparing working solutions for bath or dip vaccination or tube, prefilled syringes for performing intraperitoneal injection etc, fish feed or similar prepared with the composition intended for oral application but is not limited thereto. Said instructions for use may refer to a method for treating and/or preventing wodanosis and/or winter ulcer, as disclosed herein, including e.g. the amount of vaccine preparation that is to be used.

Encompassed herein is also a vaccine composition comprising inactivated bacteria of spp. *Aliivibrio wodanis* (*A. wodanis*), which composition may comprise inactivated bacteria of one or more single culture(s) of *A. wodanis*. It is also related to herein a vaccine composition which comprises inactivated bacteria of one or more mixed culture(s) of spp. *A. wodanis* and *Montella viscosa* (*M. viscosa*), and which optionally further comprises inactivated bacteria of one or more single culture(s) of *A. wodanis*. It is also related to herein a vaccine composition which comprises inactivated bacteria of one or more single culture(s) of *A. wodanis*, inactivated bacteria of one or more mixed culture(s) of spp. *A. wodanis* and *M. viscosa* and inactivated bacteria of one or more single culture(s) of *M. viscosa*.

In addition, it is also related to a vaccine composition which comprises inactivated bacteria of one or more single culture(s) of *A. wodanis*, and/or inactivated bacteria of one or more single culture(s) of *M. viscosa*. Furthermore, it is also related to a vaccine composition which comprises inactivated bacteria of one or more mixed culture(s) of spp. *A. wodanis* and *M. viscosa* and inactivated bacteria of one or more single culture(s) of *M. viscosa*.

It is also related to herein a method for preparing a culture of modified *M. viscosa* by adding extracellular products obtained from one or more mixed culture(s) with *M. viscosa* and *A. wodanis* or one or more culture(s) of *M. viscosa* grown with additions of naturally purified or recombinantly produced structures or components of *A. wodanis* that modulate the antigenic outlook of *M. viscosa* to one or more single culture(s) of *M. viscosa*, inactivating said bacterial cells and thereafter preparing a vaccine composition therefrom. It is also related to herein a composition comprising inactivated bacteria obtainable by such a method, and the use of such a composition as a vaccine, such as for vaccinating against wodanosis and/or winter ulcer.

The present disclosure is further supported and exemplified by the following experimental section, but is not limited to thereto.

EXPERIMENTAL SECTION

Experimental Methods

Preparation of vaccine cultures, vaccine and vaccination of Atlantic smolts for Example 2, 3 and 8 and for antibody production in rabbits Example 6. Any strain of *Moritella viscosa* and *Aliivibrio wodanis*, such as exemplified herein, may be used for performing the experiments described in the below.
NVI=National Veterinary Institute
Day 1:
One strain of *Moritella viscosa* (NVI 06/09/139, 5427) and one strain of *Aliivibrio wodanis* (NVI 06/09/139, 5426) were inoculated onto a blood agar plate (Blood agar base 2 (Difco) with 5% cattle blood and 2% additional NaCl) by a plastic loop from a frozen vial of 1 ml culture made from colonies washed from agar plates into Luria broth with 2% NaCl and 10% glycerol and kept at −80° C. The blood agar plate enriched with NaCl were incubated at +8° C. for 4 days.
Day 4:
Re-inoculated both strains on another blood agar plate enriched with NaCl as on Day 1 and incubated at +8° C. for 3 days.
Day 7:
Inoculated a few colonies of both strains from the blood agar plates enriched with NaCl and incubated for 3 days into two different tubes with 5 ml Luria broth with 1% NaCl (LB1) and incubated the tubes at +8° C. with agitation for 3 days.
Day 10:
Transferred the two cultures to 10-fold dilution series in 24-well micro-titre plates. The dilution set-up was 900 µl LB1 and 100 µl broth culture incubated from Day 7 to 10 as described. The dilutions were made to $10^{-3}$ and all 1000 µl from these last wells were transferred into a common Erlenmeyer flask with 10 ml LB1. This mixed culture of *M. viscosa* and *A. wodanis* was incubated at +8° C. with agitation (800 rpm) for 2 days. Transferred 1 ml of each broth culture from Day 7 with *M. viscosa* and *V. wodanis*, respectively to 4 ml LB1 in small Erlenmeyer flasks and incubated at +8° C. with agitation.
Day 12:
Transferred 5 ml from each of the three cultures started at Day 10 to Erlenmeyer flasks with 45 ml LB1. The three flasks where incubated at +8° C. with agitation.
Day 14:
Vaccine production: The $OD_{600}$ of each of the 3 cultures was measured. The mixed culture had an OD=1.650, the *M. viscosa* culture had an OD=1.721 and the *A. wodanis* culture had an OD=1.601.

Each of the 3 cultures were centrifuged at 12.500×g (10.000 rpm at Sorvall cooling centrifuge) at +4° C. in 5 minutes. The pellet was resuspended in 10 ml PBS buffer with 1% formalin for Example 2, not 3 and 8. Extra NaCl to a total of 2% was used in the PBS buffer for resuspension of the *M. viscosa* pellet and the mixed pellet. The suspensions were incubated at +4° C. for 2 hours.

The suspensions of bacterial cells were then re-centrifuged at 12.500×g (10.000 rpm) at +4° C. (Sorvall centrifuge) for 5 min and washed the pellet 4 times with PBS buffer (with extra NaCl up to a total of 2% for the *M. viscosa* cells and for the mixed cell suspension) at +4° C. for 1 minute at 12.500×g. Resuspended the pellets in PBS buffer to an $OD_{600}$ of approximately 1.0.

Sterility control was made by inoculating 10 µl of each cell suspension in PBS buffer onto blood agar plates with 2.5% NaCl before incubation at +8° C. for 6 days.

Example 2

Four research vaccines were prepared, A, *M. viscosa*+adjuvant; B, *A. wodanis*+*M. viscosa* adjuvant; C, Adjuvant control (PBS buffer+adjuvant) and Negative control, PBS buffer.

Example 3

Five research vaccines were prepared, A, *M. viscosa*+adjuvant; B, *A. wodanis*+*M. viscosa*+adjuvant; C, *A. wodanis*+adjuvant; D Adjuvant control (PBS buffer+adjuvant) and Negative control, PBS buffer.
Preparation of Vaccine Composition:
Mixture of adjuvant and antigen: For vaccine A, B and C 15 ml antigen preparation in a 50 ml syringe with luer lock were prepared, 15 ml Freund's incomplete adjuvant was filled in another 50 ml syringe with luer lock. The syringes were connected through a 3-way valve well tightened. The contents of the 2 syringes were mixed by being transferred completely until empty syringe from one syringe to another in a large number of repetitions for a total time of between 15 to 45 min for each vaccine preparation. The process is continued until the vaccine preparation is turned into a thick whitish even mixture before the third gate is opened on the 3-way valve and the contents is emptied into a 50 ml tube that is left at +4° C. where the preparation is getting further thickened.

The adjuvant control vaccine (C in Example 2 and D in example 3) was made by mixing 10 ml PBS buffer with 10 ml Freund's incomplete adjuvant following the same mixing procedure as with vaccine A, B and C with antigens.
Day 15:
Vaccination: The salmon smolts were anaestetized in benzocaine bath and vaccinated by injection of 0.1 ml of the vaccine intraperitoneally before being released into a common tank for all the 5 groups.

Result of the sterility control: No growth of the vaccine strains was observed but surprisingly a coagulase-negative *Staphylococcus* were growing from all 3 A, B and C vaccine preparations indicating addition of a contaminated addition probably during washing of the bacterial cell pellets.

Preparation of Bacterial Cultures for Challenge of Atlantic Salmon

Example 1

For bath pre-challenge one strain of *Moritella viscosa* (NVI 06/09/139, 5427) was inoculated onto a blood agar plate (Blood agar base 2 (Difco) with 5% cattle blood and 2% additional NaCl) from frozen glycerol stock culture at −80° C. and incubated at 12° C. for 24 h in 10 ml Marine Broth (Difco) before 17 ml of the grown culture were added to 600 ml fresh MB medium and after 24 h the $OD_{600}$ was 1.0. For preparing cultures of *A. wodanis* in contact with *M. viscosa* by exchange of extracellular products with a size less than 14 kDa but with no cell-to-cell contact one of the cultures was cultured in semi-permeable containers within a flask of a culture with the other species.

The culture was diluted and bacterial concentration was estimated after growth on blood agar plates. The bacterial concentration of the prechallenge culture was $1.9 \times 10^9$ cfu/ml.

Three groups of 20 pre-smolts of 50 gram were bath challenged for 1 hour 2 days after end of smoltification and sea-launch with $4.8 \times 10^6$, $9.5 \times 10^5$, and $2.9 \times 10^5$ cfu/ml respectively of challenge bath culture with *M. viscosa*. After 17 days 59, 47 and 42% mortality were recorded, respectively. A challenge dose of $1.0 \times 10^6$ cfu/ml was chosen in the main challenge with *M. viscosa* and $1.5 \times 10^6$ cfu/ml for *A. wodanis* (06/09/139, 5426) in the various tank groups in Example 1.

Example 2 and 3

One strain of *Moritella viscosa* (NVI 06/09/139, 5427) and one strain of *Aliivibrio wodanis* (NVI 06/09/139, 5426) were inoculated onto a blood agar plate (Blood agar base 2 (Difco) with 5% cattle blood and 2% additional NaCl) as in Example 1. Both strains were separately added to 10 ml fresh Marine Broth in a 100 ml Erlenmeyer flask that was incubated at 8° C. on a shaker at 200 rpm for 2 days before one ml was inoculated into 20 ml Marine Broth in an identical flask that was shaken at the same speed at 7° C. for 24 h. Three copies of these 20 ml cultures of both *M. viscosa* and *A. wodanis* were added together to 400 ml Marine Broth in three 1 l Erlenmeyer flasks that were incubated at 7° C. with shaking (200 rpm) until $OD_{600}$ of the mixed cultures of *M. viscosa* and *A. wodanis* was measured to >1.0. The cultures were adjusted with fresh Marine Broth to $OD_{600}=1.0$ giving a cfu/ml of approximately $1 \times 10^9$. The cultures were diluted on blood agar plates and cfu/ml were estimated to $5 \times 10^6$ cfu/ml for both *M. viscosa* and *A. wodanis* in the mixed cultures. For the challenge in Example 2 a total of 1250 ml mixed culture was added to 250 l of sea water.

Example 4 and 7

For the bath challenge of smolts with single culture of *Aliivibrio wodanis* (NVI 06/09/139, 5426) the culture was prepared as in Example 1 and the challenge was performed as in Example 3. The challenge dose of *A. wodanis* was $1.2 \times 10^6$ cfu/ml sea water.

For bath challenge with mixed cultures of *M. viscosa* and *A. wodanis* the cultures were prepared as described in Example 2 and 3 and the bath challenges were performed with 2 different groups and the concentrations were $4 \times 10^5$ for *M. viscosa* and $1.2 \times 10^6$ for *A. wodanis* for group $A_{mix}$ and for group $B_{mix}$ the challenge concentrations were $1.3 \times 10^6$ cfu/ml for *M. viscosa* and $9 \times 10^6$ cfu/ml for *A. wodanis*.

Example 5

For intraperitoneal challenge of smolts with monocultures of *M. viscosa* (water temp 10° C.) and *A. wodanis* (water temp 8 and 10° C.) the cultures were started and grown as in Example 1 except for the incubation temperature that was 9° C. A total of $1.3 \times 10^7$ bacterial cells of *M. viscosa* and $8.7 \times 10^7$ bacterial cells of *A. wodanis* were inoculated intraperitoneally in a volume of 0.1 ml.

Example 6

For preparation of bacterial cells for inoculation in rabbits for production of polyclonal sera for Western blot studies single bacterial cultures of *M. viscosa* and *A. wodanis* and mixed culture of the same bacteria the techniques used for vaccine preparation in Example 2 and 3 were used.

Experimental Results

Example 1

Bath Challenge with Single Cultures of *M. viscosa* and *A. wodanis* Grown with and without Impact of Extracellular Products with a Cutoff of Less than 14 kDa from the Other Culture and Co-Challenge with Both Bacteria Together Six groups of 55 smolts (48 g) each Group 1: Challenged with mono-cultivated *M. viscosa* in 1 h Group 2: Challenged with co-cultivated *M. viscosa* (separated from *A. wodanis* by 12-14 KDa cut-off) for 1 h Group 3 and 4: Challenged with both co-cultivated *M. viscosa* and *A. wodanis* (separated from each other by 12-14 KDa cut-off) for 1 h Group 5: Challenged with co-cultivated *A. wodanis* (separated from *M. viscosa* by 12-14 KDa cut-off) for 1 h Group 6: Challenged 3 h with co-cultivated *A. wodanis* (separated from *M. viscosa* by 12-14 KDa cut-off) before adding of co-cultivated *M. viscosa* for 1 h The temperature ranged between 6.7 and 7.4° C. during challenge. The intake water was UV-desinfected sea-water.

Bath challenge resulted in mortality starting at day 2 after challenge and with the highest number of dead smolts from day 5 to 10 increasing the cumulative mortality from 20 (+/−5%) to 75-80% for Group 1, 2, 3 and 4 within those 5 days of the outbreak. At day 16 the cumulative mortality was between 90 and 98% for all these 4 groups. In Groups 3 and 4 both *M. viscosa* and *A. wodanis* were isolated from head kidney and ulcers.

The mortality in Group 6 deviated from Groups 1 to 4 after day 6 with fewer dead fish per day and with 83% cumulative mortality after 17 days.

For the first time it was possible to record mortality in smolts bath challenged with *A. wodanis* alone. However, the tank with Group 5 was contaminated with *M. viscosa* possibly from day 8 since *M. viscosa* was detected in the water and internal organs of dead smolts. One smolt died at each of day 4, 5 and 6 and it was verified that *A. wodanis* was growing from the head kidney. Several more died on day 9 with both *A. wodanis* and *M. viscosa* from the head kidney and both bacteria were in the water. Additional single smolts died at day 10, 11, 15 and 17 in this group all of them with both *A. wodanis* and *M. viscosa* isolated from the head kidney. In total the cumulative mortality in Group 5 reached 20% at day 17. The tank with Group 5 was run for 6 more days during which only 2 more smolts died and one of them had *A. wodanis* in multiple organs while the other one had *M. viscosa* in the liver. Among the survivors on day 23 when Group 5 was terminated, only 2 smolts had *M. viscosa* in the head kidney. After Group 5 was contaminated with *M. viscosa* possibly on day 8 it was expected that the mortality curve should pick up with the curves in Groups 1 to 4, but it remained unexpectedly low.

The experiment with Group 5 was repeated in an attempt to avoid contamination with *M. viscosa* and involve only *A. wodanis*. In this repeated experiment with the same batch of smolts and same conditions for water including temperature, one smolt died each of the days 3, 10, 11 and 13 ending with a cumulative mortality of 7.8%. It was discussed that worned back fins could have assisted *A. wodanis* in getting into these 4 smolts.

Conclusions from the Challenge Experiment Example 1:

From 2 days after bath challenge it was possible to see local swellings in the skin of the smolts and from day 8 all dead smolts demonstrated large skin ulcers.

An outbreak situation occurred in Groups 1 to 4 from day 5 to 10 and also in this period the concentration of *M. viscosa* in the water peaked. Groups 1 to 4 demonstrated the same disease situation with the cumulative mortality between 90 and 98% at day 16 and 17. This means that co-cultivation of *M. viscosa* together with *V. wodanis* separated by semi-permeable membranes did not have an impact on the mortality. Neither did the combination of *M. viscosa* and *A. wodanis* both co-cultivated in semi-permeable membranes in the challenge change the mortality.

The bath prechallenge of smolts with *A. wodanis* for 3 h before bath challenge with *M. viscosa* reduced the mortality rate from day 6 and ended with a 10% lower cumulative mortality.

Bath challenge with *A. wodanis* alone (co-cultered across semi-permeable membrane with *M. viscosa*) ended with 7.8% mortality (4 of 51 smolts).

Introduction of *M. viscosa* into the population 8 days after bath infection with *A. wodanis* did not increase the cumulative mortality to more than 20% after 17 days (24% after 23 days).

Whenever *A. wodanis* is included in the challenge it is occurring in the wounds and internal organs at the same level as *M. viscosa*.

From this challenge study it is possible to make an hypothesis that under the given conditions M, viscosa is a highly virulent pathogen able to run the winter ulcer infection regardless of contact with *A. wodanis* through semi-permeable membranes (12-14 kDa cut-off)

*A. wodanis* is able to cause disease and mortality to a low level <8% alone under the given conditions

*A. wodanis* is able to inhibit *M. viscosa* in its virulence/pathogenicity but only given that *A. wodanis* must be on the scene before *M. viscosa* arrives. The longer *A. wodanis* is alone with the smolts the lower is the virulence of *M. viscosa* (*A. wodanis* introduced at the same time there is no inhibition of *M. viscosa*, after 3 h pre-challenge with *A. wodanis* virulence by *M. viscosa* is reduced with 10%, after 8 days (very low dose from splash?) the virulence is reduced with close to 70%).

Alternatively the inhibitory effect of *A. wodanis* is dependent on an adjuvant effect of the smolt unless the *M. viscosa* infection is opening a "window" for *A. wodanis* to get into the smolt and perform its inhibitory effect.

Extreme short conclusion: High mortality with *M. viscosa*, same mortality with *M. viscosa* and *A. wodanis* cultivated together before challenge and tendency to delayed mortality when *A. wodanis* was introduced in the bath challenge 3 hours before *M. viscosa*.

Example 2

Figure 3:
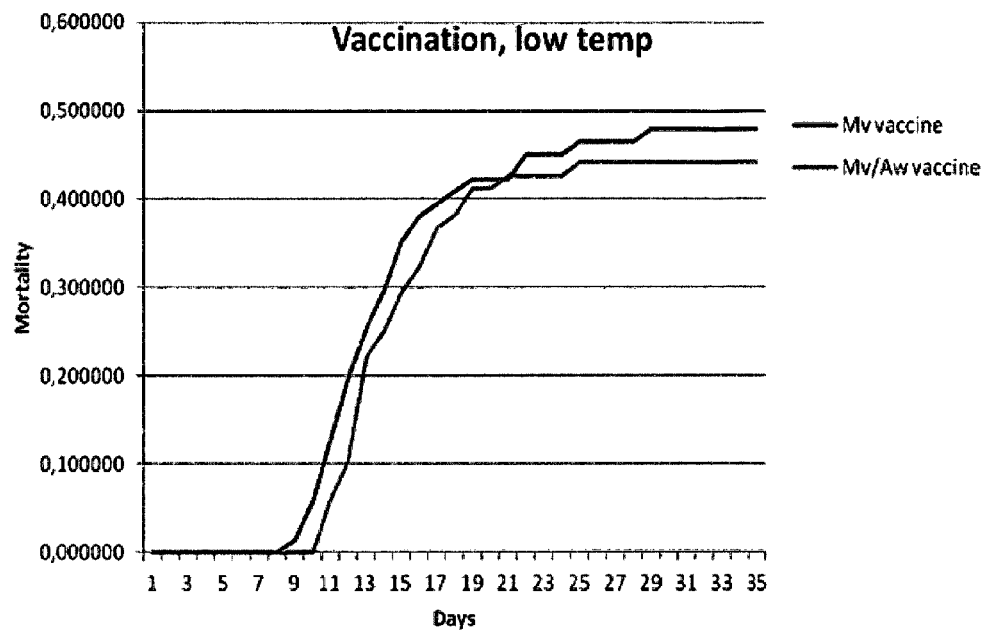

Bath Challenge with Co-Cultured *M. viscosa* and *A. wodanis* after Vaccination with *M. viscosa* Cultivated as Single Culture and Vaccination with a Vaccine Made from a Co-Culture of Both Bacteria (FIG. 3)

Four groups of 71, 68, 15 and 20 smolts (55 g) each. The pre-smolts were vaccinated 8 weeks before smoltification and challenge in 2 different vaccine groups, 1 adjuvant group and 1 negative control group. All groups were kept in one tank of 250 l and bath challenged for 1 h at a temperature of 8° C. with a culture of *M. viscosa* ($5 \times 10^6$ cfu/ml) and *A. wodanis* ($5 \times 10^6$ cfu/ml) physically grown together. The sea-water was UV-desinfected.

Group 1: Vaccinated with mono-cultivated *M. viscosa* (n=71)

Group 2: Vaccinated with *M. viscosa* and *A. wodanis* physically grown together (n=68)

Group 3: Injected with only Freunds incomplete adjuvant (n=15)

Group 4: Injected with PBS (n=20)

The first dead smolts appeared in Group 1 on day 8 after challenge in and from day 10 in the other groups. Most smolts died within 10 days from the first diseased smolts appeared. The experiment was terminated 34 days after challenge after 6 days without any observed diseased or dead smolts.

Cultivation from Head Kidney

After cultivation of bacteria from smolts (n=30) dying during the outbreak in Group 1 there were seen more *A. wodanis* colonies on the plates varying from 60 to 100% compared to *M. viscosa* in 19 of the dead smolts (63%), while *M. viscosa* was dominating in 4 (13%), both bacteria with equal frequency in 3 (10%) and impossible to count in 4 smolts (13%). The smolts that died the first 4 days of the outbreak had a complete dominance by *A. wodanis* in the culture from the head kidneys.

After cultivation of bacteria from smolts (n=29) dying during the outbreak in Group 2 it was more *M. viscosa* colonies on the plates varying from 60 to 100% compared to *M. viscosa* in 15 of the dead smolts (52%), while *A. wodanis* was dominating in 7 (24%), both bacteria with equal frequency in 6 (21%) and impossible to count in 1 smolt (3.4%).

After cultivation of bacteria from smolts (n=7) dying during the outbreak in Group 3 it was more *A. wodanis* colonies on the plates varying from 60 to 100% compared to M, viscosa in 5 of the dead smolts (71%), while *M. viscosa* was dominating in 2 (29%).

After cultivation of bacteria from smolts (n=8) dying during the outbreak in Group 4 it was more *A. wodanis* colonies on the plates varying from 60 to 100% compared to *M. viscosa* in 4 of the dead smolts (50%), while *M. viscosa* was dominating in the other 4 (50%).

Cultivation from head kidney of smolts euthanized at the end of the study gave no growth except a few colonies of *M. viscosa* or *A. wodanis* from one of the surviving smolts in each of Group 1, 2 and 3 and two from Group 4. Probably these smolts would have died from infection within some time. These results show that ulcer mostly develop before septicemia during an outbreak in an artificially bath challenged population in both a vaccinated population and in unvaccinated smolts (see below under Ulcers). This may mean that *A. wodanis* is primarily performing its control of *M. viscosa* in the ulcers reducing the frequency of septicemic development with bacteria in the head kidney. This could occur in parallel with better protection against changed outlook of inhibited *M. viscosa*.

In conclusion vaccination with mono-cultivated *M. viscosa* reduced the number of *M. viscosa* in the head kidney compared to *A. wodanis*. In smolts vaccinated with both *M. viscosa* and *A. wodanis* physically grown together *M. viscosa* was more frequent in the head kidney than *A. wodanis*.

*M. viscosa* grown as single vaccine culture protect better towards the number of bacteria in the head kidney when included in the vaccine.

Ulcers

All smolts that died from day 10 had increasingly large ulcers up to 30 to 40 mm in size. There was a tendency to larger ulcers in Group 2 compared to Group 1 and 3 and a tendency to less prominent ulcers in Group 4, the negative control group.

Lower ulcer frequency (13%, n=38) in survivors in Group 1 (*M. viscosa* vaccinated, mono-cultivated) means that *M. viscosa* alone is most important for starting ulcer development.

Relative high ulcer frequency (37%, n=38) in survivors of Group 2 (*M. viscosa/A. wodanis* vaccinated, cultured physically together) indicates that *M. viscosa* has its mono-cultivated surface when creating ulcers under these conditions.

Survivors in the adjuvant group had an ulcer frequency of 43% (3 of 7) and survivors in the control group had an ulcer frequency of 77% (7 of 9). This indicates that the adjuvant stimulates the immune system to hinder *M. viscosa* to create ulcers under these conditions. At the same time it can be concluded that a *M. viscosa* physically cultivated with *A. wodanis* have an antigen outlook that is only contributing to 6% protection from ulcer development in survivors compared to 24% (4× better) protection from mono-cultured *M. viscosa* on top of 34% contribution from the adjuvant.

Altogether this tells that a vaccine against winter ulcer should contain mono-cultured *M. viscosa* to protect against ulcers under the conditions used (8° C.) and bacteria cultivated physically together for protecting against septicemia and death.

A vaccine group containing mono-cultivated *M. viscosa* and physically co-cultivated Mv/Vw would from these results potentially protect the smolts better than any of the 2 groups involved in the study. It might be a coincidence that the Group 1 and 2 had same vaccine protection unless ulcer development is unlinked to septicemia and death.

Protection

There was no significant difference in protection between Group 1 (46.5% cumulative mortality) and Group 2 (44.1% cumulative mortality). Since the adjuvant group (Group 3) had 53.3% cumulative mortality and the negative control group (Group 4) had 55% cumulative mortality the level of protection created by the two test vaccines cannot be called impressive. However when the smolts surviving until day 34 with ulcers are added to the smolts that died up to day 34 and which all had ulcers the figures become different. A total of 53.5% in Group 1 had developed ulcers at day 34 after bath challenge. In Group 2 a total of 64.7% had developed ulcers, while in Group 3 a total of 73.3% and in Group 4 a total of 90% developed ulcers.

Results from laboratory assays including cultivations on agar plates and in cell cultures demonstrate that cell-to-cell contact between *M. viscosa* and *A. wodanis* under culture makes *A. wodanis* able to inhibit the growth and virulence of *M. viscosa*.

When adjuvant is used alone as vaccine almost 17% protection is gained compared to the negative control group. This is in accordance with a study by Mikkelsen et al (Poster). In the group that was vaccinated with monocultured *M. viscosa* 36.5% better protection was gained compared to the negative control. In the group vaccinated with both *M. viscosa* and *A. wodanis* physically cultured together only 25% protection against ulcer development compared to the negative control group was gained.

Smolts dead from the challenge mostly have both *M. viscosa* and *A. wodanis* together in the head kidney. This means that *A. wodanis* probably inhibits the virulence of *M. viscosa* and possibly impacts the antigenic outlook of *M. viscosa* cells when they are inside the fish body. This should lead to low protection against *M. viscosa* in Group 1 as soon it is inside the smolt body. This coincides with few survivors with ulcers. On the other hand will the inhibition of *M. viscosa* caused by *A. wodanis* increase the time before the smolts with septicemia dies. (This scenario coincides with today's vaccination status in the salmon farms.)

Smolts vaccinated with physically co-cultured *M. viscosa* and *A. wodanis* will be less protected against ulcer development by *M. viscosa* but be more protected against *M. viscosa* when it grows physically together with *A. wodanis* in the smolt body. The control of *A. wodanis* by vaccination in Group 2 will on the other side counteract the inhibitory effect by *A. wodanis* on *M. viscosa*.

The most obvious conclusion from the vaccine study in Example 2 is that only *M. viscosa* in the vaccine gives some protection against winter ulcer and that the *A. wodanis* component has no protective impact. This means that *A. wodanis* should have no major pathogenic role which is in line with the challenge study.

However, hypothetic conclusions from the vaccine study in Example 2 can be drawn from the observation that *M. viscosa* is the most aggressive ulcer developer among the 2 bacteria challenged and that it performs this ulcer activity best when the cells have the outlook as when they are cultivated without being physically in contact with *A. wodanis*. This is supported by the fact that the monovalent and monocultured *M. viscosa* vaccine used in Group 1 protects best against ulcer development. In addition it can be noted that it probably takes some days before the balance between *M. viscosa* and *A. wodanis* has established in the internal organs since the smolts that died the first 4 days of the outbreak in Group 1 had no visible growth of *M. viscosa*, only *A. wodanis*. Alternatively, the monovalent *M. viscosa* in the vaccine in Group 1 may have hindered the introduction of the *M. viscosa* into the smolt body postponing its appearance in the head kidney. This is surprising since *A. wodanis* was growing dominantly from head kidney of these smolts. Probably the vaccine effect in Group 1 eliminated the *M. viscosa* before they started the physical interaction with *A. wodanis* with the result of a changed antigen outlook. Probably the high toxin production by these mono-cultured *M. viscosa* killed these fish fast even if the immune defense of the smolts eliminated the growth of *M. viscosa* on plates. Alternatively, the *A. wodanis* were virulently killing these first dead smolts directly without the impact or interaction by *M. viscosa*.) The same occurred with the first smolts that died in Group 3 and 4 on day 10 but not so clearly in Group 2 where *M. viscosa* grows in higher numbers (varying from 20 to 90% of the colonies) from the head kidney from the first dead smolt. *M. viscosa* dominated the growth from head kidney of dead fish from this group. A clear indication that can be seen from this is that the antigens from a physically co-cultured *M. viscosa* with *A. wodanis* in the vaccine is not protecting very well against the normally aggressive *M. viscosa*. The *M. viscosa* component of the vaccine in Group 2 is only protecting the smolts from the already inhibited version of *M. viscosa* under the control of *A. wodanis*. This version is actually a low-virulent *M. viscosa*. In addition the inhibiting *A. wodanis* is inhibited by the immune system because the physically co-cultered *A. wodanis* is included in the vaccine. These phenomenons may explain the relatively low protection by the vaccine in Group 2. Hypothetically a

*M. viscosa* component as in the vaccine of Group 1 added to the vaccine used in Group 2 would have reduced the mortality with a substantial contribution. Also an addition of a monocultured *A. wodanis* would from this hypothesis have further improved a vaccine.

In the adjuvant group there seems to have been a specific protection against *M. viscosa*. In the negative control group there is no such tendency in growth between *M. viscosa* and *A. wodanis* in culture from head kidney of dead smolts.

In total the final outcome of the vaccine study related to Group 1 and 2 is impacted by the interplay of all the factors mentioned and possibly more. However, the easiest way to look at the outcome of the study is to study the total level of ulcer development in the various groups as discussed. This holds well when the virulence activity/pathogenicity of *M. viscosa* is considered.

Under the conditions of relatively low temperature etc. for this vaccine study it seems that *M. viscosa* is the aggressive pathogen that is actively inhibited by *A. wodanis*. *A. wodanis* is not a clear pathogen in this study at low temperature, unless in the initial phase of disease in Group 1 in which *A. wodanis* may have an unknown responsibility for the mortality of the disease. *A. wodanis* still have a strong inhibitory action on *M. viscosa* cells resulting in a prolonged outbreak in this challenge study.

Example 3

Figure 5:
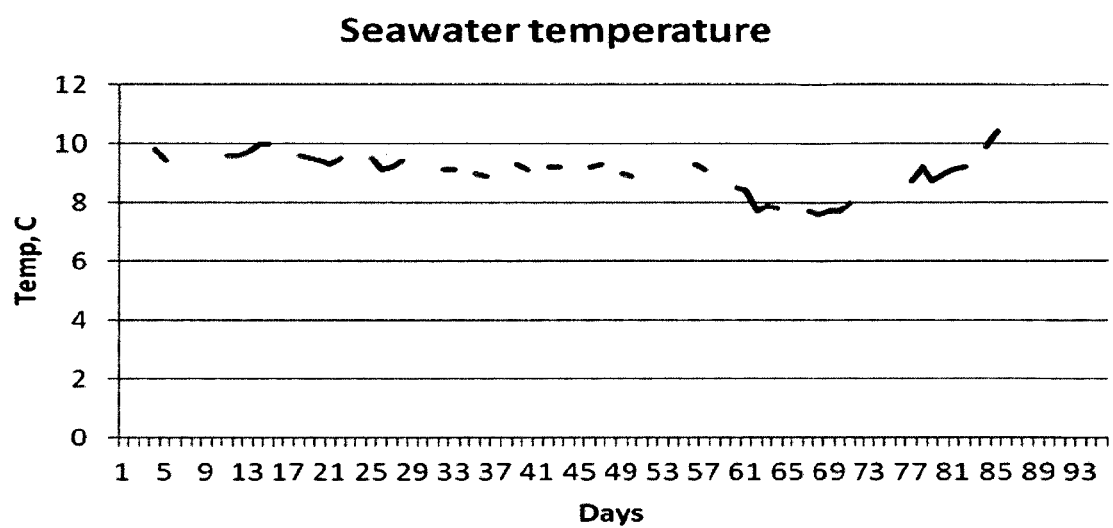
Figure 8:
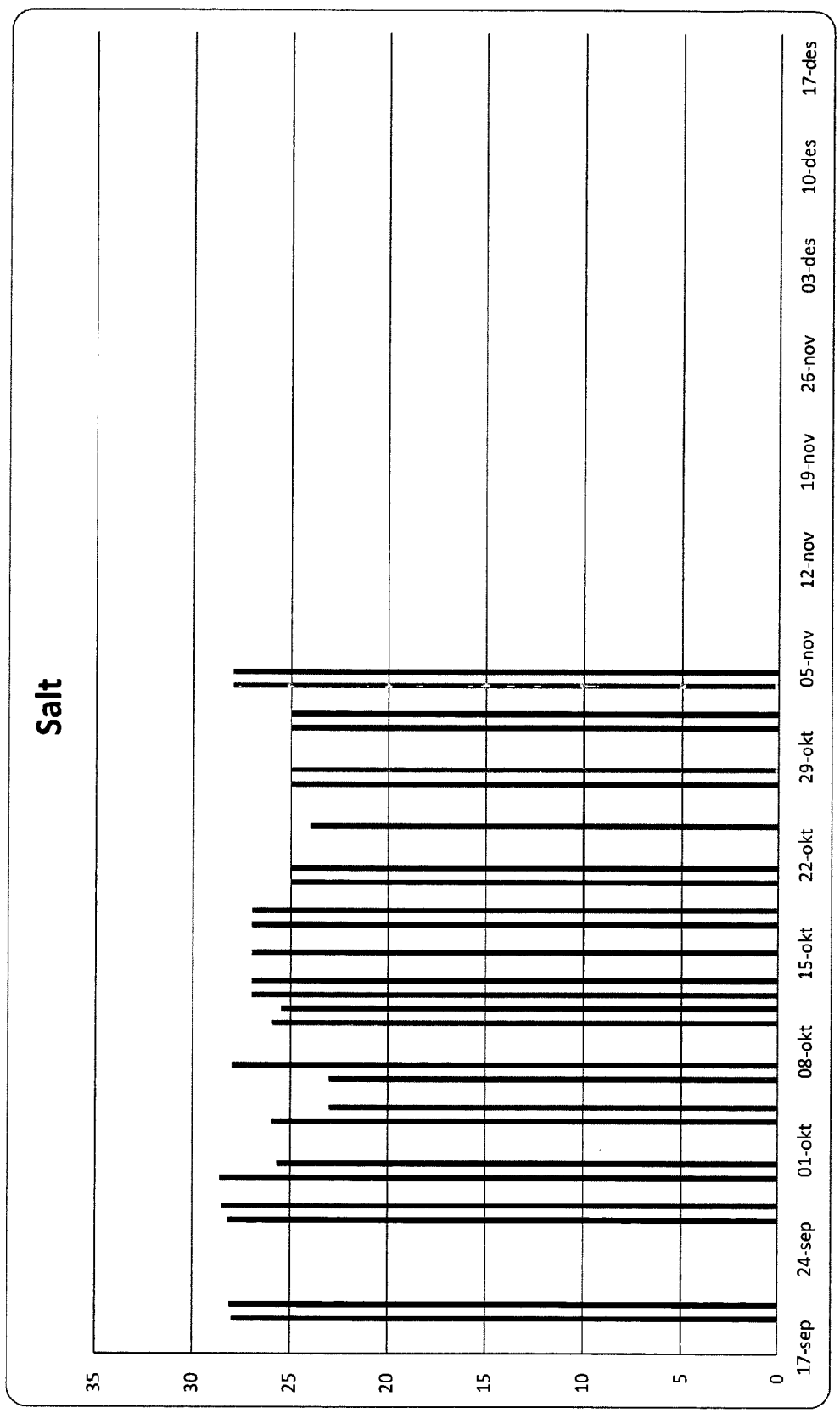
Figure 9A:
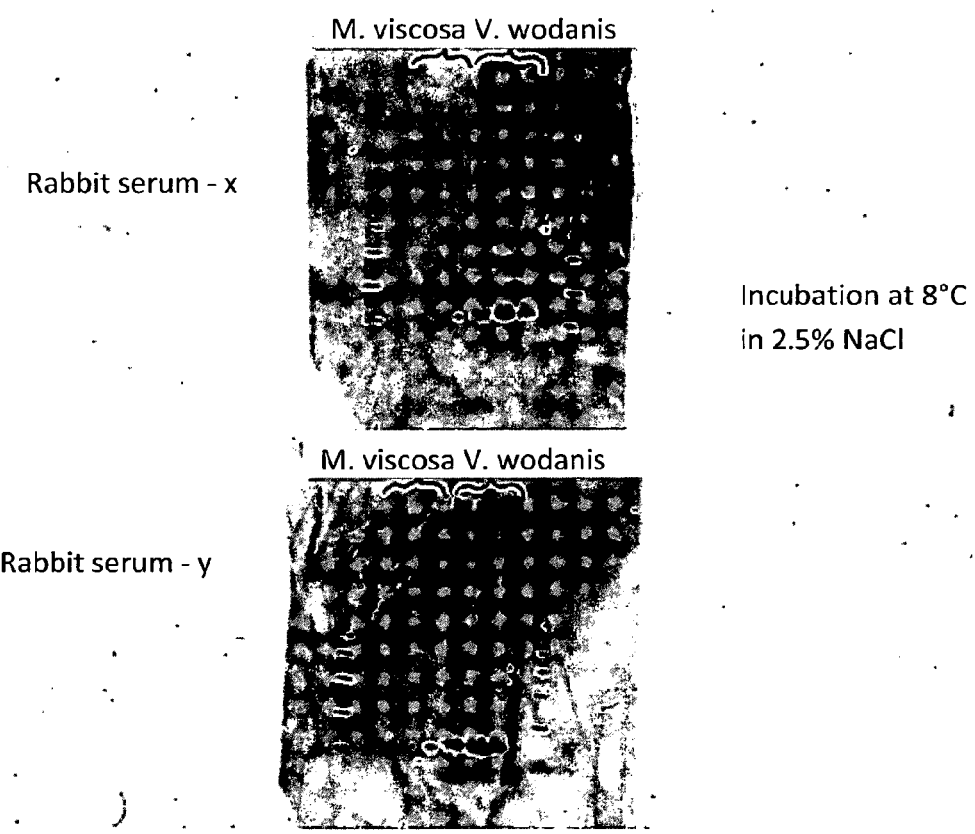
Figure 9B:
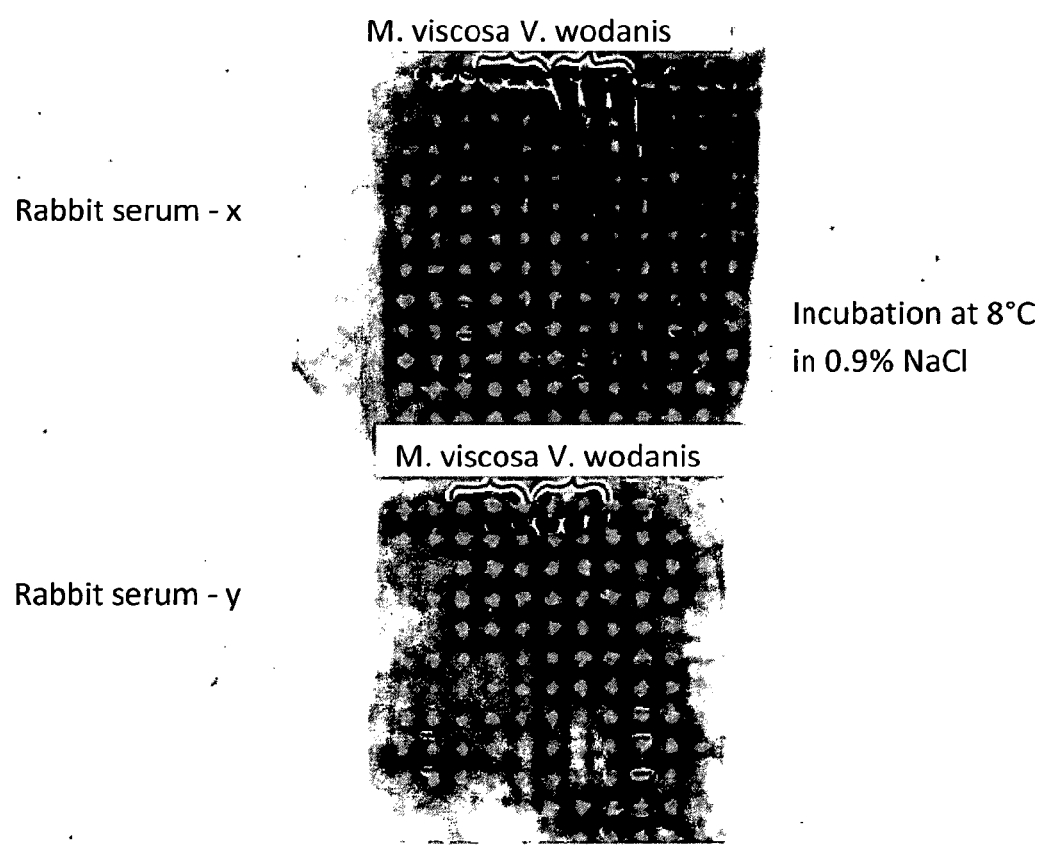
Figure 9C:
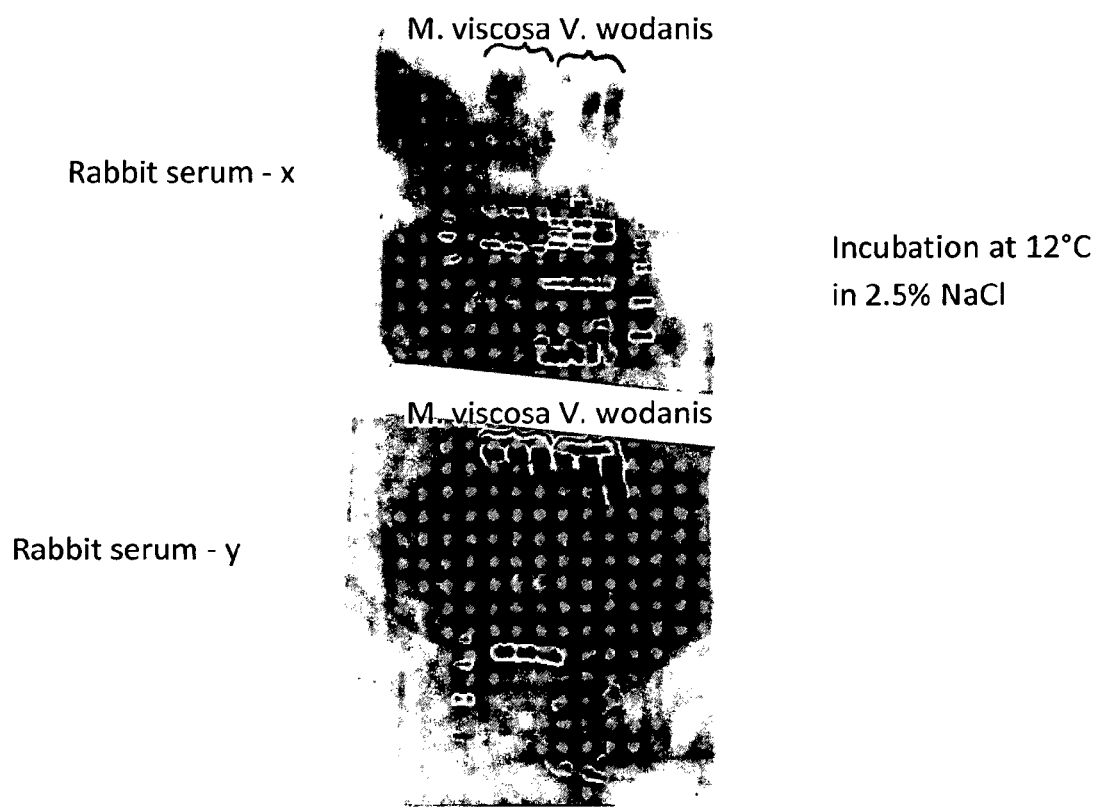
Figure 9D:
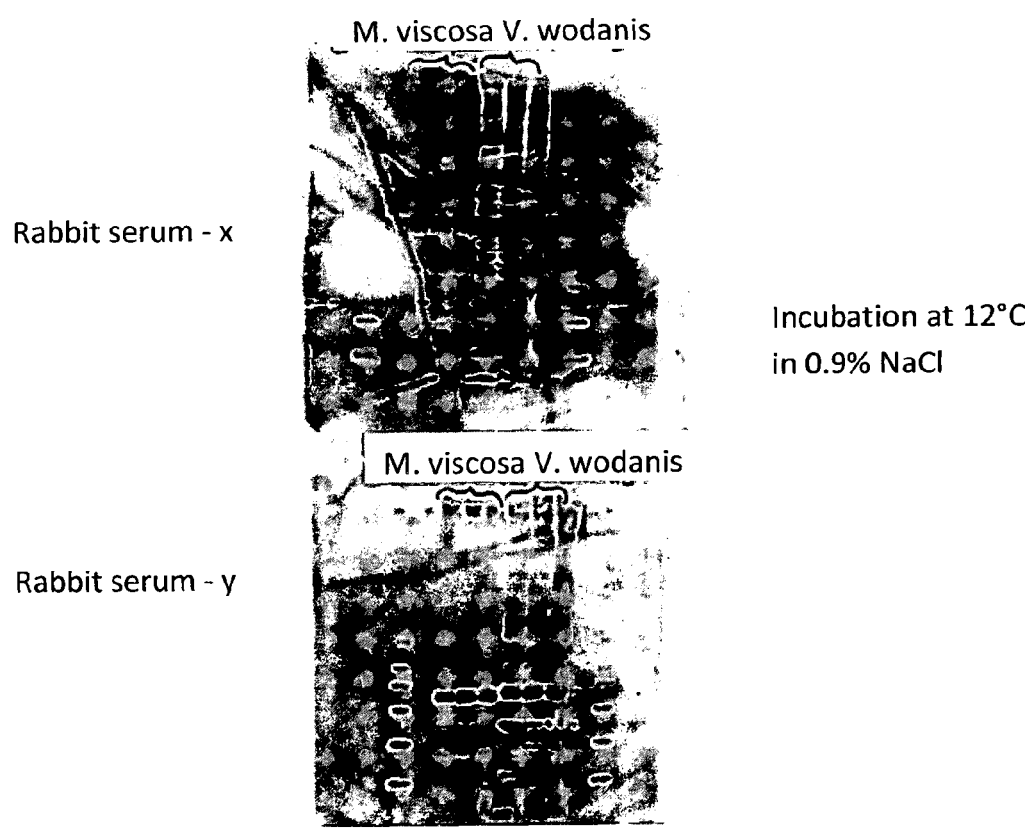

Bath Challenge with Co-Cultured *M. viscosa* and *A. wodanis* after Vaccination with *M. viscosa* and *A. wodanis* Cultivated as Single Cultures and Vaccination with a Vaccine Made from a Co-Culture of Both Bacteria (FIGS. 4, 5 and 8)

Four hundred Atlantic salmon pre-smolts (average weight 42 g) were shipped by road 500 km in a oxygenated freshwater tank of 700 l and stored in a 1200 liter tank for 14 days before vaccination and marking by fin-clipping, returned to the same tank and put on 24 h continuous light 7 days after vaccination, re-circulated water, temp 12.5° C. from 16 to 32 days after vaccination. From day 30 after vaccination casualties caused by organic load and bacterial growth on the gills occurred, Septicemia caused by *Aeromonas hydrophila* was verified and a high diffuse bacterial load in water was demonstrated. The smolts were moved to flow-through freshwater from day 39 after vaccination and transferred to seawater facilities 45 days after vaccination. At this point 75 smolts were lost due to bacterial growth in the freshwater re-circulation system when smolts got close to smoltification.

After transfer the smolts were put to seawater after 2 days. During the 2 first days in seawater 54 smolts died due to stress from salt water. At day 3 from sea launch the smolts were given 1.8% salinity for 8 days when full seawater was given. A total of 78 smolts died from saltwater stress.

Figure 7:
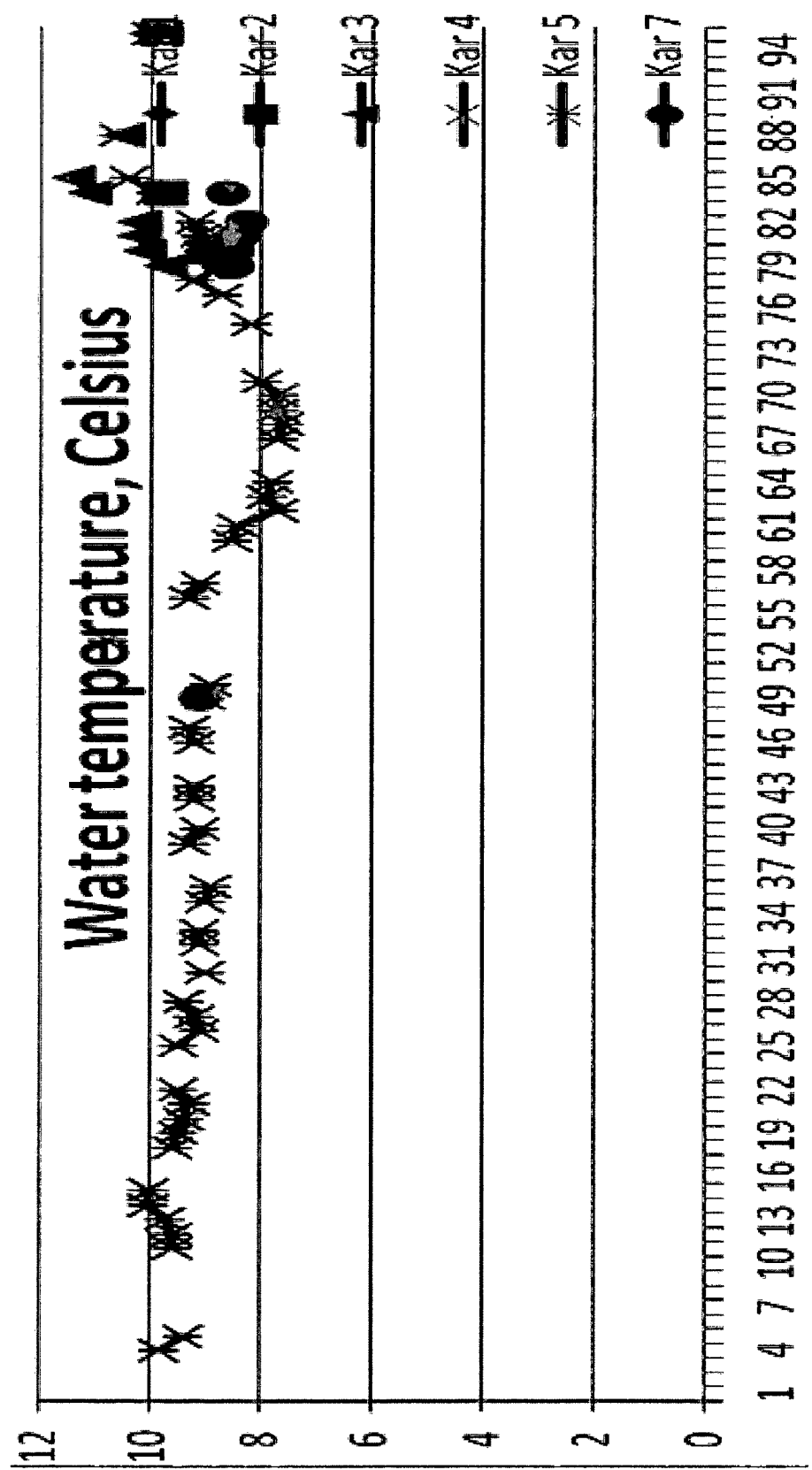

The water temperature at 60 m depth surprisingly increased from 8° C. to 10° C. 5 days after sea launch and passed 11° C. the following days. This change normally starts 3 months later. It was decided to mix in freshwater of 8° C. to cool down the water temperature in the tank since the primary plan was to run the experiment close to 8° C. The salinity was 2.8% and the temperature between 9 and 10° C. throughout most of the study (FIGS. 5, 7 and 8).

Bath challenge was performed with 240 smolts left out of the 392 vaccinated parr individuals 14 days after sea launch. The challenge culture was a physical co-culture of *M. viscosa* and *A. wodanis* with a cfu of $5 \times 10^6$ cfu/ml for each of the two species *M. viscosa* and *A. wodanis* in the mixed culture in the challenge water in the tank. The tank volume was reduced to 200 liter, the water flow halted and oxygen was added before the co-culture was added for 1 hour before the water flow was started again and the water volume raised and the challenging bacteria titrated down. The seawater was not disinfected.

Group 1: Vaccinated with mono-cultivated *M. viscosa* (n=61)
Group 2: Vaccinated with *M. viscosa* and *A. wodanis* physically grown together (n=81)
Group 3: Vaccinated with mono-cultivated *A. wodanis* (n=55)
Group 4: Injected with only Freunds incomplete adjuvant (n=23)
Group 4: Injected with PBS (n=24)

Disease Development

The first dead smolts appeared in Group 1 and 2 on day 13 after challenge. There was mainly a low daily mortality. Between 3 to 4 weeks after bath challenge there was a tendency to an outbreak with around 2.5% mortality per day. In a period of 82 days the outbreak was followed and the cumulative mortality for that period was 54% with an average daily mortality of 0.66%. The experiment was terminated 95 days after bath challenge but the continued low mortality of the outbreak was the same and possibly would have continued. The first week with disease and from 3 weeks after challenge there was a low mortality that often is typical in field outbreaks of winter ulcer (Aunsmo et al. 2008). The cumulative mortality was 63.9% for group 1, 51.3% for group 2, and 43.6% for group 3. For the small control groups the cumulative mortality was 60.9 and 41.7%, respectively, for the adjuvant and the negative control (FIG. 4). Caused by the chronic form of the disease the diseased smolts developed extensive ulcers covering a relatively large part of the body surface. A few smolt had ulceration of the abdominal wall resulting in exposure of the intestines and visceral organs. Sometimes the jaw and one eye were ulcerated reducing the functionality of these organs.

During the experiment the seawater temperature fluctuated to some extent between above 10 and below 8° C. (FIG. 5). During the first two thirds of the experiment the seawater temperature was between 9 and 10° C. and then dropped to below 8° C. for approximately 2 weeks before the temperature was raised to above 9° C. again. This fluctuation in seawater temperature coincides with a change in mortality in the groups vaccinated with vaccines with either *M. viscosa* or *A. wodanis* (FIG. 4). This phenomenon may reflect the different temperature optimum for causing infections between *M. viscosa* and *A. wodanis*. At the lower temperature the group vaccinated with only *A. wodanis* increased the mortality and the mortality went down for the group that was vaccinated with *M. viscosa* with a delay in about one week from the onset of the fluctuation in the temperature.

Cultivation from Head Kidney

All diseased and dead smolts were cultivated from a skin ulcer and from the head kidney onto blood agar plates with 2.5% and 0.9% NaCl incubated at 8° C. In most of the cases both *M. viscosa* and *A. wodanis* were cultivated from the same sampling and often in a relation of 40 to 60%, or opposite, of the colonies belonging to each of the species. On the plates with 0.9% NaCl it was a strong inhibitory effect of the *A. wodanis* colonies against the *M. viscosa* colonies. The colonies of *M. viscosa* were unusually small in the vicinity of the larger *A. wodanis* colonies and the impact seemed to occur both when the colonies touched each other and when they were separated. The impact seemed clearly to be something else than just competition for nutrients. On blood agar plates with 2.5% NaCl the inhibitory effect between *A. wodanis* and *M. viscosa* was not observed.

The same inhibitory phenomenon produced by *A. wodanis* can be seen on blood agar plates when the two bacteria are cross-streaked and inoculated, i.e. strong inhibition at 0.9% NaCl at both 8° C. and 12° C. but not at blood plates with 2.5% NaCl. In addition the same inhibition of virulence and pathogenicity has been observed in mixed cultures of *M. viscosa* and *A. wodanis* in eukaryotic cell cultures of fish cell lines.

From some of the diseased smolts a darker colony form of *A. wodanis* than the regular one was observed together with the regular colonies of *A. wodanis* and colonies of *M. viscosa*. A potential explanation could be that some *A. wodanis* cells turned into a biofilm mode in the fish body.

Both *M. viscosa* and *A. wodanis* were cultivated from the head kidney of diseased salmon smolts in all except for a few.

Ulcers

A major part of the smolts that died had 2 to 5 large ulcers up to 30 to 40 mm in size on the sides of and at the abdominal side of the body. In particular the skin behind the breast fins was commonly affected by ulcer and many of them penetrated into the abdomen.

In the vaccination and challenge experiment of Example 3 the seawater was not disinfected and by Gram-staining it was possible to observe a relatively high level of long, slender Gram-negative bacteria in addition to Gram-negative shorter rods from the surface of almost every ulcer. The long slender bacteria could not be cultivated on blood agar with 2.5% or 0.9% NaCl and they are possibly the *Tenacibaculum* sp. reported by Olsen et al. (2011) and probably observed by O'Hallovan et al (1991). The ulcers were covered by a greyish, 1 to 3 mm thick, unorganized layer of soft material that can easily be removed. This layer is also observed in ulcers seen during field outbreak including in ulcers healing until the skin has recovered a regular structure. It is relevant to hypothetize that *Tenacibaculum* sp. is producing this greysih layer alone or in collaboration with ulcer fluids from the smolt as a form of a biofilm covering the ulcer and sealing off the ulcer from the seawater. By cultivation from the ulcers on blood agar it was only growing a few colonies (3 to 8 colonies often with a mucoid appearance) of other bacteria than *M. viscosa* and *A. wodanis* that produced rich growth on the plates. Then it can be concluded that *Tenacibaculum* sp. is a regularly occurring third bacterium occurring in high numbers in the ulcers. By studying the ulcers in the vaccine experiment of Example 3 it appears that *Tenacibaculum* sp. is contributing to a "biofilm" that inhibit the osmotic exchange of salt between the physiological 0.9% of the fish body and the 3 to 4% salt concentration in the seawater. This "bio-seal" provides the fish with a protection of osmotic loss of body water possibly explaining the puzzling observation that winter ulcer fish may live with large areas of their surface covered by ulcers for weeks and months without suffering from loss of body water. Another effect of the *Tenacibaculum*-seal is that the salt concentration in the exposed ulcer is kept physiologic making *A. wodanis* able to continuously inhibit the virulence of *M. viscosa* that would otherwise have killed the infected salmon in a much shorter time as demonstrated in challenge experiments in marine research facilities that disinfect their intake-water. A side-effect of the inhibitory activity of *A. wodanis* is that ulcers of winter ulcer affected salmon in the field may develop to sizes of a hand on large fish that are infected for months before the water heats up in the spring. In all possible ways the vaccination experiment of Example 3 has demonstrated that there are three different bacteria that are present in a classical "winter ulcer" infection.

In conclusion the vaccination trial in Example 3 demonstrated that *A. wodanis* dominated the pathogenesis and controlled the development of both winter ulcer and wodanosis during the whole trial. The 3 month long experiment was conducted at a seawater temperature between 9 and 10° C. except for a period of two weeks when the seawater temperature slipped down to 8° C. and as a result, with one week of delay, the roles between *A. wodanis* and *M. viscosa* switched into the same scenario as was demonstrated in the vaccination trial in Example 2 where the water temperature was permanently at 8° C. Accordingly when the temperature switched back the roles between *A. wodanis* and *M. viscosa* also switched, again with one week delay. *A. wodanis* seems to have inhibited the exponential development of the disease from two weeks after the onset of the combined infections of winter ulcer and wodanosis. This role as inhibitor of outbreaks of winter ulcer may be considered beneficial to an infected population of farmed fish but for the extended time period of the outbreak the total loss of fish may be as high as in a more acute outbreak and in addition the more chronic development of the disease makes it more difficult to argue for use of antibiotic treatment to control the infection.

The dominating role of *A. wodanis* was underlined by the result that a vaccine with singly cultivated *A. wodanis* protected the salmon smolts best while the vaccine with *M. viscosa* cultivated alone did not protect the smolts. The combined vaccine had an intermediate protection probably caused by the modified outlook of the *A. wodanis* cells that made it more difficult for the acquired immune activity to recognize *A. wodanis* when invading the smolt.

The reason for the dominating role of *A. wodanis* in the active development of wodanosis in Example 3 compared to Example 2 is considered to be the temperature difference between 8 and 9-10° C.

A Google survey of seawater temperatures along the Norwegian coast throughout the year demonstrates that because of the Gulf current the temperatures in the sea pendulate not much more extremely than between 6-8 and 10-12° C. during the four seasons for the major length of the coast. As recognized by Jensen (2003) and quantitatively identified by Aunsmo et al. (2008) there is most possibly a similar loss of salmon due to wodanosis causing septicemia and more rarely fin rot in the summer period of the year as winter ulcer is causing loss during the cold part of the year. Subsequently this may mean that as much as 85% of the loss of smolt during the three first months after sea launch may be caused by winter ulcer and wodanosis combined.

A vaccine group containing both mono-cultivated *M. viscosa* and *A. wodanis* and in addition physically co-cultivated *M. viscosa*/*A. wodanis* at 0.9% NaCl would from these results potentially protect the smolts better than any of the 3 groups involved in the study.

Example 4

Bath Challenge of Unvaccinated Smolts with Both Monocultured *A. wodanis* and Co-Cultured *M. viscosa* and *A. wodanis* in Different Relations at 9° C.

Unvaccinated smolts of Atlantic salmon of almost 100 gram in average were split and sea launched with 34 smolts into each of 3 different tanks of 1400 liter and bath infected for 1 h as in Example 3.

For the bath challenge of smolts with single culture of *Aliivibrio wodanis* (06/09/139, 5426) the challenge dose of *A. wodanis* was $1.2 \times 10^6$ cfu/ml sea water.

For bath challenge with mixed cultures of *M. viscosa* and *A. wodanis* the concentrations were $4 \times 10^5$ for *M. viscosa* and $1.2 \times 10^6$ for *A. wodanis* for group $A_{mix}$ and for group $B_{mix}$ the challenge concentrations were $1.3 \times 10^6$ cfu/ml for *M. viscosa* and $9 \times 10^6$ cfu/ml for *A. wodanis*.

Introduction of both *A. wodanis* and *M. viscosa* at the same time and with *A. wodanis* at a 3 times higher concentration than *M. viscosa* resulted in a very low level of disease development with only 20% cumulative mortality after 7 weeks. When *A. wodanis* was added to the water at a concentration of 40% lower than *M. viscosa* in the water the mortality was relatively high and the disease was considered acute. Bath challenge with both *A. wodanis* and *M. viscosa* alone at 10° C. produced acute disease and high mortality in both cases.

This experiment demonstrates that both *M. viscosa* and *A. wodanis* can infect as the sole pathogen through bath challenge at 9° C. with high mortality. In combination challenge it is possible that there is a relative concentration factor in the relation between the 2 bacteria that decides how the combined infection will proceed. However, there might be additional factors that decide the output of combined bath infections. In particular by laboratory studies on agar plates it seems that *A. wodanis* can inhibit *M. viscosa* even in a low proportion. In Example 1 it was demonstrated that if *A. wodanis* was challenging the smolt before *M. viscosa* the inhibitory effect on *M. viscosa* was larger.

There is an interesting observation seen in repeated challenge experiments including this with pure culture of either *M. viscosa* or *A. wodanis* that if the seawater is not disinfected the other Siamesian twin very effectively find its way to the host for making a combined infection. There are possibly unknown factors that make these two bacteria seek together for infecting the fish host very effectively under various conditions.

Example 5

Figure 6:
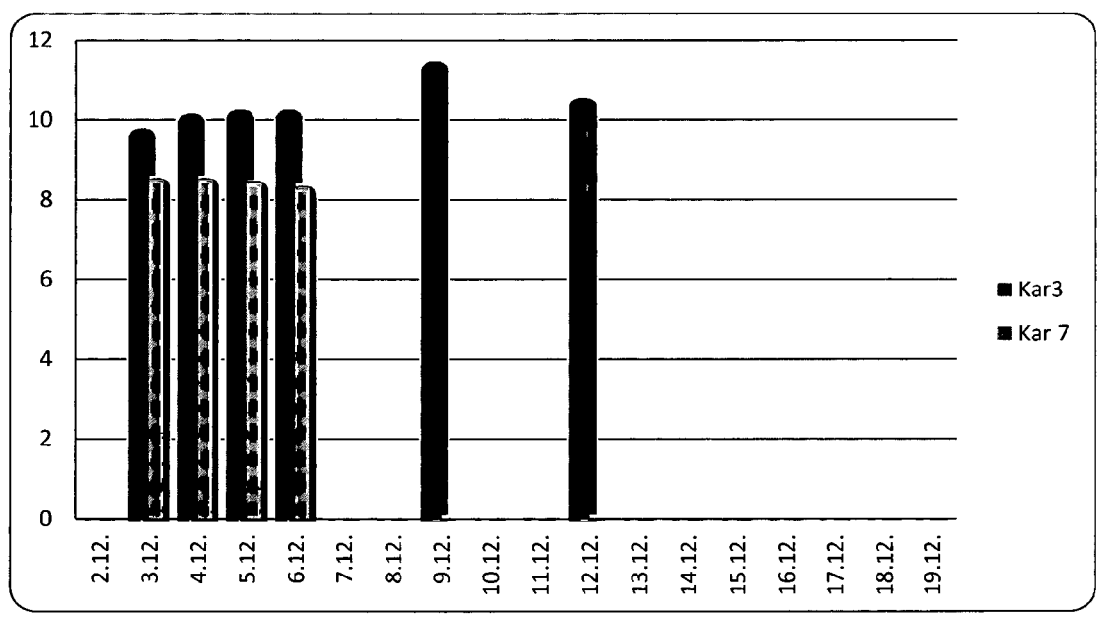

Intraperitoneal Challenge of Unvaccinated Smolts with Both Monocultured *A. wodanis* (at 8 and 10° C.) and *M. viscosa* (at 10° C.) (FIGS. 6 and 7)

Unvaccinated smolts (n=24) of Atlantic salmon of almost 100 gram in average were intraperitoneally challenged and sea launched into 2 different tanks of 1400 liter. For intraperitoneal challenge of 24 smolts with monocultures of *M. viscosa* (water temp 10° C., 7 smolts) and *A. wodanis* (17 smolts) (water temp 8° C., 7 smolts and 10° C., 10 smolts) a total of $1.3 \times 10^7$ bacteria of *M. viscosa* and $8.7 \times 10^7$ bacteria of *A. wodanis* were inoculated intraperitoneally in a volume of 0.1 ml.

Both bacteria caused high mortality with all fish dead within 2 to 4 days for both bacteria at 10° C. Also at 8° C. *A. wodanis* is producing a similar dramatic mortality when intraperitoneal challenge is employed. No ulcers or external symptoms have time to develop before the smolt is dead after intraperitoneal challenge.

The results show that *A. wodanis* is fully able to cause infection at both 8 and 10° C. when challenged intraperitoneally. It was also demonstrated that *M. viscosa* may cause infection and be highly virulent at 10° C. after ip-challenge. Example 4 and 5 demonstrate that the co-infection between *M. viscosa* and *A. wodanis* is regulated by temperature at a more narrow range than is the case when they are causing winter ulcer and wodanosis separately.

Example 6

Western Blot Experiments with Co-Cultured *M. viscosa* and *A. wodanis* and Monocultured *A. wodanis* and *M. viscosa* at Various Temperatures and NaCl Concentrations with Antibodies from Rabbits Challenged with Co-Cultured *M. viscosa* and *A. wodanis* and with *M. viscosa* and *A. wodanis* Cultivated as Single Cultures (FIGS. 1, 9a, 9b, 9c and 9d)

Antiserum Production

Antisera against *Moritella viscosa* and *A. wodanis* in single culture and against these bacteria mixed together before immunization after being cultivated separately and after being co-cultivated were produced in rabbits.

Bacteria for inoculation were grown in serum broth or on agar plate (0.9% or 2.5% NaCl, dependent on species) for 24-48 h. If the plate were grown, the bacteria are harvested by scraping and washing the plate with PBS, Formalin is added to a final concentration of 0.7% and the cultures stored overnight at 4° C.

100 µl of each culture is plated out on blood agar (with or without extra salt, dependent on species) and incubated at a suitable temperature to ensure cell death.

The cultures are then washed twice in phosphate buffered saline (PBS) and resuspended to an approximate density of McF 1 ($1 \times 10^9$ cells ml$^{-1}$) and an emulsion 50:50 in Freunds incomplete adjuvant.

Prior to inoculation blood samples (3-4 ml) are taken from each rabbit.

Rabbits are injected subcutaneously with the antigen suspension.

Injections are given weekly in consecutive doses of 0.4, and 1.0 ml.

One week after the final injection the rabbits are bled from the ear (3-4 ml).

Two weeks following bleeding, the immunisation procedure is repeated but with 1.0 ml doses throughout.

One week following the final immunisation the rabbit is bled out.

Serial dilutions of the antisera are tested in a slide agglutination assay and compared to "standard" sera.

A key feature related to the production of antibodies against cold water vibrios is developed for this project and is probably unique. The cold water *vibrio* pathogens are not able to survive at temperatures higher than room temperature and therefore will not multiply or cause disease in warm-blooded animals as rabbits. Therefore the combinations of *M. viscosa* and *A. wodanis* were injected live but washed directly subcutaneously in the rabbit. These bacteria will not produce disease or increased discomfort to the rabbit because the bacteria will die because of the higher body temperature of the rabbit (38-39° C.). In fact the inoculation culture will not develop irritation caused by remnants of formalin since formalin is not employed.

Bacterial cultures of *M. viscosa* and *A. wodanis* used for preparation of antigens for the SDS-PAGE electrophoresis and transfer to nylon membranes were cultivated at 8 and 12° C. and at 0.9 and 2.5% NaCl to mimick the key environmental factors in the winter ulcer and wodanosis infections. Standard electrophoresis of SDS polyacrylamide gels was performed and electroblotting was used for the transfer of antigens to nylon membranes. Two identical sets of antigens were run on the same gel that was blotted before the nylon membrane were cut in two and thereby making it possible to run Western blotting with two differently prepared antibodies on the same set of antigens.

Results

The results demonstrate that a combined cultivation of *A. wodanis* and *M. viscosa* produces a large array of different antigens from both bacteria compared to single cultivation before a mixture of the two cultures is used for immunization of the rabbit. This strongly verifies that *A. wodanis* and *M. viscosa* both change antigen images after being cultivated together compared to single culture propagation. In addition it seems that the number of antigens is clearly larger in co-culture for both bacteria. Also the antigens detected from single cultured or co-cultured cells seem to be mainly different. This observation points to that the co-cultivated antigenic "faces" of these bacteria are much different from their single-cultured counterpart.

Different *A. wodanis* and *M. viscosa* strains from Atlantic salmon from various geographic areas as Norway, Iceland and Scotland and from Atlantic cod show homologic antigenicity with little antigenic diversity indicating a strong cross-immunization across geographic areas and across various infected fish host species.

An important observation from the Western blot studies is that the antigenic faces shifts clearly when *A. wodanis* and *M. viscosa* is cultivated in marine salt conditions (2.5% NaCl) or in physiological salt conditions (0.9% NaCl). This means that the immune apparatus will struggle to recognize the antigenic outlook of either *A. wodanis* or *M. viscosa* both in the invading situation and in the established infection if not both types of cultured cells are involved in the vaccine composition. As with co-cultivation contra single culture propagation there are few common antigens visible on the Western blot gels from cultures grown at the two different salt concentrations.

A conclusion from the Western blot experiments is that a particularly suitable vaccine with fully optimal antigen contents contains bacteria from all variants of cultures, i.e. single cultures and co-cultures of *A. wodanis* and *M. viscosa*, and even further optimally at both about 8 and 12° C. and at about 2.5 and 0.9% NaCl. Alternatively single cultures of both *A. wodanis* and *M. viscosa* and co-culture of both at 0.9% NaCl may be mixed to gain maximal protection with few culture variants mixed).

Example 7

Wodanosis Occurring Naturally as an Acute Infection at Low Sea Temperatures

A vaccine trial with 750 well smoltified Atlantic salmon of 60 to 90 gram split in 250 smolts in each of 3 tanks of 1400 liter was started with 5 groups of 50 smolts vaccinated with research vaccines against winter ulcer and wodanosis. The smolts were transferred from fresh water, anesthetized, vaccinated with 0.1 ml of vaccine or PBS in the negative control group and then immediately transferred to sea water. No salmon smolt died or demonstrated clinical behaviour caused by improper smoltification status. Sea water was pumped from 60 meter depth in a current branch derived originally from the Gulf current of the North Atlantic Ocean. There was no disinfection of the sea water before entering the fish tanks. The water temperature varied from 6.5 to 7.5° C. during the first 7 weeks.

Results

One week after vaccination some smolts in one of the tanks started to behave unusually. The most typical behaviour was a vertical swimming at all levels ending with the mouth in the water surface and tail down. The same individuals would later "fall" down vertically to the bottom of the tank lying apparently moribund on the side but suddenly starting an active swimming ending in the same vertical position in the water. Possibly this activity could indicate a disease also involving the central nervous system. After a few hours the affected smolt got moribund and died. By Gram staining and cultivation of material from the head kidney it was found a rich pure occurrence of *A. wodanis*. After a few days the dead smolts in the affected tank displayed varying degrees of fin rot in particular at the pectoral fins and on the tail fins, but also to some degree in the other fins.

The mortality was about 3% per day for 4 weeks reducing the number of smolts with about 80%. Every smolt was cultivated and after one week nearly all dead smolts had a rich occurrence of *A. wodanis* in pure culture in the head kidney. Every smolt had one or more ulcer most commonly behind the pectoral fins possibly initiated by physical damage of the skin from sharp bony spines of the necrotized fins. However a necrosis of the tip of the mandibular jaw was common developing into complete necrosis of the jaw in a few cases. Also from the ulcer *A. wodanis* was isolated in pure culture or dominating a mixed culture with other small numbers of other bacteria.

After 4 weeks the mortality was reduced but still smolts died every day in the tank with the same cultivation result. In the remaining 2 tanks of the experiment there were also a low mortality in parallel with the disease in the highly affected tank and the microscopy and cultivation results demonstrated the same findings of *A. wodanis* from each of the affected smolts. There was no difference in occurrence of disease related to the different vaccination groups most probably because of lack of development of acquired immunity that is expected to be optimally developed 8 weeks after vaccination.

The results of the early part of Example 7 demonstrate that *A. wodanis* can cause disease alone, wodanosis, at low sea water temperatures. The mortality can be high (tank 1) and low (tank 2 and 3). This is different from the co-infection between *M. viscosa* and *A. wodanis* when the virulence of both bacteria is reduced and controlled by *A. wodanis*.

Example 8

Figure 10:
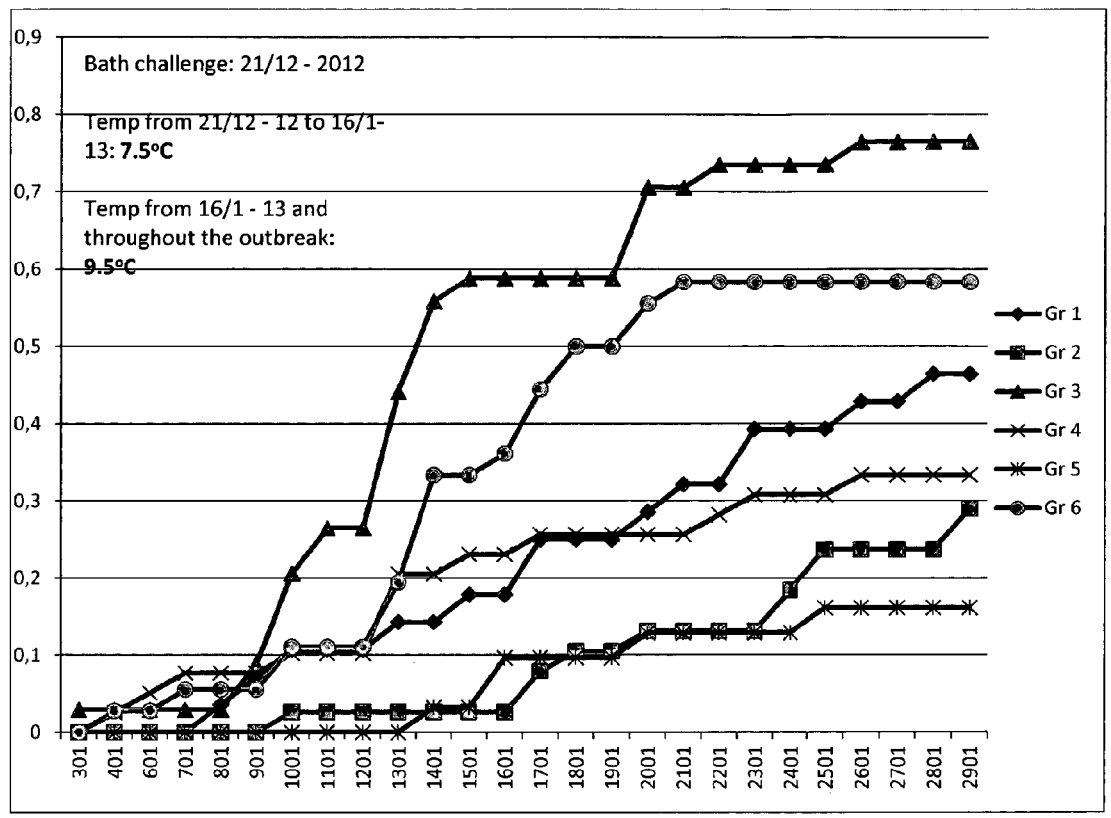

Vaccination Trial with Experimental Vaccines Consisting of Various Components of *M. viscosa* and *A. wodanis* Cultivated Singly or Together at High and Low NaCl Level and High and Low Temperature Level in Accordance with Results in Previous Vaccine-Challenge Experiments and in Particular Example 6 Western Blots (FIG. 10)

Salmon smolts were Atlantic salmon purchased from University of Environmental and Biological Sciences, Ås. The size was varying between 50 and 120 gram and they were well smoltified ready for sea launch. The smolts were shipped for only 30 minutes and stored for nearly 2 weeks in fresh water at close to 8 degrees Celsius. The fish were vaccinated with 6 different experimental vaccines including a negative control with phosphate buffered saline and an adjuvant control and left in the same tank of 1400 liter constantly supplied with sea water from 60 meter depth at a volume of from 500 to 800 liter per hour. A volume of 0.1 ml vaccine was injected intraperitoneally approximately one centimeter in front of pelvis. The smolts were marked with Alcian blue with a manually operated air pressure driven tattoo pistol in front of and behind the pelvic fins. During vaccination and transferred to sea water immediately after vaccination Experimental Vaccines Used:

Group 1 (60 smolts) vaccinated with phosphate buffered saline (PBS)

Group 2 (60 smolts) vaccinated with *M. viscosa* cultivated at 8 degrees Celsius at both 0.9 and 2.5% NaCl. i.e. one culture comprising *M. viscosa* cultivated at 8° C. at 2.5% NaCl and one culture comprising *M. viscosa* cultivated at 8° C. at 2.5% were mixed together and used for the vaccination. These two cultures were mixed evenly.

Group 3 (61 smolts) vaccinated with *A. wodanis* cultivated at 10 degrees Celsius at both 0.9 and 2.5% NaCl. one culture comprising *A. wodanis* cultivated at 10° C. at 2.5 NaCl and one culture comprising *A. wodanis* cultivated at 10° C. at 0.9% NaCl were mixed together and used for the vaccination. These two cultures were mixed evenly.

Group 4 (60 smolts) vaccinated with *M. viscosa* and *A. wodanis* cultivated in the same broth according to an established procedure reported in this document at 8 and 10 degrees Celsius and at both 0.9 and 2.5% NaCl resulting in 4 different cultures, i.e. one mixed culture of *A. wodanis* and *M. viscosa* cultivated at 8° C. and 0.9% NaCl, one mixed culture of *A. wodanis* and *M. viscosa* cultivated at 8° C. and 2.5% NaCl, one mixed culture of *A. wodanis* and *M. viscosa* cultivated at 10° C. and 0.9% NaCl and one mixed culture of *A. wodanis* and *M. viscosa* cultivated at 10° C. and 2.5% NaCl, that were mixed evenly Group 5 (55 smolts) vaccinated with *M. viscosa* and *A. wodanis* cultivated in the same broth at 8 and 10 degrees Celsius and at both 0.9 and 2.5% NaCl as indicated for group 4 and in addition monocultures of *M. viscosa* and *A. wodanis* as in Group 2 and 3 resulting in 8 different cultures that were mixed evenly.

Group 6 (60 smolts) vaccinated with only adjuvant prepared in PBS. This adjuvant was also applied for Group 2, 3, 4 and 5 and consisted of 60% v/v Curdlan (200 mikrogram per individual smolt) made from a stock of 10 mg/ml in PBS and 40% v/v Freunds incomplete adjuvant.

The vaccine cultures were grown to late logarithmic phase and inactivated by heating the cultures to 30° C. for 16 hours without emptying the cultures from the culture flasks and without adding any extra component. After this heat inactivation at 30° C. the viability of the cultures was controlled by cultivation on blood agar plates with 2.5 and 0.9% NaCl before the cells were spun down and washed in PBS and used directly in the vaccine preparation. There was no growth of either *M. viscosa* or *A. wodanis* from any of the cultures after heat inactivation at 30° C. This technique of heat activation cold water vibrios inactivates the bacterial cells by heat which is low enough to leave proteins and other antigens with their natural structure configuration theoretically improving the recognisability of the live bacteria by the acquired immune reaction when the bacteria approaches the immunized salmon.

Two weeks after vaccination the smolts in all groups started to die with fin rot and septicemic infection mainly caused by *A. wodanis*. From ulcers a mixture of bacteria were cultivated often with *A. wodanis* included. The smolts died in a period of 5 weeks before the mortality ceased. The negative control was reduced with 23 smolts in this period while the other groups lost 5 smolts for group 2 and about 10 smolts for the remaining groups indicating an adjuvant protection before the specific protection caused by the vaccine antigens was developed. The mortality in the tank was low until a pump failure 4 months after vaccination and between 20 to 30% of the remaining smolts were lost due to oxygen deficit.

After 5 months and 1 week a bath challenge with *M. viscosa* and *A. wodanis* cultivated in the same culture at 9 degrees Celsius in 0.9% NaCl with *M. viscosa* cultivated in monoculture at 9 degrees Celsius and 2.5% NaCl and with *A. wodanis* cultivated in monoculture at 9 degrees Celsius with approximately one third of each type of challenge culture. The sea water in the tank was lowered to 15% of normal level and oxygenated, the flow of water was stopped for one hour after the challenge started before the flow was started and the bacterial cultures were diluted gradually.

After 13 days the first salmon were found dead and an outbreak of typical "winter ulcer" started with both *M. viscosa* and *A. wodanis* isolated from the kidney and ulcers developed in the diseased salmon. Two weeks into the outbreak the temperature of the water were elevated from 7.5 degrees Celsius to 9.5 degrees Celsius by electrical heating of the intake water. The heating was continued for 4 weeks. The disease outbreak continued with ulcers and mortality for two more weeks after the water was heated.

Results

Diseased and dead salmon demonstrated dominating growth of *M. viscosa* from ulcers and head kidney in the first half of the outbreak but always together with *A. wodanis*, while *A. wodanis* dominated in numbers on after the heating of the intake water started 2 weeks into the outbreak. The results from the challenge and outbreak of a co-infection of winter ulcer and wodanosis in Experiment 8 is presented in FIG. 10.

Salmon without any vaccine (Group 1) is protected to some extent throughout the experiment caused by an undisturbed immune apparatus that protects the salmon equally well against both winter ulcer and wodanosis. The introduction of adjuvant to the salmon protects the fish the first weeks after vaccination before acquired immunity develops, however, it is clear that in the first part of the outbreak challenged by bath when *M. viscosa* is dominating, the adjuvant is possibly by some redirection of the immune mechanisms increasing the severity of winter ulcer. In the other half of the combined winter ulcer and wodanosis outbreak when the temperature is elevated with two degrees *A. wodanis* is the dominating pathogen by virulence and the adjuvant seems to protect against wodanosis alone unspecifically. The same tendency was observed in Experiment 3.

Salmon vaccinated with only *M. viscosa* seem to be optimally protected against ulcers and death at low temperatures during a co-infection. However at temperatures above 8° C. fish in this group is unprotected against wodanosis and already the first days after the temperature increase and throughout the outbreak the fish in this group seem to be vulnerable for the wodanosis part of the co-infection.

Salmon vaccinated against only *A. wodanis* is clearly vulnerable for getting diseased by winter ulcer caused mainly by two factors which is the increased risk to be diseased by *M. viscosa* when injected with adjuvant intraperitoneally and secondly the effect of vaccinating against the *A. wodanis* that regulate down the virulence of *M. viscosa* at low temperatures when *M. viscosa* is most active.

The vaccine with both *M. viscosa* and *A. wodanis* cultivated in the same culture protects the salmon to the same degree against winter ulcer caused by *M. viscosa* as the reduced protection obtained by using Freunds incomplete adjuvant. At higher temperatures this vaccine protects quite well against wodanosis.

A suitable vaccine against ulcers in farmed Atlantic salmon hence seems to be a vaccine that contains a mixture of antigens produced when *M. viscosa* and *A. wodanis* is cultivated as monocultures or single cultures and as mixed cultures at high and low salt and high and low temperature. In Example 7 it is shown that wodanosis may occur also at low temperatures causing high morbidity and mortality at temperatures from below 6 to 7° C. This means that an vaccine may be improved by in additions to the 8 components included in the research vaccine used in Group 5 in Example 8 contain *A. wodanis* cultivated at high and low concentrations of salt at low temperature i.e. in total 10 culture components instead of the 8 culture components included in the vaccine in Group 5 of Experiment 8. It means that acquired immunity at all levels of infection development is suitable from both the outer parts of the salmon to the internal organs to protect it from winter ulcer and wodanosis occurring as mono-infections or as co-infection. From the results in Lunder et al. 1995 it may be estimated that co-infection between *M. viscosa* and *A. wodanis* occurs in less than one third of the salmon with ulcers while mono-infection with *A. wodanis* occurs in more than one third of salmon with ulcers when comparing all infected individuals. Mono-infection with *M. viscosa* causes rapid onset of infection with high mortality as verified in several published challenge studies while a co-infection between *M. viscosa* and *A. wodanis* is causing a disease with longer incubation time and low mortality as demonstrated in the various experiments of this study and also from field observations that points to high morbidity but normally low mortality in typical outbreaks of "winter ulcer". The results of Experiment 7 show that a natural outbreak of wodanosis in newly sea-launched smolts caused by *A. wodanis* without involvement of *M. viscosa* may have a mortality of 80% in 4 weeks i.e. a daily mortality rate of about 3% which is close to 60% total mortality that may occur after bath challenges with only *M. viscosa* (Løvoll et al. 2008). In summary based on the variation in mortality for mono- and co-infections with these two pathogens the results of Lunder et al. 1995 may be used to speculate that close to 40% of the salmon with ulcer disease caused by *M. viscosa* and/or *A. wodanis* are infected with *A. wodanis* as the only primary pathogen. *M. viscosa* and *A. wodanis* are based on these speculations causing co-infections in a relatively lower number of the cases maybe in close to 20% of the salmon with ulcer disease in an un-vaccinated population as in Lunder et al. 1995. However, since the virulence of both *M. viscosa* and *A. wodanis* is down-regulated by *A. wodanis* in a co-infection the number of co-infected salmon that are diseased but still alive constitutes a relatively large proportion of all the sampled diseased salmon.

In a commercially vaccinated (vaccine antigens from *M. viscosa* cultivated as monoculture) population of Atlantic salmon in aquaculture, the number of cases with properly defined winter ulcer caused by *M. viscosa* alone is low or minimal. In ulcer disease in a commercially vaccinated population the proportion of diseased salmon with mono-infection with *A. wodanis* (wodanosis) is increased at both high and low temperature (year-round). However, the proportion of diseased individuals with a co-infection will still be high and possibly dominate if salmon with visible ulcers in a population with ulcers are sampled alive in the cold periods of the year with sea temperatures below 9° C. In such a population an investigation of dead salmon will most probably show a majority of individuals with mono-infection with *A. wodanis* and these individuals may not present ulcers or have fewer or smaller ulcers. The majority of the living but diseased individuals in a population with ulcers vaccinated commercially will still be infected with *M. viscosa* but very often in a co-infection with *A. wodanis*. The reason for this is that when a co-infection develops between *M. viscosa* and *A. wodanis* in a commercially vaccinated salmon, the antigens presented by the *M. viscosa* cells are dramatically changed according to the Western blot experiments (Experiment 6). Because of this the immune apparatus of the salmon is not able to properly recognize the *M. viscosa* cells and eliminate them when the smolt is vaccinated with one of the commercial vaccines used in the Atlantic salmon farming industry the last 20 years.

In the summer period i.e. when sea temperatures are between 9° C. and up to 15-16° C. there will be outbreaks with wodanosis causing ulcers but with many dead fish that are not displaying ulcers or with fewer or smaller ulcers. These ulcers are often initiated by physical removing of scales and/or creation of small wounds either by contact with nets or other equipment or from skin punctures made by eroded sharp bony spines of fins in smolts with varying degrees of fin rot. *M. viscosa* seems to create ulcers primarily and more frequently when it is involved in winter ulcer or more common a mixed infection of winter ulcer and wodanosis in commercially vaccinated salmon in the colder periods of the year. This scenario has been puzzling fish bacteriologists, fish health personnel and vaccine companies since the vaccination against winter ulcer started 20 years ago.

Two of the 5 dead fish in Group 5 were only having infection and puncture of the eye on one side. The rest of the fish body were nice and unaffected by any ulcers. A third salmon were also looking very nice except for bleedings in the liver and ascites. The two remaining salmon that died in group 5 where having ulcers like most fish that died in the outbreak Experiment 8 verifies that a suitable vaccine against wodanosis and winter ulcer and the co-occurrence of these diseases contains antigens from 8 or more (12) variant cultures with *M. viscosa* and *A. wodanis* cultured separately and together in a certain balance at high and low salt to be optimally protecting the Atlantic salmon throughout the production cycle. The results of Experiment 8 fit well with the large variation of the protein outlook of *M. viscosa* and *A. wodanis* at high and low salt and temperature in the Western blot studies of Experiment 6.

SUMMARY OF THE EXPERIMENTAL RESULTS

Challenge and vaccine experiments demonstrate that *A. wodanis* causes a separate disease, wodanosis, and that *M. viscosa* causes another separate disease, winter ulcer. The two bacteria occur together in the cold marine water where fish farming is performed. In the field situation as under experimental conditions mimicking the field situation it is demonstrated that the two bacteria act together in a double "siamesic twin" infection in most situations. The way they interact depends on some factors of which temperature and salt are important.

Bath challenge studies of unvaccinated smelts at 9 to 10° C. with monocultures of *A. wodanis* and *M. viscosa* produces a relatively acute disease in both cases killing most fish within 1 week after the outbreak starts beginning from 2 days after bath challenge. Bath challenge with *M. viscosa* at water temperatures between 6.4 and 7.6° C. causes typical winter ulcer and relatively acute disease development. Bath challenge with *A. wodanis* at this low temperature causes lower mortality, in one example <10% compared to almost 100% for *M. viscosa*.

Co-challenge in bath with both *A. wodanis* and *M. viscosa* at low temperature reduces the development of winter ulcer if the *A. wodanis* is added to the water before *M. viscosa* and with increasing degree the earlier in time *A. wodanis* is added. With 3 hour pre-challenge with *A. wodanis* the mortality is reduced from day 6 after challenge and cumulative mortality was reduced with 10% after 17 days. Introduction of *A. wodanis* 8 days before *M. viscosa* was introduced in the water reduced the cumulative mortality to 20% after 17 days compared to 95% mortality in the groups where both bacteria where introduced in the water at the same time, the same mortality as was occurring when *M. viscosa* was the only bacterium used in the challenge.

At higher water temperatures introduction of both *A. wodanis* and *M. viscosa* at the same time and with *A. wodanis* at a 3 times higher concentration than *M. viscosa* resulted in a very low level of disease development with only 20% cumulative mortality after 7 weeks. When *A. wodanis* was added to the water at a concentration of 40% lower than *M. viscosa* in the water the mortality was relatively high and the disease was considered acute. Bath challenge with both *A. wodanis* and *M. viscosa* alone at 10° C. produced acute disease and high mortality in both cases.

Infection studies with *A. wodanis* and *M. viscosa* intraperitoneally in unvaccinated Atlantic salmon smolts as single cultures demonstrate that both bacteria produce high mortality with all fish dead within 3 to 4 days for both bacteria at 10° C. Also at 8° C. *A. wodanis* is producing a similar dramatic mortality when intraperitoneal challenge is employed. No ulcers or external symptoms have time to develop before the smolt is dead after intraperitoneal challenge.

Vaccination trials demonstrate that a vaccine with *A. wodanis* grown in single culture is protecting against wodanosis at high temperature for the acute phase of the disease. A vaccine with *M. viscosa* grown in single culture is protecting against winter ulcer as the commercial vaccines against winter ulcer is shown to do under experimental conditions at low temperatures (<8° C.) but is not protecting against a co-infection between the two bacteria at 9 to 10° C. due to the occurrence of wodanosis. A vaccine with both *A. wodanis* and *M. viscosa* cultivated in a mixed culture is not protecting better than a vaccine with *M. viscosa* cultivated alone at low temperature due to the acute phase of winter ulcer at this stage requiring the simultaneous administration of single culture *M. viscosa*. The mortality is the same in both vaccine groups, however the ulcer development is larger in the group vaccinated with a vaccine of both bacteria grown together possibly because the salmon in this group were not protected against the wild type non-modulated *M. viscosa* that are responsible for the initiation of ulcers. Similarly the same mixed vaccine is only half as effective as the vaccine with *A. wodanis* grown as single culture at high temperature.

The vaccination trials demonstrate that both *A. wodanis* and *M. viscosa* infect the fish as unchanged cells before being impacted by physical or a similar contact to the other "Siamese twin". *M. viscosa* is initiating the ulcer development before being in contact with *A. wodanis* as down-regulator of the virulence. The physical contact in the fish skin/ulcer or in the inner organs of the fish at low salt concentration change the outlook of both bacteria and *A. wodanis* turns into the master down-regulator of virulence of *M. viscosa* at low temperature. At high temperature *A. wodanis* continues to down-regulate the virulence of *M. viscosa* but is also reducing its own virulence as a result of the physical or similar contact with *M. viscosa*. In addition both bacteria change the physical outlook after being in contact with each other at low salt concentration. A vaccine with the changed physical outlook of the cells protects the smolts less optimally against winter ulcer and wodanosis than a vaccine with original outlook of the pathogens. However, for protection against established and prolonged infection with these two pathogens a vaccine should contain bacterial antigens from cells from both single cultures and mixed cultures between *A. wodanis* and *M. viscosa* cultivated at high and low temperature and high and low salt concentration.

Wodanosis caused by *A. wodanis* alone may occur as outbreaks with high mortality at low temperatures down to and below 6 degrees Celsius especially when predisposing factors make small wounds to the skin caused for example by eroded fin spines caused for example by fin rot caused by other bacteria as *Tenacibaculum* spp. or mechanical injuries as to the mandibula in crowded or socially stressed conditions.

REFERENCES

Aunsmo A, Bruheim T, Sandberg M, Skjerve E, Romstad S, Larssen R B. 2008. Methods for investigating patterns of mortality and quantifying cause-specific mortality in sea-farmed Atlantic salmon *Salmo salar*. Dis Aquat Organ. 2008 Aug. 27; 81(2):99-107.

Benediktsdòttir, E., Verdonck, L., Saltier, C., Helgason, S., Swings, J. 2000. Characterization of *Vibrio viscosus* and *Vibrio wodanis* isolated at different geographical locations: a proposal for reclassification of *Vibrio viscosus* as *Moritella viscosa* comb. nov. Int J Syst Evol Microbial, 50: 479-88.

Bjornsdottir B, Hjerde E, Bragason B T, Gudmundsdottir T, Willassen N P, Gudmundsdottir B K. 2012. Identification of type VI secretion systems in *Moritella viscosa*. Vet Microbial. 2012 Aug. 17; 158(3-4):436-42.

Bruno, D. W., Griffiths, J., Petrie, J., Hastings, T. S. 1998. *Vibrio viscosus* in farmed Atlantic salmon *Salmo salar* in Scotland: field and experimental observations. Dis. Aquat. Org. 34: 161-166.

Greger, E. and Goodrich, T. 1999. Vaccine development for winter ulcer disease, *Vibrio viscosus*, in Atlantic salmon, *Salmo salar* L. J Fish Dis 22: 193-199.

Grove S, Wiik-Nielsen C R, Lunder T, Tunsjø H S, Tandstad N M, Reitan L J, Marthinussen A, Sørgaard M, Olsen A B, Colquhoun D J. 2010. Previously unrecognised division within *Moritella viscosa* isolated from fish farmed in the North Atlantic. Dis Aquat Organ. December 7; 93(1): 51-61.

Gudmundsdòttir, B. K., Björnsdòttir, B., Gudmundsdòttir, S., Bambir, S. H. 2006. A comparative study of susceptibility and induced pathology of cod, *Gadus morhua* (L.), and halibut, *Hippoglossus hippoglossus* (L.), following experimental infection with *Moritella viscosa*. J Fish Dis 29: 481-487.

Jensen, F. 2003. Overraskende mye vintersår. (Surprisingly high frequency of Winter Ulcer). Norsk Fiskeoppdrett, nr 4, 42-43.

Karlsen, C., Sørum, H., Willassen, N. P., Åsbakk, K. 2012. *Moritella viscosa* bypasses Atlantic salmon epidermal keratocyte clearing activity and might use skin surfaces as a port of infection. Vet Microbial, 154(3-4):353-62. Epub 2011 Jul. 30.

Løvoll, M., Wiik-Nielsen, C. R., Tunsjø, H. S., Colquhoun, D., Lunder, T., Sørum, H., Grove, S. 2009. Atlantic salmon bath challenged with *Moritella viscosa*—Pathogen invasion and host response. Fish Shellfish Immunol, 26: 877-884.

Lunder, T. 1992. "Winter ulcer" in Atlantic salmon. A study of pathological changes, transmissibility, and bacterial isolates. PhD thesis Norwegian School of Veterinary Science.

Lunder, T., Evensen, Ø., Holstad, G., and Håstein, T. 1995. "Winter ulcer" in the Atlantic salmon *Salmo salar*. Pathological and bacteriological investigations and transmission experiments. Dis. Aquat. Org. 23: 39-49.

Lunder, T., Sørum, H., Holstad, G., Steigerwalt, Mowinckel, P. and Brenner, D. J. 2000. Phenotypic and genotypic characterization of *Vibrio viscosus* sp. nov. and *Vibrio wodanis* sp. nov. isolated from Atlantic salmon (*Salmo salar*) with "winter ulcer". Int. J. Syst. Evol. Microbiol. 50: 427-450.

O'Hallovan, I., Saulnier, E., Were, K., Groman, D., Lall, S. 1991. Cold water winter lesions in Atlantic salmon. Can Vet J, vol. 32, May, 312.

Olsen A B, Nilsen H, Sandlund N, Mikkelsen H, Sørum H, Colquhoun D J. 2011. *Tenacibaculum* sp. associated with winter ulcers in sea-reared Atlantic salmon *Salmo salar*. Dis Aquat Organ; 94:189-99.

Thorarinsson, R., Lystad, Y. 2003. Norsk fiskeoppdrett, nr 10, 34-38.

Urbanczyk, H., Ast, J. C., Higgins, M. J., Carson, J. Dunlap, P. V. 2007. Reclassification of *Vibrio fischeri, Vibrio logei, Vibrio salmonicida* and *Vibrio wodanis* as *Aliivibrio fischeri* gen. nov., comb. nov., *Aliivibrio logei* comb. nov., *Aliivibrio salmonicida* comb. nov. and *Aliivibrio wodanis* comb. nov. int. J. Syst. Evol. Microbial., 57, 2823-2829.

Whitman, K. A., Backman, S., Benediktsdottir, E., Coles, M., Johnson, G. 2000. Isolation and characterization of a new *Vibrio* spp. (*Vibrio wodanis*) associated with "Winter Ulcer Disease" in sea water raised Atlantic salmon (*Salmo salar* L.) in New Brunswick. Aquacul. Assoc. Canada Spec. Publ. No. 4, 115-117.

The invention claimed is:

1. A method for preventing and/or treating wodanosis in a fish, comprising administering an effective amount of a composition comprising inactivated bacteria of one or more mixed culture(s) of spp. *Alliivibrio wodanis* (*A. wodanis*) and *Moritella viscosa* (*M. viscosa*) to a fish, wherein said mixed culture of spp. *A. wodanis* and *M. viscosa* comprises cells of *A. wodanis* and *M. viscosa* that are cultured in a way that creates physical cell-cell contact between said *A. wodanis* and *M. viscosa* cells and/or cultured in the presence of extracellular components from individual or mixed cultures of *M. viscosa* and *A. wodanis*, and wherein said effective amount is sufficient to trigger an immune response in said fish.

2. The method according to claim 1, wherein said inactivated bacteria have been obtained from one or more mixed cultures of *A. wodanis* and *M. viscosa* which have been cultivated at a temperature of about 10-12° C. (high).

3. The method according to claim 1, wherein said inactivated bacteria have been obtained from one or more mixed cultures of *A. wodanis* and *M. viscosa* which have been cultivated at a temperature of about 7-8° C. (low).

4. The method according to claim 1, wherein said inactivated bacteria have been obtained from one or mixed cultures of *A. wodanis* and *M. viscosa* which have been cultivated at a salt concentration of about 0.9% (low).

5. The method according to claim 1, wherein said inactivated bacteria have been obtained from one or more mixed cultures of *A. wodanis* and *M. viscosa* which have been cultivated at a salt concentration of about 2.5% (high).

6. The method according to claim 1, wherein said composition further comprises an adjuvant and/or a pharmaceutically acceptable excipient.

7. The method according to claim 1, wherein said fish is a salmonid (Salmonidae) selected from the group consisting of salmon, Atlantic salmon, or rainbow trout; or atlantic cod, turbot or fish of the species Labridae.

8. The method according to claim 1, wherein said administration is performed by intraperitoneal injection, by bath vaccination, or by oral vaccination.

9. The method according to claim 1, wherein said composition further comprises inactivated bacteria of a single culture of spp. *A. wodanis* and/or *M. viscosa*.

10. The method according to claim 9, wherein said *A. wodanis* and/or *M. viscosa* has been cultivated at a temperature of about 10-12° C. (high).

11. The method according to claim 9, wherein said *A. wodanis* and/or *M. viscosa* has been cultivated at a temperature of about 7-8° C. (low).

12. The method according to claim 9, wherein said *A. wodanis* and/or *M. viscosa* has been cultivated at a salt concentration of about 0.9% (low).

13. The method according to claim 9, wherein said *A. wodanis* and/or *M. viscosa* has been cultivated at a salt concentration of about 2.5% (high).

14. The method of claim 1, wherein said fish is further infected with winter ulcer and said administering treats and/or prevents said winter ulcer.

15. A method for preventing and/or treating wodanosis in a fish, comprising administering an effective amount of a composition, wherein said composition comprises inactivated bacteria obtained from:
   a) one or more single culture(s) of *A. wodanis* cultured at a temperature of about 10° C., and at a sodium salt concentration of about 0.9% salt,
   b) one or more mixed culture(s) of *A. wodanis* and *M. viscosa* cultured at a temperature of about 10° C. and at a sodium salt concentration of about 0.9%, and
   c) optionally one or more single culture(s) of *M. viscosa* cultured at a temperature of about 10° C. and at a sodium salt concentration of about 0.9%,
   wherein said effective amount is sufficient to trigger an immune response in said fish.

16. A method for preventing and/or treating a co-infection of wodanosis and winter ulcer in a fish, comprising administering an effective amount of a composition, wherein said composition comprises inactivated bacteria obtained from:
   a) one or more single culture(s) of *M. viscosa* cultured at a temperature of about 8° C. and a sodium salt concentration of about 0.9% salt,
   b) one or more single culture(s) of *M. viscosa* cultured at a temperature of about 8° C. and a sodium salt concentration of about 2.5% salt,
   c) one or more single culture(s) of *A. wodanis* cultured at a temperature of about 10° C. and a sodium salt concentration of about 0.9%,
   d) one or more single culture(s) of *A. wodanis* cultured at a temperature of about 10° C. and a sodium salt concentration of about 2.5%, e) one or more mixed culture(s) of *M. viscosa* and *A. wodanis* cultured at a temperature of about 8° C., and a sodium salt concentration of about 0.9%,
f) one or more mixed culture(s) of *M. viscosa* and *A. wodanis* cultured at a temperature of about 8° C. and a salt concentration of about 2.5%,
g) one or more mixed culture(s) of *M. viscosa* and *A. wodanis* cultured at a temperature of about 10° C. and a salt concentration of about 0.9%,
h) one or more mixed culture(s) of *M. viscosa* and *A. wodanis* cultured at a temperature of about 10° C. and a sodium salt concentration of about 2.5%, and optionally
i) inactivated bacteria obtained from one or more single culture(s) of *A. wodanis* cultured at a temperature of about 8° C. and a salt concentration of about 2.5%, and further optionally
j) inactivated bacteria obtained from one or more single culture(s) of *A. wodanis* cultured at a temperature of about 8° C. and a sodium salt concentration of about 0.9%, and further optionally
k) inactivated bacteria obtained from one or more single culture(s) of *M. viscosa* cultured at about 10° C., and at a sodium salt concentration of 2.5% salt, and further optionally
l) inactivated bacteria obtained from one or more single culture(s) of *M. viscosa* cultured at about 10° C. and at a sodium salt concentration of about 0.9% salt, wherein said effective amount is sufficient to trigger an immune response in said fish.

17. The method of claim 4, wherein said salt is sodium.
18. The method of claim 5, wherein said salt is sodium.

* * * * *

UNITED STATES PATENT AND TRADEMARK OFFICE
CERTIFICATE OF CORRECTION

| | | |
|---|---|---|
| PATENT NO. | : 9,446,108 B2 | Page 1 of 1 |
| APPLICATION NO. | : 14/401257 | |
| DATED | : September 20, 2016 | |
| INVENTOR(S) | : Henning Sorum | |

It is certified that error appears in the above-identified patent and that said Letters Patent is hereby corrected as shown below:

On the Title page, at (86), please correct the PCT No.: from PCT/EF2013/059972 to PCT/EP2013/059972.

Signed and Sealed this
Eighth Day of November, 2016

Michelle K. Lee
*Director of the United States Patent and Trademark Office*